US012173278B2

(12) United States Patent
Collins et al.

(10) Patent No.: US 12,173,278 B2
(45) Date of Patent: Dec. 24, 2024

(54) MUTANTS OF PAENIBACILLUS AND METHODS FOR THEIR USE

(71) Applicant: Bayer CropScience LP, St. Louis, MO (US)

(72) Inventors: Jennifer Anne Collins, Dixon, CA (US); Jesus F. Sanchez, Woodland, CA (US); James L. Waller, West Sacramento, CA (US); Bjorn A. Traag, Walnut Creek, CA (US); Sara K. Hotton, Davis, CA (US); Tony J. Tegeler, West Sacramento, CA (US)

(73) Assignee: Bayer CropScience LP, St. Louis, MO (US)

( * ) Notice: Subject to any disclaimer, the term of this patent is extended or adjusted under 35 U.S.C. 154(b) by 814 days.

(21) Appl. No.: 17/054,951

(22) PCT Filed: May 8, 2019

(86) PCT No.: PCT/US2019/031264
§ 371 (c)(1),
(2) Date: Nov. 12, 2020

(87) PCT Pub. No.: WO2019/221988
PCT Pub. Date: Nov. 21, 2019

(65) Prior Publication Data
US 2021/0244031 A1 Aug. 12, 2021

Related U.S. Application Data

(60) Provisional application No. 62/671,067, filed on May 14, 2018.

(51) Int. Cl.
*C12N 1/20* (2006.01)
*A01N 63/25* (2020.01)
*C07K 14/195* (2006.01)
*C12R 1/01* (2006.01)

(52) U.S. Cl.
CPC .............. *C12N 1/20* (2013.01); *A01N 63/25* (2020.01); *C12N 1/205* (2021.05); *C12R 2001/01* (2021.05)

(58) Field of Classification Search
CPC .......... C12N 1/20; C12N 1/205; A01N 63/25; C12R 2001/01; C07K 14/195
See application file for complete search history.

(56) References Cited

U.S. PATENT DOCUMENTS

| 9,883,676 | B2 | 2/2018 | Beau et al. |
| 9,938,550 | B1 | 4/2018 | Huang et al. |
| 10,159,257 | B2 | 12/2018 | Beau et al. |
| 10,499,656 | B2 | 12/2019 | Beau et al. |
| 10,703,775 | B2 | 7/2020 | Kimmelshue et al. |
| 10,988,769 | B2 | 4/2021 | Curtis et al. |
| 11,623,944 | B2 * | 4/2023 | Beau ................ C12N 9/93 514/183 |
| 2016/0278388 | A1 * | 9/2016 | Beau ................ C07K 14/195 |
| 2020/0054023 | A1 | 2/2020 | Beau et al. |
| 2021/0127684 | A1 | 5/2021 | Singh et al. |
| 2021/0204550 | A1 | 7/2021 | Görtz |
| 2021/0238610 | A1 | 8/2021 | Curtis et al. |

FOREIGN PATENT DOCUMENTS

| KR | 2014 0025265 A | 6/2014 |
| WO | 2014/092345 A1 | 6/2014 |
| WO | 2016/154297 A1 | 9/2016 |
| WO | 2017/151742 A1 | 9/2017 |

OTHER PUBLICATIONS

Cairns et al (An alternate route to phosphorylating DegU of Bacillus subtilis using acetyl phosphate). BMC Microbiology, 15, 78. (Year: 2015).*
Juneja, P., et al., U.S. Appl. No. 17/276,267, filed Mar. 15, 2021, "Methods of Controlling Animal Pests With Paenibacillus Terrae," U.S. Appl. No. 17/276,267, filed Mar. 15, 2021.
Cockburn, D., et al., "Analysis of Surface Binding Sites (SBSs) in Carbohydrate Active Enzymes with Focus on Glycoside Hydrolase Families 13 and 77—A Mini Review," Biologia, 2014, vol. 69, No. 6, pp. 705-712.
Dahl, M.K. et al., "The Phosphorylation State of the DegU Response Regulator Acts as a Molecular Switch Allowing Either Degradative Enzyme Synthesis or Expression of Genetic Competence in Bacillus subtilis," J. Biol. Chem., 1992, vol. 267, No. 20, pp. 14509-14514.
Han, Y.W., et al., "Production of Microbial Levan from Sucrose, Sugarcane Juice and Beet Molasses," Journal of Industrial Microbiology, 1992, vol. 9, pp. 257-260.
Jers., C. et al., "Bacillus subtilis Two-Component System Sensory Kinase DegS is Regulated by Serine Phosphorylation in Its Input Domain," PLoS One, 2011, vol. 6, No. 2, e14653.
Li, O., et al., "Increasing Viscosity and Yields of Bacterial Exopolysaccharides by Repeatedly Exposing Strains to Ampicillin," Carbohydrate Polymers, Apr. 2, 2014, vol. 110, pp. 203-208.
Li, O., et al., "Two UDP-Glucuronic Acid Decarboxylases Involved in the Biosynthesis of a Bacterial Exopolysaccharide in Paenibacillus elgii," Applied Microbiology and Biotechnology, Jan. 10, 2015, vol. 99, No. 7, pp. 3127-3139.
Li, O., et al., "Supplementary Material: Two UDP-Glucuronic Acid Decarboxylases Involved in the Biosynthesis of a Bacterial Exopolysaccharide in Paenibacillus elgii," Applied Microbiology and Biotechnology, Jan. 10, 2015, vol. 99, No. 7, pp. 3127-3139.
Li, O., et al., "Identification ad Characterization of Six Glycosyltransferases Involved in the Biosynthesis of a New Bacterial Exopolysaccharide in Paenibacillus elgii," Applied Microbiology and Biotechnology, Dec. 3, 2017, vol. 102, No. 3, pp. 1357-1366.

(Continued)

Primary Examiner — Mina Haghighatian

(57) ABSTRACT

The present invention provides a composition comprising a biologically pure culture of a *Paenibacillus* sp. strain comprising a mutant DegU lacking a functional receiver domain or a functional DNA binding domain and/or a mutant DegS lacking a functional single binding domain or a functional ATPase domain with decreased viscosity in a liquid culture. Also provided is a method of identifying a *Paenibacillus* sp. mutant derivative strain with decreased viscosity in a liquid culture compared to a *Paenibacillus* sp. parental strain with a visual screen for mutant isolates with a non-mucoid morphology.

18 Claims, 15 Drawing Sheets

Specification includes a Sequence Listing.

(56) References Cited

OTHER PUBLICATIONS

Li, O., et al., "Supplementary Material: Identification ad Characterization of Six Glycosyltransferases Involved in the Biosynthesis of a New Bacterial Exopolysaccharide in Paenibacillus elgii," Applied Microbiology and Biotechnology, Dec. 3, 2017, vol. 102, No. 3, pp. 1357-1366.

Liang, T-W., et al. "Recent Advances in Exopolysaccharides from *Paenibacillus spp.*: Production, Isolation, Structure, and Bioactivities," Marine Drugs, 2015, vol. 13, pp. 1847-1863.

Raza, W., et al., "Optimization, Purification, Characterization and Antioxidant Activity of an Extracellular Polysaccharide Produced by Paenibacillus polymyxa SQR-21," Bioresource Technology, 2011, vol. 102, pp. 6095-6103.

Shimane et al., "Mutational Analysis of the Helix-Turn-Helix Region of Bacillus subtilis Response Regulator DegU, and Identification of cis-Acting Sequences for DegU in the aprE and comK Promoters," J. Biochem., 2004, vol. 136, No. 3, pp. 387-397.

Verhamme, D.T., et al., "DegU Co-ordinates Multicellular Behaviour Exhibited by Bacillus subtilis," Molecular Biology, Jun. 11, 2007, vol. 65, No. 2, pp. 554-568.

Xu, Z., et al., "Enhanced Control of Cucumber Wilt Disease by Bacillus amyloliquefaciens SQR9 by Altering the Regulation of Its DegU Phosphorylation," Applied and Environmental Microbiology, Feb. 28, 2014, vol. 80, No. 9, pp. 2941-2950.

RecName: Full=Signal transduction histidine-protein kinase/phosphatase DesS {Eco: 0000256|PIRNR: PIRNR003169}; EC=2.7.13.3 {ECO: 0000256|PIRNR: PIRNR003169}; EC=3.1.3.- {ECO: 0000256|PIRNR: PIRNR003169}; XP002792230, retrieved from EBI Accession No. UNIPROT: E0IEE5, Feb. 28, 2018, entry version 41; sequence.

Subname: Full=DNA-binding Response Regulator {ECO: 0000313|EMBL: 0AB35525.1}; XP002792229, retrieved from EBI Accession No. UNIPROT: A0A168EW51, Feb. 28, 2018, entry version 14; sequence.

International Search Report and Written Opinion of the International Searching Authority for PCT International Patent Application No. PCT/US2019/031264, dated Jul. 10, 2019, 24 pages.

Eastman, et al., "Comparative and genetic analysis of the four sequenced Paenibacillus polymyxa genomes reveals a diverse metabolism and conservation of genes relevant to plant-growth promotion and competitiveness", BMC Genomics 2014, 15:851.

* cited by examiner

FIG. 6B

```
B. subtilis 168 DegU    1  MTK--------VNIVIVIDDHQLFREGVKRILDFEPTFEVVAEGDGDEAAR         43
NRRLB-50972 DegU        1  MENQEISNAPIKVLLADDHQLFREGLKRILNMEDDIEVIGECGDGIQVLE         50

Receiver Domain

B. subtilis 168 DegU   44  IVEHYHPDVVIMDINMPNVNGVEATKQLVELYPESKVIILSIHDDENYVT         93
NRRLB-50972 DegU       51  FCNVEKPDIVLMDINMPIENGVEATEKLREMFPDVKVIILSIHDDESYVF        100

B. subtilis 168 DegU   94  HALKTGARGYLLKEMDADTLIEAVKVVAEGGSYLHPKVTHNLVNEFRRLA        143
NRRLB-50972 DegU      101  ETLRKGANGYLLKDMEAESLINAIRSVHEGYAFIHPKVTGKLIQQLRRMT        150
                                                    △1

B. subtilis 168 DegU  144  ---TSGVSA--HPQHEVYPEIRRPLHILTRRECEVLQMLADGKSNRGIGE        188
NRRLB-50972 DegU      151  YLNETGAMAEGHTKEAGVKFVAGENNPLTRREAEVLRLMAEGKSNKMIGE        200

DNA Binding Domain

B. subtilis 168 DegU  189  SLFISEKTVKNHVSNILQKMNVNDRTQAVVVAIKNGWVEMR                 229
NRRLB-50972 DegU      201  YLFISEKTVKNHVSSILQKMEVDDRTQAVINSIKYGWVTL-                 240
                                                   △2                  △3
```

| | | | NRRL B-67306, Strain C |
|---|---|---|---|
| 1 | G109D | Tiny, hydrophobic to negative charge | Strain T |
| 2 | Q218* | Premature stop | Strain B |
| 3 | A228T | Hydrophobic to polar | |

FIG. 6C

```
B. subtilis 168 DegS      1 MNKTKMDSKVLD SILMKMLKTVDGSKDEVFQIGEQSRQQYEQLVEELKQI   50
NRRLB-50972 DegS          1 ---VDFQADIIDRVIKNAIQVMENSKYQMFEILDTARTELITLNQELQSV  47
                                        Single Binding Domain B. subtilis 168 DegS     51 KQQVYEVIELGDKLEVQTRHARNRLSEVSRNFHRFSEEEIRNAYEKAHKL  100
NRRLB-50972 DegS         48 LKETAETIEKVDQLEMNYRRSRIRLTEVSRDFVRYSEEDIKQAYEKATQL   97

B. subtilis 168 DegS    101 QVELTMIQQREKQLRERRDDLERRLLGLQEIIERSESLVSQITVVLNYLN  150
NRRLB-50972 DegS         98 QIDVMIFREKEMYLKARRDDLQKRAKSVEASVERAETIGSQMGVVLEYLS  147
                           △1

B. subtilis 168 DegS    151 QDLREVGLLLADAQAKQD FGLRIIEAQEE ERKRVSREIHDGPAQMLANVM  200
NRRLB-50972 DegS        148 GELGQVTRIIESAKNRQFIGLKIILAQEEERKRISREIHDGPAQLLAHLV  197
                                        Phosphoacceptor Domain B. subtilis 168 DegS    201 MRSELIERIFRDRGAEDGFQEIKNLRQNVRNALYEVRRIIYDLRPMAL DD  250
NRRLB-50972 DegS        198 LRTEIVERMIAKQEFKMVQDEIVDLKKQVRSSLEEMRKVIFNLRPMALDD  247

B. subtilis 168 DegS    251 LGLIPTLRKYLYTEEYNGKVKIHFQCIGETEDQRLAPQF EVALFRLAQE   300
NRRLB-50972 DegS        248 LGLVPTLRKYVQDFEE-KTKIRSLFETRG--KEHRLSSAMEAAIYRLIQE  294
                                                                        △2
                                        ATPase Domain B. subtilis 168 DegS    301 AVSNALKHSESEEITVKVEITKDFVILMIKDNGKGF--DLKEAKEKNKS  348
NRRLB-50972 DegS        295 ALTNAAKHAYPTYVLVEITYQAQLVKIVVQDNGLGFKPELFQQKSKDHGH  344

B. subtilis 168 DegS    349 FGLLGMKERVDLLEGTMTIDSKIGLGTFIMIKVPLSL------  385
NRRLB-50972 DegS        345 FGLIGMREVELLEGRMEIESAENQGTKIVIHIPTNVEKGKE    386
```

| | | | |
|---|---|---|---|
| 1 | L99F | Aliphatic to aromatic | Strain T |
| 2 | E294K | Negative to positive charge | NRRL B-67304 |

MUTANTS OF PAENIBACILLUS AND METHODS FOR THEIR USE

CROSS REFERENCE TO RELATED APPLICATIONS

The present application is a 35 U.S.C. § 371 national phase entry of International Application No. PCT/US2019/031264, filed May 8, 2019, which claims the benefit under 35 U.S.C. § 119 of U.S. Provisional Patent Application No. 62/671,067, filed May 14, 2018, the entire contents of which are hereby incorporated herein in their entirety by reference.

The official copy of the sequence listing is submitted electronically via EFS-Web as an ASCII-formatted sequence listing with a file named "BCS169009_WO_ST25.txt" created on Apr. 30, 2019, and having a size of 29 kilobytes, and is filed concurrently with the specification. The sequence listing contained in this ASCII-formatted document is part of the specification and is herein incorporated by reference in its entirety.

TECHNICAL FIELD

The present invention relates to the field of bacterial strains and their ability to control plant diseases. In particular, the present invention is directed to *Paenibacillus* sp. strains with relatively high levels of antifungal activity and reduced viscosity facilitating downstream processing and concentration of whole broth products of the strains.

BACKGROUND

*Paenibacillus* is a genus of low GC-content, endospore-forming, Gram-positive bacteria (Firmicutes). Bacteria belonging to this genus are prolific producers of industrially-relevant extracellular enzymes and antimicrobial substances, including non-ribosomal peptide classes like fusaricidin and polymyxin. Fusaricidins are known to have antimicrobial activity against various plant-pathogenic fungi and bacteria.

Many *Paenibacillus* species are prolific producers of exopolysaccharides (EPS). Microbial EPS are water-soluble biopolymers which are attached to the cell surface and released into the extracellular medium. Due to their physicochemical and rheological properties these polymers have found commercial use as thickening agents in a wide range of industries including the food, feed, packaging, cosmetics and pharmaceutical industries. The production of EPS results in increased viscosity of whole broth samples, in particular, as a result of high molecular weight species. Increased broth viscosity presents issues for bioreactor growth and downstream processing of broth material intended for live microbial whole broth products. Costly and work-intensive procedures can be required to remove the EPS from large-scale fermentation broth cultures before further processing.

There is a need for methods to produce and identify *Paenibacillus* sp. strains with enhanced fungicidal activity and processability with reduced viscosity and higher levels of fusaricidins and fusaricidin-like compounds.

SUMMARY

The present invention is directed to a strategy to enhance the fungicidal activity and processability of a *Paenibacillus* sp. strain and mutant derivatives thereof. A strain improvement strategy was devised to enhance the production of fusaricidins through sequential rounds of chemical treatment and high throughput screening. Furthermore, a visual screen was developed to reduce the viscosity of fermentation broth cultures to improve large-scale growth and downstream processing of fungicidal mutant derivatives of *Paenibacillus* sp. strains. Several *Paenibacillus* sp. strains with improved fungicidal and processing characteristics were generated and characterized.

In some embodiments, the present invention relates to a composition comprising a biologically pure culture of a *Paenibacillus* sp. strain comprising a mutant DegU lacking a functional receiver domain or a functional DNA binding domain and/or a mutant DegS lacking a functional single binding domain or a functional ATPase domain, wherein the mutant DegU and/or the mutant DegS result in a liquid culture of the *Paenibacillus* sp. strain with decreased viscosity compared to a liquid culture of a *Paenibacillus* sp. strain comprising a wild-type DegU and a wild-type DegS.

In certain aspects, the mutant DegU and/or the mutant DegS inhibit the formation of colonies of the *Paenibacillus* sp. strain with a mucoid morphology.

In one embodiment, the mutant DegU and/or the mutant DegS is a knockout or is truncated as a result of a premature stop codon. In certain aspects, the premature stop codon results in a mutant DegU truncated at position 218 numbered by correspondence with the amino acid sequence of SEQ ID NO: 2.

In other embodiments, the mutant DegU comprises an amino acid substitution of a small residue to an acidic residue at position 109 numbered by correspondence with the amino acid sequence of SEQ ID NO: 2; and/or a small residue to a polar residue at position 228 numbered by correspondence with the amino acid sequence of SEQ ID NO: 2; and/or an acidic residue to a polar residue at position 63 numbered by correspondence with the amino acid sequence of SEQ ID NO: 2; and/or a polar residue to a small residue at position 195 numbered by correspondence with the amino acid sequence of SEQ ID NO: 2; and/or a hydrophobic residue to a small residue at position 204 numbered by correspondence with the amino acid sequence of SEQ ID NO: 2; and/or a polar residue to a small residue at position 208 numbered by correspondence with the amino acid sequence of SEQ ID NO: 2; and/or a basic residue to a small residue at position 212 numbered by correspondence with the amino acid sequence of SEQ ID NO: 2; and/or a hydrophobic residue to a small residue at position 217 numbered by correspondence with the amino acid sequence of SEQ ID NO: 2; and/or a basic residue to a small residue at position 207 numbered by correspondence with the amino acid sequence of SEQ ID NO: 2; and/or a polar residue to a small residue at position 211 numbered by correspondence with the amino acid sequence of SEQ ID NO: 2; and/or a polar residue to a small residue at position 214 numbered by correspondence with the amino acid sequence of SEQ ID NO: 2.

In one aspect, the mutant DegU comprises SEQ ID NO: 2 with an amino acid substitution of G109D and/or A228T and/or D63N and/or N195A and/or I204A and/or T208A and/or H212A and/or L217A and/or K2017A and/or N211A and/or S214A; or a variant thereof having a conservative amino acid substitution.

In another aspect, the mutant DegS comprises an amino acid substitution of a hydrophobic residue to an aromatic residue at position 99 numbered by correspondence with the amino acid sequence of SEQ ID NO: 4 and/or an acidic residue to a basic residue at position 294 numbered by correspondence with the amino acid sequence of SEQ ID NO: 4; and/or a polar residue to a small residue at position 73 numbered by correspondence with the amino acid sequence of SEQ ID NO: 4; and/or a small residue to a hydrophobic residue at position 190 numbered by correspondence with the amino acid sequence of SEQ ID NO: 4.

In one embodiment, the mutant DegS comprises SEQ ID NO: 4 with an amino acid substitution of L99F and/or E294K and/or T73A and/or A190V; or a variant thereof having a conservative amino acid substitution.

In some embodiments, the *Paenibacillus* sp. strain is a mutagenized derivative strain and demonstrates increased fusaricidin levels compared to a non-mutagenized parental strain. In other embodiments, the *Paenibacillus* sp. strain is a mutagenized derivative strain and demonstrates decreased amylase expression and/or enzymatic activity compared to a non-mutagenized parental strain.

In certain aspects, the decreased amylase expression and/or enzymatic activity occurs with an alpha-amylase protein comprising a sequence with greater than about 90% sequence identity to SEQ ID NO: 9 or SEQ ID NO: 10. In other aspects, the decreased amylase expression and/or enzymatic activity occurs with an alpha-amylase protein comprising a sequence with greater than about 95% sequence identity, greater than about 96% sequence identity, greater than about 97% sequence identity, greater than about 98% sequence identity, or greater than about 99% sequence identity to SEQ ID NO: 9 or SEQ ID NO: 10. In one embodiment, the alpha-amylase protein comprises SEQ ID NO: 9. In another embodiment, the alpha-amylase protein consists of SEQ ID NO: 9. In one embodiment, the alpha-amylase protein comprises SEQ ID NO: 10. In another embodiment, the alpha-amylase protein consists of SEQ ID NO: 10.

In some instances, the non-mutagenized parental strain is *Paenibacillus* sp. strain NRRL B-50972 or *Paenibacillus* sp. strain NRRL B-67129. In other instances, the non-mutagenized parental strain is *Paenibacillus* sp. strain NRRL B-50972, *Paenibacillus* sp. strain NRRL B-67129, *Paenibacillus* sp. strain NRRL B-67304, *Paenibacillus* sp. strain NRRL B-67306, or *Paenibacillus* sp. strain NRRL B-67615.

In one aspect, the *Paenibacillus* sp. strain is *Paenibacillus* sp. strain NRRL B-67304, *Paenibacillus* sp. strain NRRL B-67306, *Paenibacillus* sp. strain NRRL B-67615, or a fungicidal mutant strain thereof.

In another aspect, the composition comprises a fermentation product of *Paenibacillus* sp. strain NRRL B-67304, *Paenibacillus* sp. strain NRRL B-67306, *Paenibacillus* sp. strain NRRL B-67615, or a fungicidal mutant strain thereof.

In certain embodiments, the fungicidal mutant strain has a genomic sequence with greater than about 90% sequence identity to *Paenibacillus* sp. strain NRRL B-67304, *Paenibacillus* sp. strain NRRL B-67306, or *Paenibacillus* sp. strain NRRL B-67615.

In other embodiments, the present invention relates to a method of identifying a *Paenibacillus* sp. mutant derivative strain with decreased viscosity in a liquid culture compared to a *Paenibacillus* sp. parental strain, the method comprising: mutagenizing the *Paenibacillus* sp. parental strain to produce mutant isolates; culturing the mutant isolates and the *Paenibacillus* sp. parental strain on a solid medium comprising a sugar at a concentration of between about 1% (w/v) and about 40% (w/v), wherein the *Paenibacillus* sp. parental strain has a mucoid morphology on the solid medium; and visually screening the mutant isolates on the solid medium to identify a *Paenibacillus* sp. mutant derivative strain with a non-mucoid morphology indicative of decreased viscosity in a liquid culture.

In one aspect, the sugar in the solid medium is at a concentration of between about 5% (w/v) and about 20% (w/v). In another aspect, the sugar is selected from the group consisting of sucrose, starch, maltodextrin, corn syrup solids, fructose, glucose, galactose, lactose, maltose, xylose, xylitol, inulin, sorbitol, fucose, molasses, and combinations thereof.

In certain embodiments, the carbon to nitrogen ratio in the solid medium is between about 10:1 and about 1000:1. In one aspect, the solid medium further comprises agar, agarose, and/or gelatin. In a particular aspect, the solid medium is solid agar medium.

In other embodiments, the method further comprises culturing the *Paenibacillus* sp. mutant derivative strain in a liquid medium to produce a liquid culture; and measuring viscosity and/or packed cell volume of the liquid culture to confirm the decreased viscosity of the *Paenibacillus* sp. mutant derivative strain compared to the *Paenibacillus* sp. parental strain.

In certain embodiments, the method further comprises sequencing degU and/or degS in the *Paenibacillus* sp. mutant derivative strain to identify a sequence encoding a mutant DegU lacking a functional receiver domain or a functional DNA binding domain and/or a mutant DegS lacking a functional single binding domain or a functional ATPase domain.

In other embodiments, the method further comprises determining expression and/or enzymatic activity of an amylase in the *Paenibacillus* sp. mutant derivative strain and the *Paenibacillus* sp. parental strain to determine if the expression and/or enzymatic activity is decreased in the *Paenibacillus* sp. mutant derivative strain. In certain aspects, the expression and/or enzymatic activity of the amylase in the *Paenibacillus* sp. mutant derivative strain is less than about 90%, less than about 80%, less than about 70%, less than about 60%, less than about 50%, less than about 40%, less than about 30%, less than about 20%, or less than about 10% that of the *Paenibacillus* sp. parental strain. In other aspects, the expression and/or enzymatic activity of the amylase in the *Paenibacillus* sp. mutant derivative strain is between about 1% and about 90%, between about 10% and about 90%, between about 10% and about 80%, between about 10% and about 70%, between about 10% and 60%, between about 20% and 90%, between about 20% and 80%, between about 20% and 70%, or between about 20% and 60% that of the *Paenibacillus* sp. parental strain.

In some embodiments, the decreased amylase expression and/or enzymatic activity occurs with an alpha-amylase protein comprising a sequence with greater than about 90% sequence identity to SEQ ID NO: 9 or SEQ ID NO: 10.

In one embodiment, the method further comprises quantifying fusaricidin levels in the mutant isolates to identify mutant isolates with increased fusaricidin levels compared to the *Paenibacillus* sp. parental strain.

In certain embodiments, the *Paenibacillus* sp. strain is *P. agarexedens, P. agaridevorans, P. alginolyticus, P. alkaliterrae, P. alvei, P. amylolyticus, P. anaericanus, P. antarcticus, P. assamensis, P. azoreducens, P. azotofixans, P. barcinonensis, P. borealis, P. brasiliensis, P. brassicae, P. campinasensis, P. chinjuensis, P. chitinolyticus, P. chondroitinus, P. cineris, P. cookie, P. curdlanolyticus, P. daejeonensis, P. dendritiformis, P. durum, P. ehimensis, P. elgii, P. favisporus, P. glucanolyticus, P. glycanilyticus, P. gordonae, P. graminis, P. granivorans, P. hodogayensis, P. illinoisensis, P. jamilae, P. kobensis, P. koleovorans, P. koreensis, P. kribbensis, P. lactis, P. larvae, P. lautus, P. lentimorbus, P. macerans, P. macquariensis, P. massiliensis,*

*P. mendelii, P. motobuensis, P. naphthalenovorans, P. nematophilus, P. nov.* spec. *epiphyticus, P. odorifer, P. pabuli, P. peoriae, P. phoenicis, P. phyllosphaerae, P. polymyxa, P. polymyxa* ssp. *polymyxa, P. polymyxa* ssp. *plantarum, P. popilliae, P. pulvifaciens, P. rhizosphaerae, P. sanguinis, P. stellifer, P. taichungensis, P. terrae, P. thiaminolyticus, P. timonensis, P. tylopili, P. turicensis, P. validus, P. vortex, P. vulneris, P. wynnii* or *P. xylanilyticus*.

In another embodiment, the *Paenibacillus* sp. strain is *Paenibacillus polymyxa, Paenibacillus polymyxa* ssp. *polymyxa, Paenibacillus polymyxa* ssp. *plantarum, Paenibacillus nov.* spec. *epiphyticus, Paenibacillus terrae, Paenibacillus macerans*, or *Paenibacillus alvei*. In yet another embodiment, the *Paenibacillus* sp. strain is *Paenibacillus terrae*.

In certain aspects, the *Paenibacillus* sp. strain is a fusaricidin-producing *Paenibacillus* sp. strain.

Examples of fusaricidin-producing *Paenibacillus* sp. strains include but are not limited to *Paenibacillus polymyxa, Paenibacillus polymyxa* ssp. *polymyxa, Paenibacillus polymyxa* ssp. *plantarum, Paenibacillus nov.* spec. *epiphyticus, Paenibacillus terrae, Paenibacillus macerans*, and *Paenibacillus alvei*.

In yet other embodiments, the present invention relates to a method for generating a *Paenibacillus* sp. mutant derivative strain with decreased viscosity in a liquid culture compared to a *Paenibacillus* sp. parental strain, the method comprising: mutagenizing the *Paenibacillus* sp. parental strain to create mutant isolates; culturing the mutant isolates and the *Paenibacillus* sp. parental strain on a solid medium comprising a sugar at a concentration of between about 1% (w/v) and about 40% (w/v), wherein the *Paenibacillus* sp. parental strain has a mucoid morphology on the solid medium; visually screening the mutant isolates on the solid medium to identify a *Paenibacillus* sp. mutant derivative strain with a non-mucoid morphology indicative of decreased viscosity in a liquid culture; and producing a fermentation product of the identified *Paenibacillus* sp. mutant derivative strain. In one aspect, the mutagenizing comprises chemical mutagenesis of the *Paenibacillus* sp. parental strain.

In one aspect, the present invention provides a fermentation product comprising the *Paenibacillus* sp. mutant derivative strain identified with the disclosed methods. In another aspect, the fermentation product comprises a broth concentrate of a whole broth from the *Paenibacillus* sp. mutant derivative strain to increase its fungicidal and/or bactericidal activity.

In some embodiments, the present invention relates to a method of treating a plant to control a disease, wherein the method comprises applying an effective amount of a composition disclosed herein or fermentation product disclosed herein to the plant, to a part of the plant and/or to a locus of the plant.

In one embodiment, the composition is applied at about $1 \times 10^4$ to about $1 \times 10^{14}$ colony forming units (CFU) per hectare or at about 0.1 kg to about 20 kg fermentation solids per hectare.

In some aspects, the plant disease is caused by a fungus. In one aspect, the plant disease is powdery mildew or downy mildew. In another aspect, the fungus is selected from the group consisting of *Alternaria alternata, Alternaria solani, Botrytis cinerea, Colletotrichum lagenarium, Erysiphe necator, Fusarium culmorum, Phaeosphaeria nodorum, Zymoseptoria tritici, Phytophthora cryptogea, Phytophthora infestans, Plasmopara viticola, Podosphaera leucotricha, Pseudoperonospora cubensis, Pythium ultimum, Magnaporthe oryzae, Sphaerotheca fuliginea, Thanatephorus cucumeris, Ustilago segetum* var. *avenae, Uromyces appendiculatus*, and *Puccinia triticina*.

In other aspects, the plant disease is caused by bacteria. In a certain aspect, the bacteria are selected from the group consisting of *Xanthomonas campestris, Pseudomonas syringae*, and *Erwinia carotovora*.

In yet other embodiments, the present invention relates to the use of a composition disclosed herein or a fermentation product disclosed herein for controlling a phytopathogenic organism in useful plants.

BRIEF DESCRIPTION OF THE DRAWINGS

FIG. 6B depicts an alignment of the DegU amino acid sequences from *Bacillus subtilis* strain 168 (SEQ ID NO: 1) and *Paenibacillus* sp. strain NRRL B-50972 (SEQ ID NO: 2) with SNPs identified in the receiver and DNA binding domains of the protein. FIG. 6C depicts an alignment of the DegS amino acid sequences from *Bacillus subtilis* strain 168 (SEQ ID NO: 3) and *Paenibacillus* sp. strain NRRL B-50972 (SEQ ID NO: 4) with SNPs identified in the single binding and ATPase domains of the protein.

DETAILED DESCRIPTION

Figure 1:
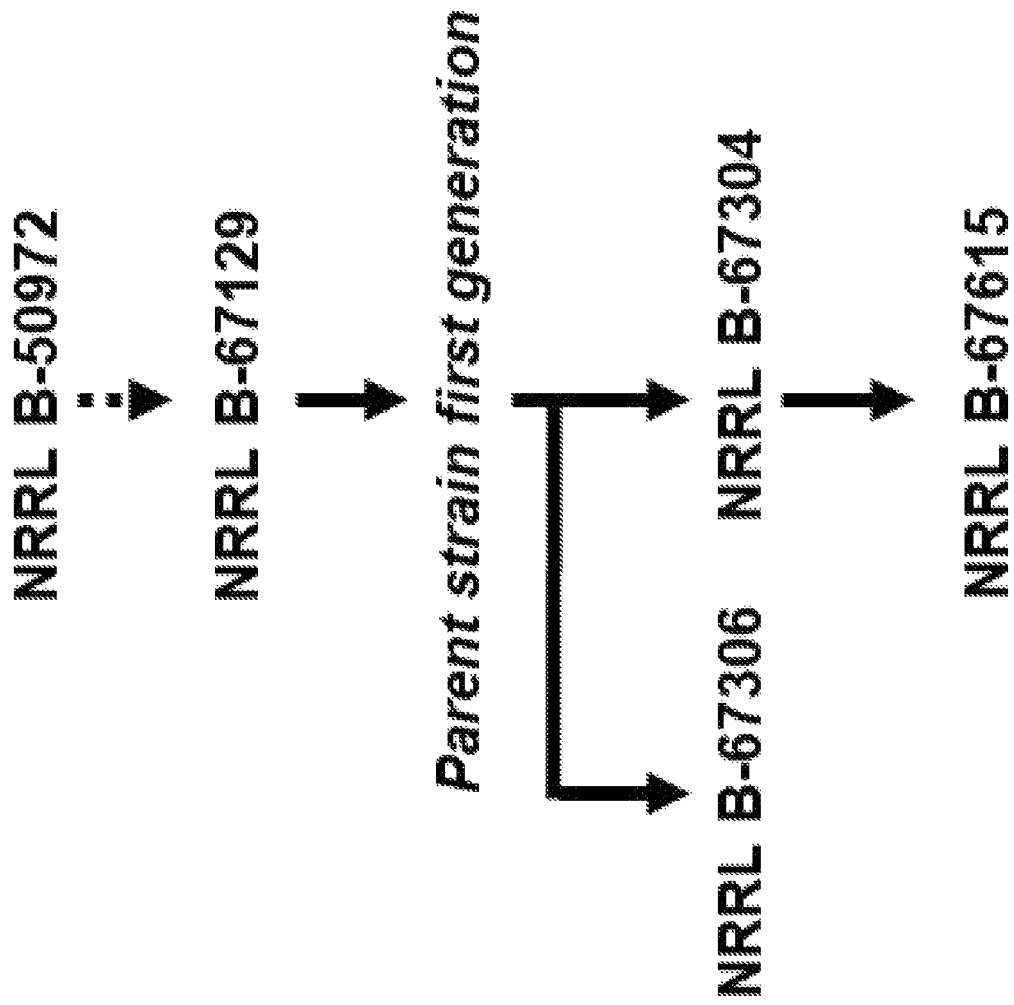
FIG. 1 depicts the strain lineage from *Paenibacillus* sp. strain NRRL B-50972 of *Paenibacillus* sp. strain NRRL B-67129, *Paenibacillus* sp. strain NRRL B-67304, *Paenibacillus* sp. strain NRRL B-67306, and *Paenibacillus* sp. strain NRRL B-67615.

The microorganisms and particular strains described herein, unless specifically noted otherwise, are all separated from nature and grown under artificial conditions such as in shake flask cultures or through scaled-up manufacturing processes, such as in bioreactors to maximize bioactive metabolite production, for example. Growth under such conditions leads to strain "domestication." Generally, such a "domesticated" strain differs from its counterparts found in nature in that it is cultured as a homogenous population that is not subject to the selection pressures found in the natural environment but rather to artificial selection pressures.

Microorganisms of the invention, or cultures or isolates thereof, may be described to be in an "isolated" or "biologically pure" form. These terms are intended to mean that the microorganisms have been separated from an environment or one or more constituents, cellular or otherwise, which they may be associated with if found in nature or otherwise. The terms "isolated" or "biologically pure" should not be taken to indicate the extent to which the microorganisms have been purified. However, in one embodiment the isolates or cultures of the microorganisms contain a predominance of the microorganisms of the invention.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein a "basic residue" is arginine, lysine or histidine; an "acidic residue" is glutamic acid or aspartic acid; a "polar residue" is serine, threonine, cysteine, glutamine, or asparagine; a "hydrophobic residue" is methionine, proline, leucine, isoleucine or valine; an "aromatic residue" is phenylalanine, tryptophan or tyrosine; and a "small residue" is glycine or alanine.

In some embodiments, the *Paenibacillus* sp. strain comprising a mutant DegU and/or a mutant DegS produces a liquid culture with decreased viscosity compared to a liquid culture of a *Paenibacillus* sp. strain comprising a wild-type DegU and a wild-type DegS. In certain aspects, decreased viscosity is measured by growing the *Paenibacillus* sp. strain comprising a mutant DegU and/or a mutant DegS and the *Paenibacillus* sp. strain comprising a wild-type DegU and a wild-type DegS separately in the same liquid culture medium until stationary phase and measuring the viscosity of each liquid culture. Viscosity can be measured by any method known in the art including the method outlined in Example 2. Examples of wild-type DegU and wild-type DegS include the amino acid sequences presented as SEQ ID NO: 1 and SEQ ID NO: 2 and as SEQ ID NO: 3 and SEQ ID NO: 4, respectively.

Figure 3:
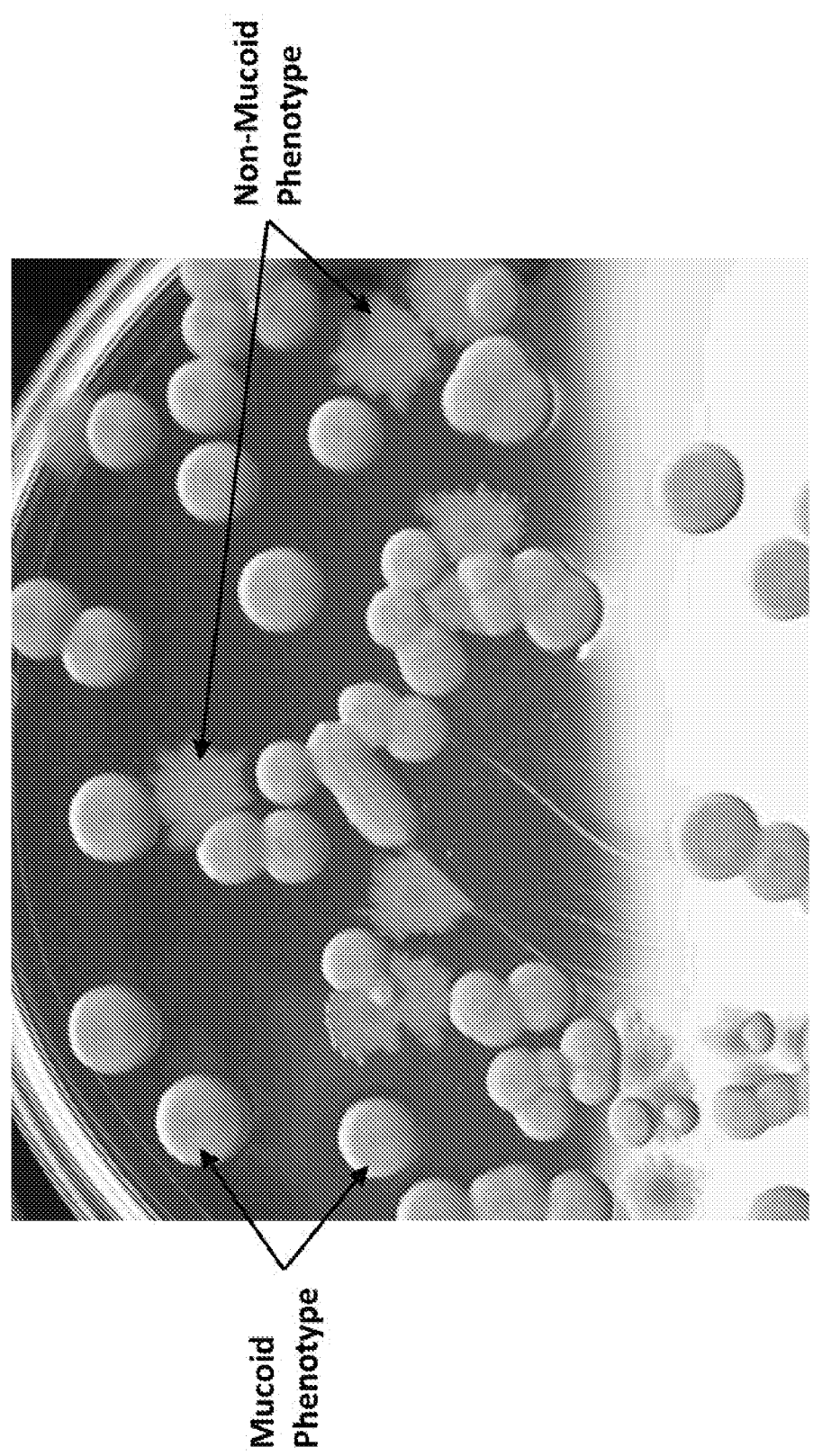
FIG. 3 depicts colonies from a mixed population of a mucoid and non-mucoid isolates on solid agar medium supplemented with sucrose.

As used herein, the terms "mucoid" and "mucoid morphology" refer to a phenotype of a microbial colony where the colony has well-defined, round edges and a shiny appearance under a light microscope. In addition, microbial colonies with a mucoid morphology tend to be taller and rounder three-dimensionally. Examples of mucoid colonies are presented in FIG. 3.

As used herein, the terms "non-mucoid" and "non-mucoid morphology" refer to a phenotype of a microbial colony where the colony has less distinct, randomly shaped edges and a dull appearance under a light microscope. Non-mucoid colonies tend to be flatter three-dimensionally. Examples of non-mucoid colonies are also presented in FIG. 3.

The mucoid morphology and the non-mucoid morphology are more easily distinguished on solid agar medium comprising a sugar at a concentration of between about 1% (w/v) and about 40% (w/v). In certain aspects, the sugar concentration is between about 1% (w/v) and about 30% (w/v), between about 1% (w/v) and about 20% (w/v), between about 5% (w/v) and about 40% (w/v), between about 5% (w/v) and about 30% (w/v), or between about 5% (w/v) and about 20% (w/v). In one aspect, the sugar in the solid agar medium is at a concentration of between about 5% (w/v) and about 20% (w/v).

In some embodiments, the carbon to nitrogen ratio in the solid medium is between about 10:1 and about 1000:1, between about 10:1 and about 750:1, between about 10:1 and about 500:1, between about 10:1 and about 250:1, between about 10:1 and about 100:1, between about 10:1 and about 75:1, between about 10:1 and about 50:1, between about 10:1 and about 25:1, between about 1:1 and about 100:1, between about 1:1 and about 75:1, between about 1:1 and about 50:1, or between about 1:1 and about 25:1. In another aspect, the carbon to nitrogen ratio in the solid medium between about 10:1 and about 1000:1, between about 10:1 and about 750:1, between about 10:1 and about 500:1, between about 10:1 and about 250:1, between about 10:1 and about 100:1. In one aspect, the carbon to nitrogen ratio in the solid medium is between about 10:1 and about 1000:1.

In one embodiment, the solid medium and/or liquid medium used in the disclosed methods for identifying a *Paenibacillus* sp. mutant derivative strain with decreased viscosity in a liquid culture compared to a *Paenibacillus* sp. parental strain comprises any sugar that supports growth of *Paenibacillus* sp. cells.

In certain aspects, the sugar is selected from the group consisting of sucrose, maltodextrin, starch, corn syrup solids, fructose, glucose, galactose, lactose, maltose, xylose, xylitol, inulin, sorbitol, fucose, molasses, and combinations thereof. In another aspect, the sugar is selected from the group consisting of sucrose, starch, corn syrup solids, maltodextrin, fructose, glucose, galactose, lactose, maltose, and combinations thereof. In another aspect, the sugar is selected from the group consisting of sucrose, maltodextrin, fructose, and combinations thereof. In yet another aspect, the sugar is sucrose or maltodextrin.

In some embodiments, the present invention relates to a method of of identifying a *Paenibacillus* sp. mutant derivative strain with decreased viscosity in a liquid culture compared to a *Paenibacillus* sp. parental strain using a visual screen. As used herein, the terms "visual screen" and "visually screening" refer to any process whether carried out manually or automatically with a machine or robot to analyze the size, shape, and/or luster (i.e., shininess) of microbial colonies grown on solid medium. In some aspects, the solid medium is a solid agar medium.

In other embodiments, the present invention relates to a method of identifying a *Paenibacillus* sp. mutant derivative strain with decreased viscosity in a liquid culture compared to a *Paenibacillus* sp. parental strain, the method comprising: mutagenizing the *Paenibacillus* sp. parental strain to produce mutant isolates; culturing the mutant isolates and the *Paenibacillus* sp. parental strain in a liquid medium comprising a sugar at a concentration of between about 1% (w/v) and about 40% (w/v); and measuring the visocity and/or packed cell volume of the mutant isolates in the liquid medium to identify a *Paenibacillus* sp. mutant derivative strain with a decreased viscosity in a liquid culture compared to the *Paenibacillus* sp. parental strain.

*Paenibacillus* sp. strain NRRL B-50972 and *Paenibacillus* sp. strain NRRL B-67129 were previously identified as producers of a unique group of fusaricidins and fusaricidin-like compounds with broad spectrum antifungal activity (WO 2016/154297).

In one aspect, the *Paenibacillus* sp. strain of the present invention is selected from any one of the following: *P. agarexedens, P. agaridevorans, P. alginolyticus, P. alkaliterrae, P. alvei, P. amylolyticus, P. anaericanus, P. antarcticus, P. assamensis, P. azoreducens, P. azotofixans, P. barcinonensis, P. borealis, P. brasiliensis, P. brassicae, P. campinasensis, P. chinjuensis, P. chitinolyticus, P. chondroitinus, P. cineris, P. cookie, P. curdlanolyticus, P. daejeonensis, P. dendritiformis, P. durum, P. ehimensis, P. elgii, P. favisporus, P. glucanolyticus, P. glycanilyticus, P. gordonae, P. graminis, P. granivorans, P. hodogayensis, P. illinoisensis, P. jamilae, P. kobensis, P. koleovorans, P. koreensis, P. kribbensis, P. lactis, P. larvae, P. lautus, P. lentimorbus, P. macerans, P. macquariensis, P. massiliensis, P. mendelii, P. motobuensis, P. naphthalenovorans, P. nematophilus, P. nov.* spec. *epiphyticus, P. odorifer, P. pabuli, P. peoriae, P. phoenicis, P. phyllosphaerae, P. polymyxa, P. polymyxa* ssp. *polymyxa, P. polymyxa* ssp. *plantarum, P. popilliae, P. pulvifaciens, P. rhizosphaerae, P. sanguinis, P. stellifer, P. taichungensis, P. terrae, P. thiaminolyticus, P. timonensis, P. tylopili, P. turicensis, P. validus, P. vortex, P. vulneris, P. wynnii* and *P. xylanilyticus.*

In another aspect, the *Paenibacillus* sp. strain of the present invention is selected from any one of the following: *P. terrae, P. brasilensis, P. polymyxa*, or *P. peoriae*. In one aspect, the *Paenibacillus* sp. strain of the present invention is *P. terrae.*

In one embodiment, a mutant strain of the *Paenibacillus* sp. strain NRRL B-67304, *Paenibacillus* sp. strain NRRL B-67306, or *Paenibacillus* sp. strain NRRL B-67615 is provided. The term "mutant" refers to a genetic variant derived from *Paenibacillus* sp. strain NRRL B-67304, *Paenibacillus* sp. strain NRRL B-67306, or *Paenibacillus* sp. strain NRRL B-67615. In one embodiment, the mutant has one or more or all the identifying (functional) characteristics of *Paenibacillus* sp. strain NRRL B-67304, *Paenibacillus* sp. strain NRRL B-67306, or *Paenibacillus* sp. strain NRRL B-67615. In a particular instance, the mutant or a fermentation product thereof controls (as an identifying functional characteristic) fungi, oomycetes and/or bacteria at least as well as the parent *Paenibacillus* sp. strain NRRL B-67304, *Paenibacillus* sp. strain NRRL B-67306, or *Paenibacillus* sp. strain NRRL B-67615. Such mutants may be genetic variants having a genomic sequence that has greater than about 85%, greater than about 90%, greater than about 95%, greater than about 98%, or greater than about 99% sequence identity to *Paenibacillus* sp. strain NRRL B-67304, *Paenibacillus* sp. strain NRRL B-67306, or *Paenibacillus* sp. strain NRRL B-67615. Mutants may be obtained by treating cells of *Paenibacillus* sp. strain NRRL B-67304, *Paenibacillus* sp. strain NRRL B-67306, or *Paenibacillus* sp. strain NRRL B-67615 with chemicals or irradiation or by selecting spontaneous mutants from a population of *Paenibacillus* sp. strain NRRL B-67304, *Paenibacillus* sp. strain NRRL B-67306, or *Paenibacillus* sp. strain NRRL B-67615 cells (such as phage resistant or antibiotic resistant mutants), by genome shuffling, as described below, or by other means well known to those practiced in the art.

Genome shuffling among *Paenibacillus* strains can be facilitated through the use of a process called protoplast fusion. The process begins with the formation of protoplasts from vegetative bacillary cells. The removal of peptidoglycan cell wall, typically using lysozyme and an osmotic stabilizer, results in the formation of a protoplast. This process is visible under a light microscope with the appearance of spherical cells. Addition of PEG, polyethylene glycol, then induces fusion among protoplasts, allowing genetic contents of two or more cells to come in contact facilitating recombination and genome shuffling. Fused cells then repartition and are recovered on a solid growth medium. During recovery, protoplasts rebuild peptidoglycan cell walls, transitioning back to bacillary shape. See Schaeffer, et. al., (1976) PNAS USA, vol. 73, 6:2151-2155).

The *Paenibacillus* sp. strain NRRL B-67304, *Paenibacillus* sp. strain NRRL B-67306, or *Paenibacillus* sp. strain NRRL B-67615 and mutants thereof have activity against a broad range of plant pathogens. In one aspect, the strain has activity against fungi, such as cucumber anthracnose, cucumber powdery mildew, wheat leaf rust, barley powdery mildew, *Alternaria*, and *Botrytis*; Oomycetes, such as tomato late blight, cucumber downy mildew and *brassica* downy mildew; and/or bacteria, such as *Pseudomonas, Xanthomonas*, and *Erwinia.*

In certain aspects, the mutant DegU and/or the mutant DegS characteristic of the *Paenibacillus* sp. strain comprises a conservative amino acid substitution. For example, conservative amino acid substitutions within the sequences of SEQ ID NO: 1-4 are contemplated. Examples of conservative amino acid substitutions are within the group of basic amino acids (i.e., arginine, lysine and histidine), acidic amino acids (i.e., glutamic acid and aspartic acid), polar amino acids (i.e., serine, threonine, cysteine, glutamine, and asparagine), hydrophobic amino acids (i.e., methionine, proline, leucine, isoleucine and valine), aromatic amino acids (i.e., phenylalanine, tryptophan and tyrosine), and small amino acids (i.e., glycine and alanine). Amino acid substitutions that do not generally alter specific activity are known in the art and are described, for example, in H. Neurath and R. L. Hill, 1979, The Proteins, Academic Press, New York, which is incorporated by reference herein in its entirety. Commonly occurring conservative substitutions include Val/Ile, Asp/Glu, Thr/Ser, Ala/Gly, Lys/Arg, Leu/Ile, and Leu/Val.

The present invention also encompasses methods of treating a plant to control plant diseases by administering to a plant or a plant part, such as a leaf, stem, flowers, fruit, root, or seed or by applying to a locus on which plant or plant parts grow, such as soil, the disclosed *Paenibacillus* sp. strains or mutants thereof, or cell-free preparations thereof or metabolites thereof.

In a method according to the invention a composition containing a disclosed *Paenibacillus* sp. strain or a fungicidal mutant thereof can be applied to any plant or any part of any plant grown in any type of media used to grow plants (e.g., soil, vermiculite, shredded cardboard, and water) or applied to plants or the parts of plants grown aerially, such as orchids or staghorn ferns. The composition may for instance be applied by spraying, atomizing, vaporizing, scattering, dusting, watering, squirting, sprinkling, pouring or fumigating. As already indicated above, application may be carried out at any desired location where the plant of interest is positioned, such as agricultural, horticultural, forest, plantation, orchard, nursery, organically grown crops, turfgrass and urban environments.

Compositions of the present invention can be obtained by culturing the disclosed *Paenibacillus* sp. strains or a fungicidal mutant (strain) derived therefrom according to methods well known in the art, including by using the media and other methods described in the examples below. Conventional large-scale microbial culture processes include submerged fermentation, solid state fermentation, or liquid surface culture. Towards the end of fermentation, as nutrients are depleted, cells begin the transition from growth phase to sporulation phase, such that the final product of fermentation is largely spores, metabolites and residual fermentation medium. Sporulation is part of the natural life cycle of *Paenibacillus* and is generally initiated by the cell in response to nutrient limitation. Fermentation is configured to obtain high levels of colony forming units of and to promote sporulation. The bacterial cells, spores and metabolites in culture media resulting from fermentation may be used directly or concentrated by conventional industrial methods, such as centrifugation, tangential-flow filtration, depth filtration, and evaporation.

Compositions of the present invention include fermentation products. In some embodiments, the concentrated fermentation broth is washed, for example, via a diafiltration process, to remove residual fermentation broth and metabolites. The term "broth concentrate," as used herein, refers to whole broth (fermentation broth) that has been concentrated by conventional industrial methods, as described above, but remains in liquid form. The term "fermentation solid," as used herein, refers to the solid material that remains after the fermentation broth is dried. The term "fermentation product," as used herein, refers to whole broth, broth concentrate and/or fermentation solids. Compositions of the present invention include fermentation products.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers, described below, may also be added post-drying.

Cell-free preparations of fermentation broth of the strains of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

In one embodiment, the fermentation product comprises at least about $1\times10^4$ colony forming units (CFU) of the microorganism (e.g., *Paenibacillus* sp. strain NRRL B-67304, *Paenibacillus* sp. strain NRRL B-67306, or *Paenibacillus* sp. strain NRRL B-67615 or a fungicidal mutant strain thereof)/mL broth. In another embodiment, the fermentation product comprises at least about $1\times10^5$ colony forming units (CFU) of the microorganism/mL broth. In another embodiment, the fermentation product comprises at least about $1\times10^6$ CFU of the microorganism/mL broth. In yet another embodiment, the fermentation product comprises at least about $1\times10^7$ CFU of the microorganism/mL broth. In another embodiment, the fermentation product comprises at least about $1\times10^8$ CFU of the microorganism/mL broth. In another embodiment, the fermentation product comprises at least about $1\times10^9$ CFU of the microorganism/mL broth. In another embodiment, the fermentation product comprises at least about $1\times10^{10}$ CFU of the microorganism/mL broth. In another embodiment, the fermentation product comprises at least about $1\times10^{11}$ CFU of the microorganis/mL broth.

The inventive compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, oil dispersion, suspo-emulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

In some embodiments, the inventive compositions are liquid formulations. Non-limiting examples of liquid formulations include suspension concentrations and oil dispersions. In other embodiments, the inventive compositions are solid formulations. Non-limiting examples of liquid formulations include freeze-dried powders and spray-dried powders.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the form of varieties, races, biotypes and genotypes.

The treatment of the plants and plant parts with the compositions according to the invention is carried out directly or by acting on the environment, habitat or storage space using customary treatment methods, for example by dipping, spraying, atomizing, misting, evaporating, dusting, fogging, scattering, foaming, painting on, spreading, injecting, drenching, trickle irrigation and, in the case of propagation material, in particular in the case of seed, furthermore by the dry seed treatment method, the wet seed treatment method, the slurry treatment method, by encrusting, by coating with one or more coats and the like. It is furthermore possible to apply the active substances by the ultra-low volume method or to inject the active substance preparation or the active substance itself into the soil.

A preferred direct treatment of the plants is the leaf application treatment, i.e., compositions according to the invention are applied to the foliage, it being possible for the treatment frequency and the application rate to be matched to the infection pressure of the pathogen in question.

In the case of systemically active compounds, the compositions according to the invention reach the plants via the root system. In this case, the treatment of the plants is effected by allowing the compositions according to the invention to act on the environment of the plant. This can be done for example by drenching, incorporating in the soil or into the nutrient solution, i.e., the location of the plant (for example the soil or hydroponic systems) is impregnated with a liquid form of the compositions according to the invention, or by soil application, i.e., the compositions according to the invention are incorporated into the location of the plants in solid form (for example in the form of granules). In the case of paddy rice cultures, this may also be done by metering the compositions according to the invention into a flooded paddy field in a solid use form (for example in the form of granules).

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term "useful plants" as used in the present context refers to crop plants which are employed as plants for obtaining foodstuffs, feedstuffs, fuels or for industrial purposes.

The useful plants which can be treated and/or improved with the compositions and methods of the present invention include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or else plants such as tobacco, nuts, coffee, aubergine, sugar cane, tea, pepper, grapevines, hops, bananas, latex plants and ornamentals, for example flowers, shrubs, deciduous trees and coniferous trees. This enumeration is no limitation.

The following plants are considered to be particularly suitable target crops for applying compositions and methods of the present invention: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., Acer sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiata, P. ponderosa, P. contorta, P. sylvestre, P. elliottii, P. montecola, P. albicaulis, P. resinosa, P. palustris, P. taeda, P. flexilis, P. jeffregi, P. baksiana, P. strobus*; from the tree species *Eucalyptus: E. grandis, E. globulus, E. camadentis, E. nitens, E. obliqua, E. regnans, E. pilularus*.

Especially preferred trees which can be improved in accordance with the method according to the invention are: from the tree species *Pinus: P. radiata, P. ponderosa, P.*

*contorta, P. sylvestre, P. strobus*; from the tree species *Eucalyptus: E. grandis, E. globulus, E. camadentis.*

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.)

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.)

Examples of warm-season turf grasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpetgrass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), blue grama (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.) Cool-season turf grasses are generally preferred for the use according to the invention. Especially preferred are bluegrass, benchgrass and redtop, fescues and ryegrasses. Bentgrass is especially preferred.

The inventive compositions have potent microbicidal activity and can be used for control of unwanted microorganisms, such as fungi and bacteria, in crop protection and in the protection of materials.

The invention also relates to a method for controlling unwanted microorganisms, characterized in that the inventive compositions are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example Blumeria species, for example *Blumeria graminis*; Podosphaera species, for example *Podosphaera leucotricha*; Sphaerotheca species, for example *Sphaerotheca fuliginea*; Uncinula species, for example Uncinula necator;

diseases caused by rust disease pathogens, for example Gymnosporangium species, for example *Gymnosporangium sabinae*; Hemileia species, for example *Hemileia vastatrix*; Phakopsora species, for example *Phakopsora pachyrhizi* and *Phakopsora meibomiae*; Puccinia species, for example *Puccinia recondite, P. triticina, P. graminis* or *P. striiformis*; Uromyces species, for example *Uromyces appendiculatus*;

diseases caused by pathogens from the group of the Oomycetes, for example Albugo species, for example *Albugo candida*; Bremia species, for example *Bremia lactucae*; Peronospora species, for example *Peronospora pisi* or *P. brassicae*; Phytophthora species, for example *Phytophthora infestans*; Plasmopara species, for example *Plasmopara viticola*; Pseudoperonospora species, for example *Pseudoperonospora humuli* or *Pseudoperonospora cubensis*; Pythium species, for example *Pythium ultimum*;

leaf blotch diseases and leaf wilt diseases caused, for example, by Alternaria species, for example *Alternaria solani*; Cercospora species, for example *Cercospora beticola*; Cladiosporium species, for example *Cladiosporium cucumerinum*; Cochliobolus species, for example *Cochliobolus sativus* (conidia form: Drechslera, Syn: Helminthosporium), *Cochliobolus miyabeanus*; Colletotrichum species, for example *Colletotrichum lindemuthanium*; Cycloconium species, for example *Cycloconium oleaginum*; Diaporthe species, for example *Diaporthe citri*; Elsinoe species, for example *Elsinoe fawcettii*; Gloeosporium species, for example *Gloeosporium laeticolor*; Glomerella species, for example *Glomerella cingulata*; Guignardia species, for example *Guignardia bidwelli*; Leptosphaeria species, for example *Leptosphaeria maculans, Leptosphaeria nodorum*; Magnaporthe species, for example *Magnaporthe grisea*; Marssonia species, for example *Marssonia coronaria*; Microdochium species, for example *Microdochium nivale*; Mycosphaerella species, for example *Mycosphaerella graminicola, M. arachidicola* and *M. fijiensis*; Phaeosphaeria species, for example *Phaeosphaeria nodorum*; Pyrenophora species, for example *Pyrenophora teres, Pyrenophora tritici* repentis; Ramularia species, for example *Ramularia collo-cygni, Ramularia areola*; Rhynchosporium species, for example *Rhynchosporium secalis*; Septoria species, for example *Septoria apii, Septoria lycopersii*; Typhula species, for example Typhula *incarnata*; Venturia species, for example Venturia *inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborn decay, mold, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by Monilinia species, for example Monilinia *laxa*;

leaf blister or leaf curl diseases caused, for example, by *Exobasidium* species, for example *Exobasidium vexans*;

Taphrina species, for example Taphrina deformans;

decline diseases of wooden plants caused, for example, by Esca disease, caused for example by *Phaemoniella clamydospora, Phaeoacremonium aleophilum* and *Fomitiporia mediterranea; Eutypa dyeback*, caused for example by *Eutypa lata; Ganoderma* diseases caused for example by *Ganoderma boninense; Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani; Helminthosporium* species, for example *Helminthosporium solani*;

Club root caused, for example, by Plasmodiophora species, for example *Plamodiophora brassicae*;

diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), Choanephora leaf blight (*Choanephora infundibulifera trispora* (Syn.)), Dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (Calonectria *crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), Mycoleptodiscus root rot (*Mycoleptodiscus terrestris*), Neocosmospora (*Neocosmospora vasinfecta*), pod and stem blight (*Diaporthe phaseolorum*), stem canker (*Diaporthe phaseolorum* var. caulivora), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive compositions, which are applied to the seed, the plant or plant parts, the fruit or the soil in which the plants grow.

The fact that the compositions are well tolerated by plants at the concentrations required for controlling plant diseases allows the treatment of above-ground parts of plants, of propagation stock and seeds, and of the soil.

According to the invention all plants and plant parts can be treated including cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods.

In certain aspects, the compositions of the present invention are applied at about $1\times10^4$ to about $1\times10^{14}$ colony forming units (CFU) per hectare, at about $1\times10^4$ to about $1\times10^{12}$ colony forming units (CFU) per hectare, at about $1\times10^4$ to about $1\times10^{10}$ colony forming units (CFU) per hectare, at about $1\times10^4$ to about $1\times10^8$ colony forming units (CFU) per hectare, at about $1\times10^6$ to about $1\times10^{14}$ colony forming units (CFU) per hectare, at about $1\times10^6$ to about $1\times10^{12}$ colony forming units (CFU) per hectare, at about $1\times10^6$ to about $1\times10^{10}$ colony forming units (CFU) per hectare, at about $1\times10^6$ to about $1\times10^8$ colony forming units (CFU) per hectare, at about $1\times10^8$ to about $1\times10^{14}$ colony forming units (CFU) per hectare, at about $1\times10^8$ to about $1\times10^{12}$ colony forming units (CFU) per hectare, or at about $1\times10^8$ to about $1\times10^{10}$ colony forming units (CFU) per hectare.

In other aspects, the compositions of the present invention are applied at about $1\times10^6$ to about $1\times10^{14}$ colony forming units (CFU) per hectare, at about $1\times10^6$ to about $1\times10^{12}$ colony forming units (CFU) per hectare, at about $1\times10^6$ to about $1\times10^{10}$ colony forming units (CFU) per hectare, at about $1\times10^6$ to about $1\times10^8$ colony forming units (CFU) per hectare. In yet other aspects, the compositions of the present invention are applied at about $1\times10^9$ to about $1\times10^{13}$ colony forming units (CFU) per hectare. In one aspect, the compositions of the present invention are applied at about $1\times10^{10}$ to about $1\times10^{12}$ colony forming units (CFU) per hectare.

In certain embodiments, the compositions of the present invention are applied at about 0.1 kg to about 20 kg fermentation solids per hectare. In some embodiments, the compositions of the present invention are applied at about 0.1 kg to about 10 kg fermentation solids per hectare. In other embodiments, the compositions of the present invention are applied at about 0.25 kg to about 7.5 kg fermentation solids per hectare. In yet other embodiments, the compositions of the present invention are applied at about 0.5 kg to about 5 kg fermentation solids per hectare. The compositions of the present invention may also be applied at about 1 kg or about 2 kg fermentation solids per hectare.

The inventive compositions, when they are well tolerated by plants, have favorable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g., canola, rapeseed), *Brassica rapa*, *B. juncea* (e.g., (field) mustard) and *Brassica carinata*, Arecaceae sp. (e.g., oilpalm, coconut), rice, wheat, sugar beet, sugar cane, oats, rye, barley, millet and sorghum, triticale, flax, nuts, grapes and vine and various fruit and vegetables from various botanic taxa, e.g., Rosaceae sp. (e.g., pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Moraceae sp., Oleaceae sp. (e.g. olive tree), Actinidaceae sp., Lauraceae sp. (e.g., avocado, cinnamon, camphor), Musaceae sp. (e.g., banana trees and plantations), Rubiaceae sp. (e.g., coffee), Theaceae sp. (e.g., tea), Sterculiceae sp., Rutaceae sp. (e.g., lemons, oranges, mandarins and grapefruit); Solanaceae sp. (e.g., tomatoes, potatoes, peppers, *capsicum*, aubergines, tobacco), Liliaceae sp., Compositae sp. (e.g., lettuce, artichokes and chicory—including root chicory, endive or common chicory), Umbelliferae sp. (e.g., carrots, parsley, celery and celeriac), Cucurbitaceae sp. (e.g., cucumbers—including gherkins, pumpkins, watermelons, calabashes and melons), Alliaceae sp. (e.g., leeks and onions), Cruciferae sp. (e.g., white cabbage, red cabbage, broccoli, cauliflower, Brussels sprouts, pak choi, kohlrabi, radishes, horseradish, cress and chinese cabbage), Leguminosae sp. (e.g., peanuts, peas, lentils and beans—e.g., common beans and broad beans), Chenopodiaceae sp. (e.g. Swiss chard, fodder beet, spinach, beetroot), Linaceae sp. (e.g., hemp), Cannabeacea sp. (e.g., *Cannabis*), Malvaceae sp. (e.g., okra, cocoa), Papaveraceae (e.g., poppy), Asparagaceae (e.g., asparagus); useful plants and ornamental plants in the garden and woods including turf, lawn, grass and *Stevia rebaudiana*; and in each case genetically modified types of these plants.

In certain aspects, the fermentation product further comprises a formulation ingredient. The formulation ingredient may be a wetting agent, extender, solvent, spontaneity promoter, emulsifier, dispersant, frost protectant, thickener, and/or an adjuvant. In one embodiment, the formulation ingredient is a wetting agent. In other aspects, the fermentation product is a freeze-dried powder or a spray-dried powder.

Compositions of the present invention may include formulation ingredients added to compositions of the present invention to improve recovery, efficacy, or physical properties and/or to aid in processing, packaging and administration. Such formulation ingredients may be added individually or in combination.

The formulation ingredients may be added to compositions comprising cells, cell-free preparations, isolated compounds, and/or metabolites to improve efficacy, stability, and physical properties, usability and/or to facilitate processing, packaging and end-use application. Such formulation ingredients may include agriculturally acceptable carriers, inerts, stabilization agents, preservatives, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the formulation ingredient is a binder, adjuvant, or adhesive that facilitates adherence of the composition to a plant part, such as leaves, seeds, or roots. See, for example, Taylor, A. G., et al., "Concepts and Technologies of Selected Seed Treatments," Annu. Rev. Phytopathol., 28: 321-339 (1990). The stabilization agents may include anti-caking agents, anti-oxidation agents, anti-settling agents, antifoaming agents, desiccants, protectants or preservatives. The nutrients may include carbon, nitrogen, and phosphorus sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, film-formers, hydrotropes, builders, antifreeze agents or colorants. In some embodiments, the composition comprising cells, cell-free preparation and/or metabolites produced by fermentation can be used directly with or without water as the diluent without any other formulation preparation. In a particular embodiment, a wetting agent, or a dispersant, is added to a fermentation solid, such as a freeze-dried or spray-dried powder. In some embodiments, the formulation inerts are added after concentrating fermentation broth and/or during and/or after drying. A wetting agent increases the spreading and penetrating properties, or a dispersant increases the dispersibility and solubility of the active ingredient (once diluted) when it is applied to surfaces. Exemplary wetting agents are known to those of skill in the art and include sulfosuccinates and derivatives, such as MULTI-WET™ MO-70R (Croda Inc., Edison, NJ); siloxanes such as BREAK-THRU® (Evonik, Germany); nonionic compounds, such as ATLOX™ 4894 (Croda Inc., Edison, NJ); alkyl polyglucosides, such as TERWET© 3001 (Huntsman International LLC, The Woodlands, Texas); C12-C14 alcohol ethoxylate, such as TERGITOL® 15-S-15 (The Dow Chemical Company, Midland, Michigan); phosphate esters, such as RHODAFAC® BG-510 (Rhodia, Inc.); and alkyl ether carboxylates, such as EMULSOGEN™ LS (Clariant Corporation, North Carolina).

Deposit Information

Samples of the *Paenibacillus* sp. strains of the invention have been deposited with the Agricultural Research Service Culture Collection located at the National Center for Agricultural Utilization Research, Agricultural Research Service, U.S. Department of Agriculture (NRRL), 1815 North University Street, Peoria, IL 61604, U.S.A., under the Budapest Treaty. *Paenibacillus* sp. NRRL B-50972 was deposited on Aug. 28, 2014. *Paenibacillus* sp. NRRL B-67129 was deposited on Sep. 1, 2015. *Paenibacillus* sp. NRRL B-67304 and *Paenibacillus* sp. NRRL B-67306 were both deposited on Jul. 22, 2016. *Paenibacillus* sp. NRRL B-67615 was deposited on May 3, 2018.

The *Paenibacillus* sp. strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. However, it should be understood that the availability of a deposit does not constitute a license to practice the subject invention in derogation of patent rights granted by governmental action.

The following examples are given for purely illustrative and non-limiting purposes of the present invention.

EXAMPLES

Example 1. Enhancing Fusaricidin Production of *Paenibacillus* sp. Strain NRRL B-67129 and Mutant Derivatives

*Paenibacillus* sp. strain NRRL B-67129 was treated with 1-methyl-3-nitro-1-nitroguanidine (NTG) or ethyl methanesulfonate (EMS) to introduce genetic variation. Treatment resulting in a 50-90% loss in colony-forming units (CFU) was considered appropriate to obtain sufficient genetic variation and viable cells for subsequent screening. Individual isolates from the chemically-treated populations were cultured in 96-well deep well blocks and screened for increased production of four fusaricidin-like compounds, namely fusaricidin A (also known as "Fus A"), LiF08a, Paeniserines A1 and B1 (also known as "M868" for their molecular mass); and Paeniprolixins A2 and B2 (also known as "M938" for their molecular mass) as described in WO 2016/154297.

Isolates with apparent improved fusaricidin levels from this initial screen were rescreened in technical replicates in 96-well deep well blocks and confirmed to be overproducers. Confirmed isolates were subsequently scaled up and analyzed for fusaricidin production and growth attributes including the ability to make heat-resistant bacterial spores. From an initial round of screening, confirmation, and scale up, several overproducing isolates were identified and once again chemically-treated and screened for further improvements in fusaricidin production. This process was repeated several times.

The strains identified with this analysis were further evaluated to confirm fusaricidin production. Briefly, each strain was cultured in a soy-based medium and the lipophilic fraction of the whole broth was extracted. The whole broth extract was analyzed via high-performance liquid chromatography (HPLC) and the presence of fusaricidin A was identified based on the HPLC profile generated with a standard sample containing fusaricidin A. The ability of the mutant strains to produce heat-resistant spores was also evaluated.

In total, approximately 10,000 isolates derived from *Paenibacillus* sp. strain NRRL B-67129 were screened in the 96-well deep well block format. This analysis yielded several isolates of interest which were characterized for their relative levels of the four fusaricidin-like compounds (see Table 1). These strains were extensively characterized, and *Paenibacillus* sp. strain J was identified as displaying elevated fusaricidin production and favorable growth attributes (e.g., sporulation) compared to *Paenibacillus* sp. strain NRRL B-67129. However, *Paenibacillus* sp. strain J produced a viscous fermentation broth that made it difficult to process. From this observation, it became apparent that it was necessary to screen the mutant strains for their viscosity in liquid culture as well as for their production of fusaricidin-like compounds.

TABLE 1

Relative fusaricidin production from *Paenibacillus* sp. strain NRRL B-50972, *Paenibacillus* sp. strain NRRL B-67129, and mutant strains derived from *Paenibacillus* sp. strain

| Strain | FusA | M868 | M938 | LiF08a |
|---|---|---|---|---|
| NRRL B-67129 | 1.00 | 1.00 | 1.00 | 1.00 |
| NRRL B-50972 | 1.05 | 1.09 | 1.03 | 1.05 |
| Strain A | N.D. | N.D. | N.D. | N.D. |
| Strain B | N.D. | N.D. | N.D. | N.D. |
| Strain C | N.D. | N.D. | N.D. | N.D. |
| Strain D | 0.58 | 0.47 | 0.71 | 0.84 |
| Strain E | 0.81 | 0.80 | 0.82 | 0.91 |
| Strain F | 0.83 | 0.86 | 0.89 | 0.94 |
| Strain G | 0.83 | 0.89 | 0.98 | 0.96 |
| Strain H | 0.99 | 0.97 | 0.98 | 0.97 |
| Strain I | 1.07 | 1.16 | 1.07 | 1.10 |
| Strain J | 1.12 | 1.21 | 1.11 | 1.15 |
| Strain K | 1.12 | 1.23 | 1.24 | 1.17 |
| Strain L | 1.16 | 1.32 | 1.25 | 1.19 |

TABLE 1-continued Relative fusaricidin production from *Paenibacillus* sp. strain NRRL B-50972, *Paenibacillus* sp. strain NRRL B-67129, and mutant strains derived from *Paenibacillus* sp. strain

| Strain | FusA | M868 | M938 | LiF08a |
|---|---|---|---|---|
| Strain M | 1.17 | 1.36 | 1.26 | 1.22 |
| Strain N | 1.25 | 1.51 | 1.26 | 1.44 |
| Strain O | 1.27 | 1.57 | 1.35 | 1.69 |
| Strain P | 1.37 | 1.64 | 1.55 | 1.69 |
| Strain Q | 1.40 | 1.65 | 1.55 | 1.76 |
| Strain R | 1.48 | 1.68 | 1.59 | 1.82 |
| NRRL B-67304 | 1.59 | 1.99 | 1.81 | 2.15 |
| Strain T | 1.61 | 2.15 | 2.41 | 2.29 |
| NRRL B-67306 | 1.83 | 3.26 | 2.63 | 2.54 |
| Strain V | 1.92 | 4.00 | 3.15 | 2.79 |
| Strain W | 2.71 | 9.49 | 3.53 | 4.46 |

N.D. = Not Detected.

Strains identified with italicized font are those with a non-mucoid phenotype on solid agar containing sucrose as described in Example 2.

Example 2. Reduction of Fermentation Broth Viscosity of *Paenibacillus* sp. Strain NRRL B-67129 Mutant Derivatives

*Paenibacillus* sp. strain NRRL B-50972 and *Paenibacillus* sp. strain NRRL B-67129 produced viscous fermentation broth cultures as did many of the mutant strains derived from *Paenibacillus* sp. strain NRRL B-67129. The physicochemical properties of these cultures presented challenges in fermentation and downstream processing. It was therefore desirable to identify a way of identifying mutant derivatives of *Paenibacillus* sp. strain NRRL B-67129 producing less viscous fermentation broth cultures.

Sucrose is often used as a carbon source for exopolysaccharide (EPS) production by *Paenibacillus* spp., and it has been reported that the use of sucrose results in significant yields of high molecular weight levan-type EPS (Liang and Wang. *Mar. Drugs* 2015, 13, 1847-1863). High molecular weight EPS polymers have found commercial use as thickening agents. Along with sucrose, other oligosaccharides and polysaccharides are used as carbon sources for EPS production in *Paenibacillus*.

A distinct mucoid colony phenotype was observed when *Paenibacillus* sp. strain NRRL B-67129 and mutant derivatives were grown on solid agar medium supplemented with sucrose at a final concentration between 0.25-0.5 M (see the recipe in Table 2). A similar solid agar medium containing 200 g/L maltodextrin also revealed the mucoid colony phenotype.

Figure 2:
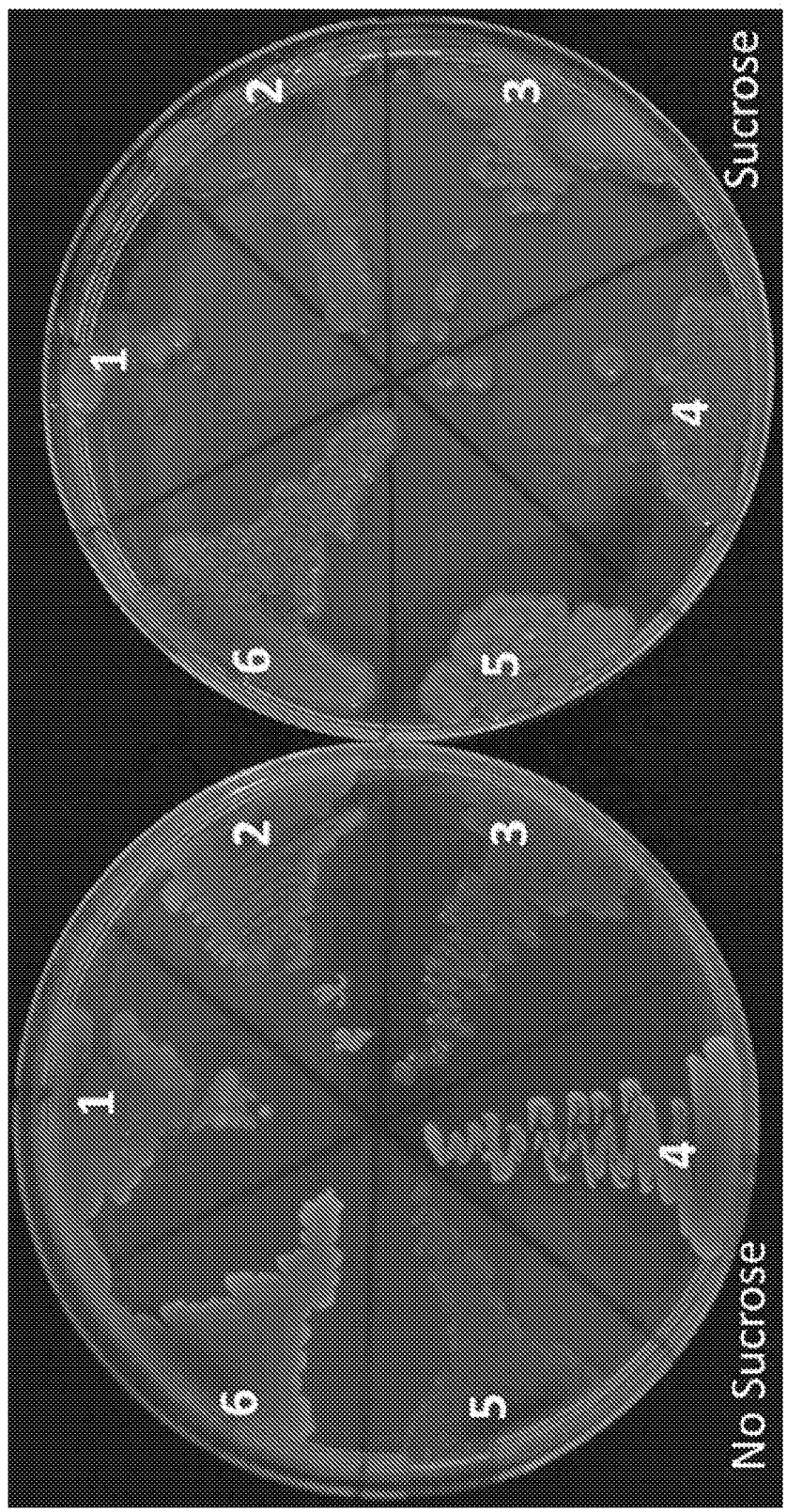
FIG. 2 depicts *Paenibacillus* spp. strains with a mucoid colony phenotype grown on sucrose-containing solid agar medium compared to the same *Paenibacillus* spp. strains lacking the mucoid colony phenotype grown on solid agar medium without sucrose. The *Paenibacillus* spp. strains are: (1) *Paenibacillus terrae* strain A; (2) *Paenibacillus brasilensis* strain B; (3) *Paenibacillus* sp. strain NRRL B-50972; (4) *Paenibacillus polymyxa* strain C; (5) *Paenibacillus polymyxa* strain D; and (6) *Paenibacillus peoriae* strain E.

Several *Paenibacillus* spp. strains including strains of *P. terrae*, *P. brasilensis*, *P. polymyxa*, and *P. peoriae* produced a mucoid phenotype on the sucrose-containing solid agar medium (see FIG. 2). It was hypothesized that a rapid visual screen could be set up for non-mucoid colony isolates which result in fermentation broth cultures with reduced viscosity and enhanced physical properties. Without wishing to be bound to any theory, the mucoid colony phenotype may correspond to the production of EPS by *Paenibacillus* sp. strain NRRL B-67129, its mutant derivatives, and other *Paenibacillus* spp. strains in submerged culture.

TABLE 2

Solid agar media recipe with sucrose for identifying the mucoid phenotype

| Component | Per liter (g) |
|---|---|
| Tryptone | 10 |
| Yeast Extract | 5 |
| NaCl | 5 |
| Sucrose (0.25M-0.5M) | 86-172 |
| Maleate Buffer (pH 6.5) (0.02M) | 2.32 mL |
| MgCl$_2$ | 1.9 |
| Agar (1.5%) | 15 |

The following protocol was developed and validated as a rapid visual screen for identifying non-mucoid colony isolates. Liquid cultures of fungicidal mutant derivatives of *Paenibacillus* sp. strain NRRL B-67129 were subjected to chemical treatment, and subsequently diluted and inoculated onto solid agar medium supplemented with sucrose to obtain single colonies. Non-mucoid colonies were easily distinguishable by eye from mucoid colonies (see FIG. 3). Non-mucoid isolates were picked and streaked onto fresh solid agar medium supplemented with sucrose to confirm the phenotype.

Figure 4:
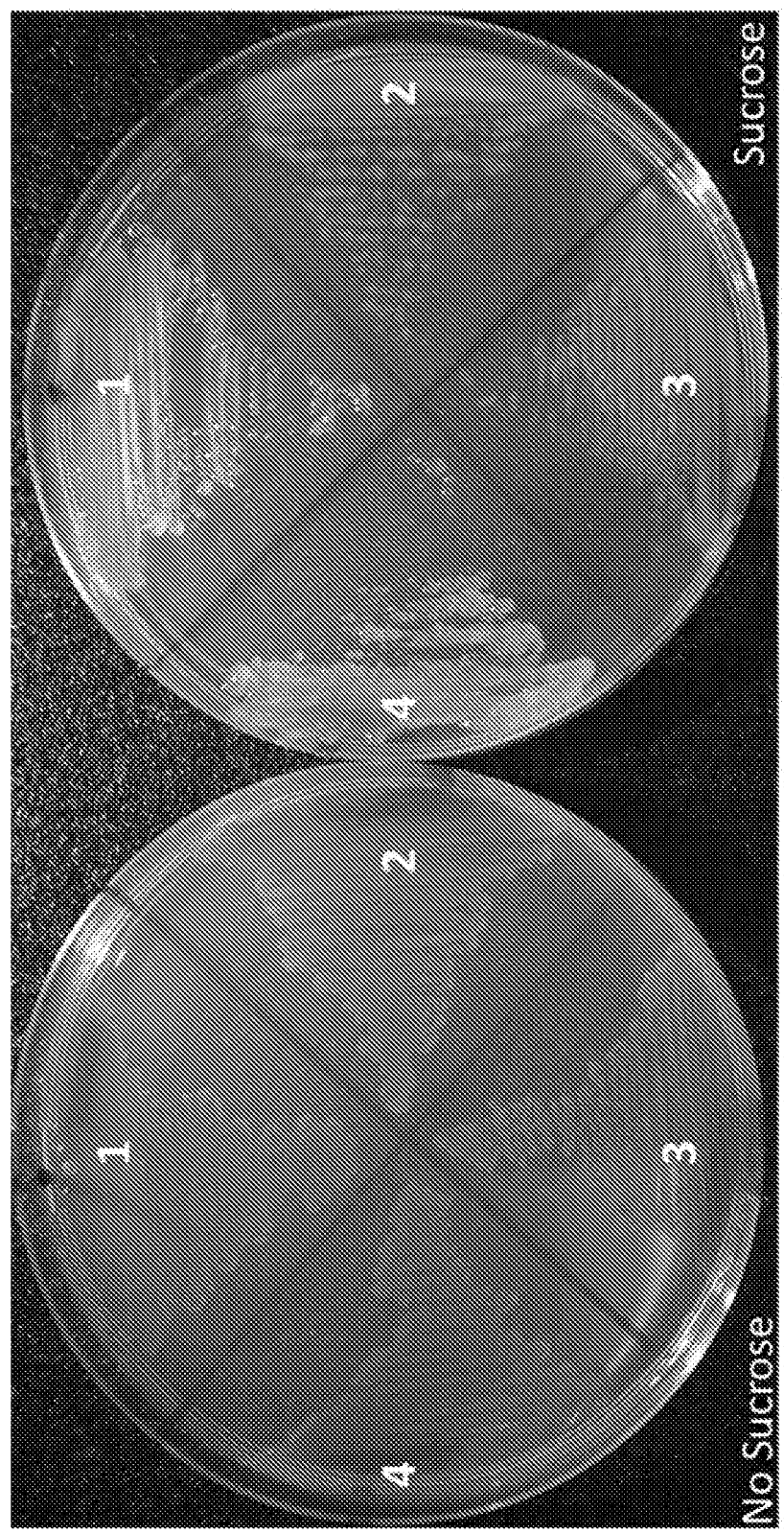
FIG. 4 depicts the mucoid colony phenotype of (1) *Paenibacillus* sp. strain NRRL B-50972 and (4) *Paenibacillus* sp. strain NRRL B-67129 contrasted to the non-mucoid phenotype of (2) *Paenibacillus* sp. strain NRRL B-67304 and (3) *Paenibacillus* sp. strain NRRL B-67306 on sucrose-containing solid agar medium. All strains have a non-mucoid phenotype on the control solid agar medium without sucrose.

Eight non-mucoid isolates were identified from fusaricidin overproducing parent strains derived from *Paenibacillus* sp. strain NRRL B-67129. The non-mucoid isolates included *Paenibacillus* sp. strain NRRL B-67306 and *Paenibacillus* sp. strain NRRL B-67304 (see FIG. 4). Six out of the eight isolates produced fusaricidin biomarkers at or above levels comparable to their respective parent strains. In addition, five out of the eight isolates were capable of producing heat-resistant spores at levels similar to those produced by *Paenibacillus* sp. strain NRRL B-67129 under the same conditions. These observations indicated that the cellular processes related to fusaricidin production, sporulation, and viscosity-producing agents are genetically separable.

The eight non-mucoid isolates were evaluated in larger scale cultures, and two non-mucoid isolates, *Paenibacillus* sp. strain NRRL B-67306 and *Paenibacillus* sp. strain NRRL B-67304, were found to have improved fusaricidin production and favorable growth attributes in soy-based medium. These strains were analyzed for their packed cell volume (% PCV) and their viscosity.

% PCV was quantified by centrifuging a 1 mL volume at 17,000 g for 3 minutes in a 2 mL microfuge tube. A percent packed cell volume was determined based on graduations on the tube setting the original 1 mL sample volume mark as 100%.

Alternatively, about 10 mL of whole broth was placed in 15 mL centrifuge tube, the weight of whole broth ("$W_{wb}$") was recorded, the sample was centrifuged for 10 minutes at 10,000 g, the supernatant was poured off, and the weight of the supernatant ("$W_{sup}$") was recorded. To calculate % PCV the following equation was used:

$$\% \text{ PCV} = 100 \times (W_{wb} - W_{sup})/(W_{wb})$$

Viscosity of fermentation broth was tested in a viscometer at 50 rpm, and values were reported in centipoise.

Figure 5:
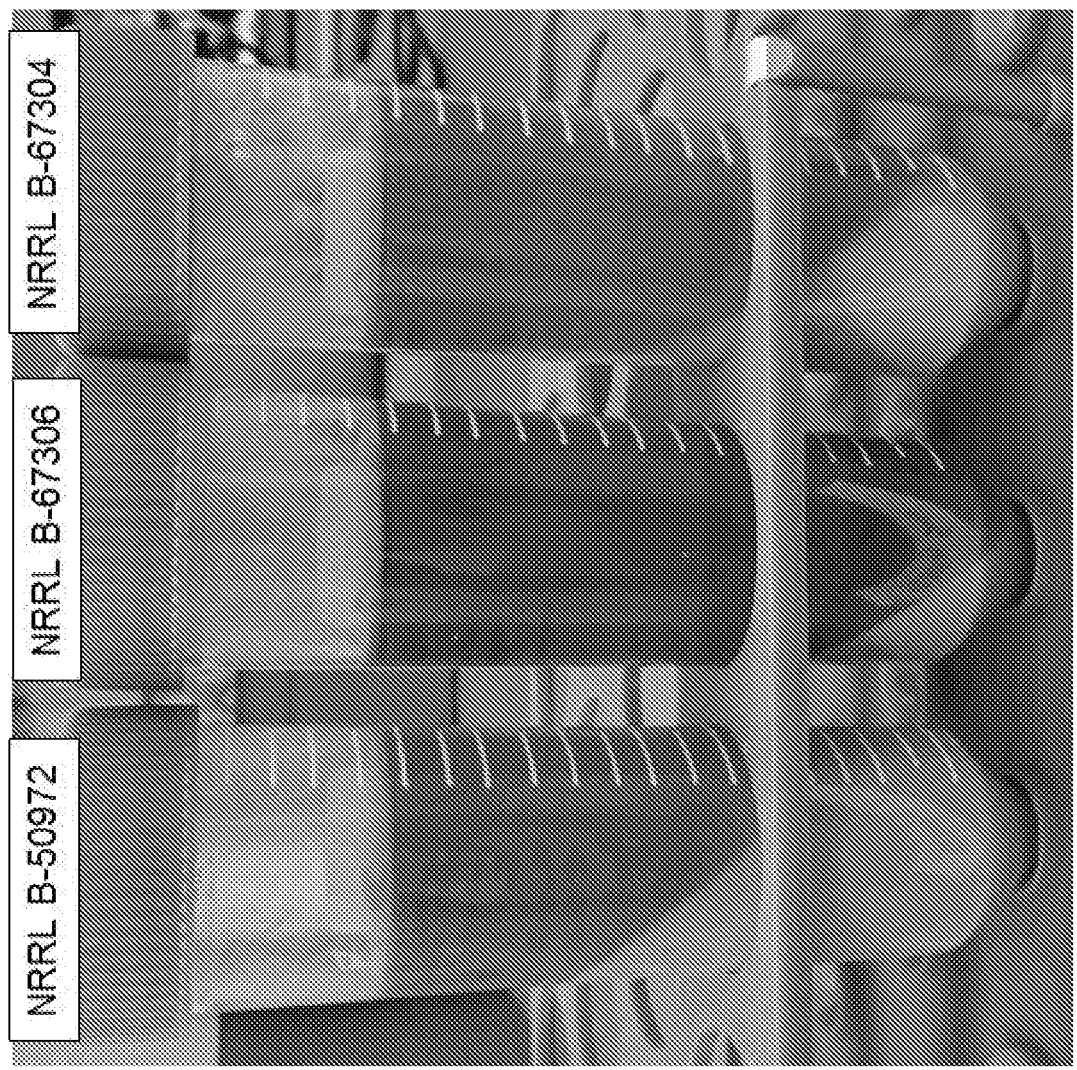
FIG. 5 depicts the pelleting of fermentation broths after centrifugation of *Paenibacillus* sp. strain NRRL B-50972, *Paenibacillus* sp. strain NRRL B-67304, and *Paenibacillus* sp. strain NRRL B-67306. The strains with a non-mucoid phenotype on sucrose-containing solid agar medium tend to form a more compact pellet with a smaller packed cell volume (PCV).

*Paenibacillus* sp. strain NRRL B-67306 and *Paenibacillus* sp. strain NRRL B-67304 produced fermentation broths with viscosities of 11.5 and 33.9 centipoise (cP), respectively, relative to 56 cP for fermentation broth of *Paenibacillus* sp. strain NRRL B-50972 (see Table 3). In addition, *Paenibacillus* sp. strain NRRL B-67306 and *Paenibacillus* sp. strain NRRL B-67304 produced smaller packed-cell volumes (PCV) compared to *Paenibacillus* sp. strain NRRL B-50972 (see Table 3 and FIG. 5). These results validated the hypothesis that the rapid visual screen on solid medium containing high levels of polysaccharide (e.g., sucrose or maltodextrin) could identify non-mucoid colony isolates which resulted in fermentation broth cultures with reduced viscosity and enhanced physical properties.

The improved physical properties of the fermentation broths from *Paenibacillus* sp. strain NRRL B-67306 and *Paenibacillus* sp. strain NRRL B-67304 allowed for enhanced processability of these non-mucoid strains as live microbe-based products. The lower PCVs and viscosities of the fermentation broths enable greater concentration of whole broth material in order to reduce use-rates in agriculture applications.

TABLE 3

Viscosity and packed cell volumes (PCV) of *Paenibacillus* sp. strain NRRL B-50972 and non-mucoid derivative strains.

| Strain | PCV (%) | Viscosity (cP) |
|---|---|---|
| NRRL B-50972 | 54 | 56.0 |
| NRRL B-67306 | 14 | 11.5 |
| NRRL B-67304 | 34 | 33.9 |

Example 3. Mutational Analysis of Strain Improvement Isolates

Figure 6A:
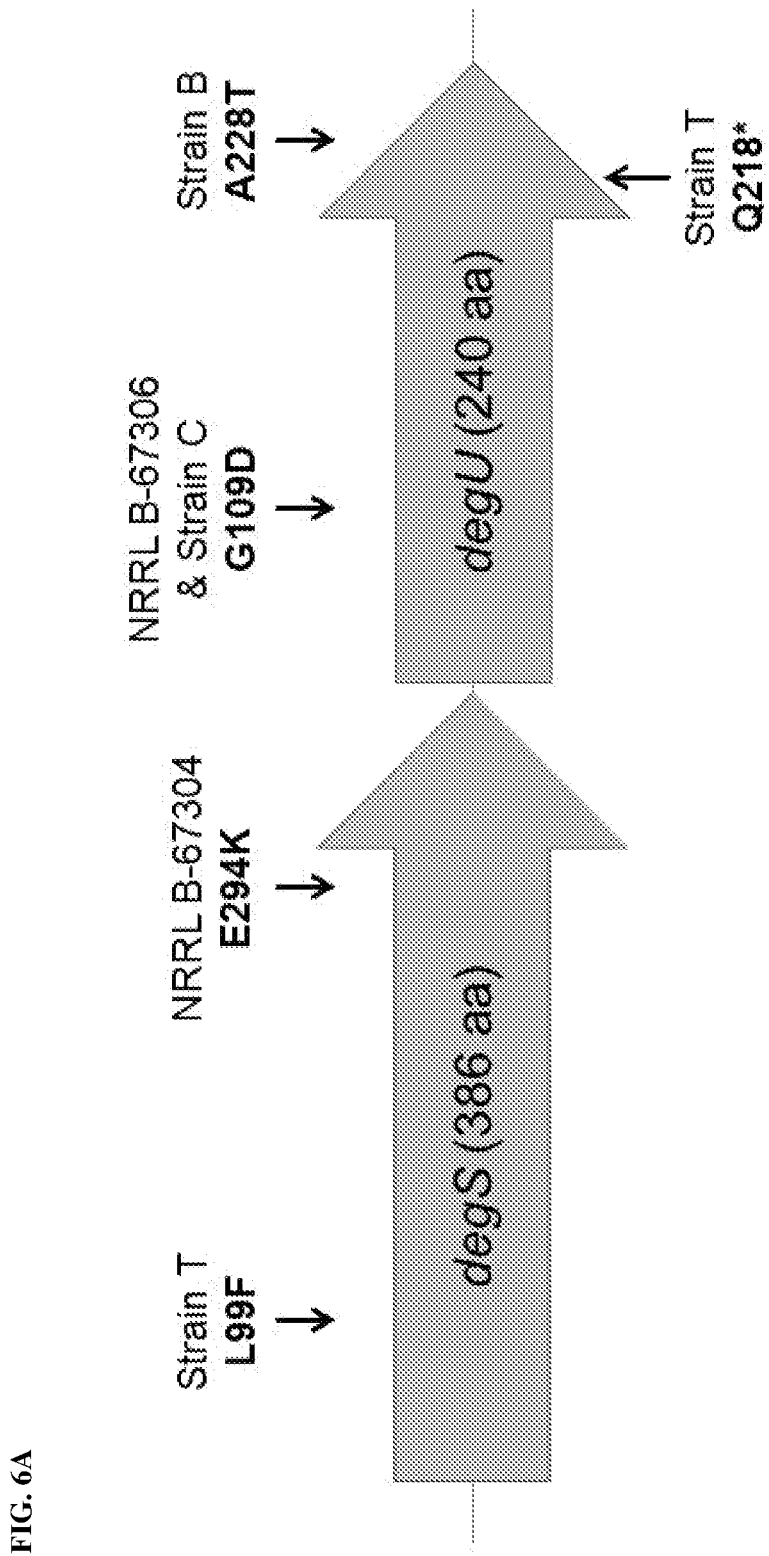
FIG. 6A depicts SNPs in the degS and degU genes identified in *Paenibacillus* sp. strains with a non-mucoidal colony phenotype.

The genome sequences of several isolates with the non-mucoid phenotype were determined using standard sequencing methods. Single nucleotide polymorphisms (SNPs) for the isolates were compared. Surprisingly, it was found that five out of eight of the non-mucoid strains derived from *Paenibacillus* sp. strain NRRL B-67129, including *Paenibacillus* sp. strain NRRL B-67304 and *Paenibacillus* sp. strain NRRL B-67306, had mutations in the protein codon sequences of the degS degU region (see FIG. 6A). These mutations fell within the receiver domain and the DNA binding domain of DegU and within the single binding domain and the ATPase domain of DegS (see FIGS. 6B-6C).

It was hypothesized that these mutations in degS and degU were related to the non-mucoidal phenotype of these isolates on solid agar plates supplemented with sucrose. To test this DNA constructs were made using standard molecular practices to replace the degS gene with a kanamycin cassette and to replace the degS and degU region with a kanamycin cassette in the parental *Paenibacillus* sp. strain B-67129.

Figure 7:
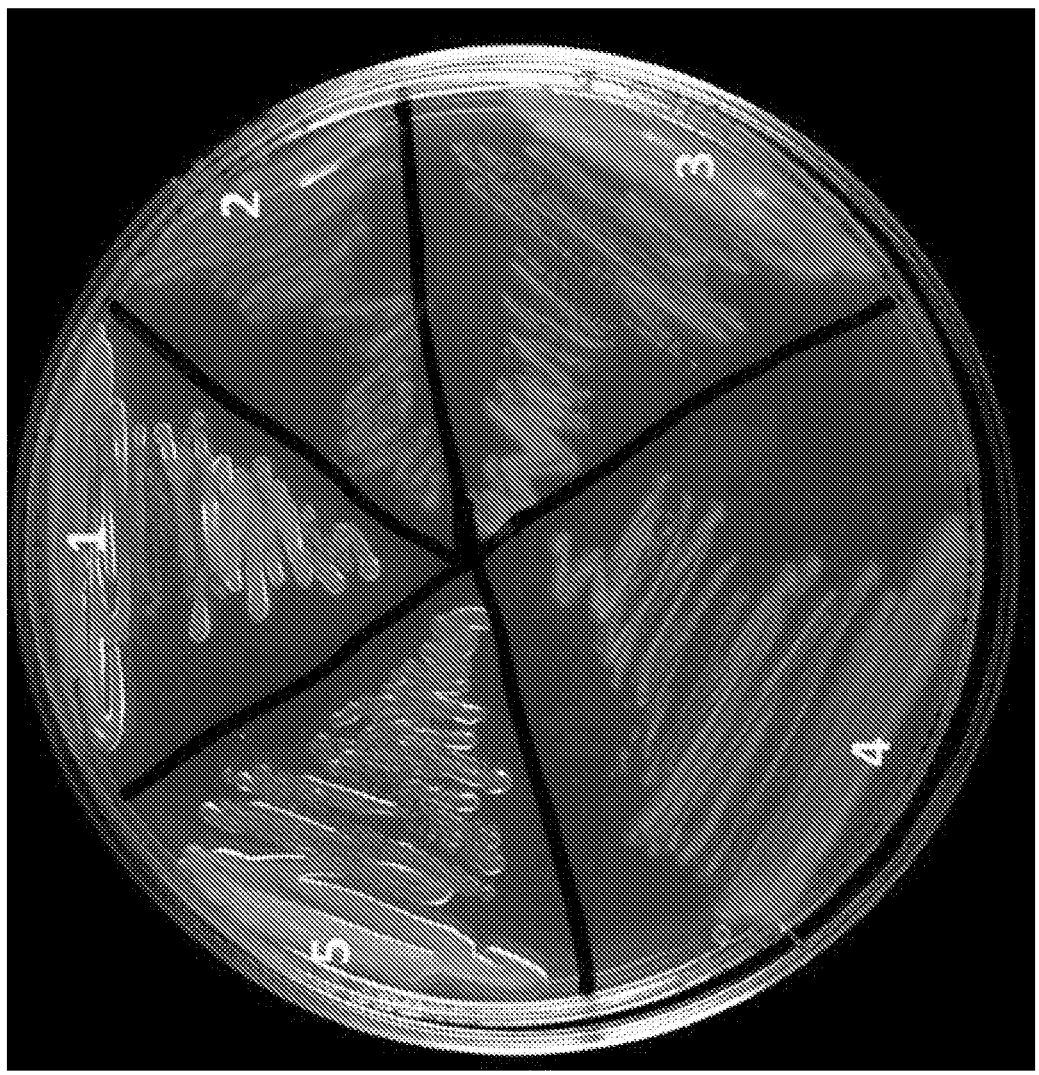
FIG. 7 depicts disruption of degS and degU results in a non-mucoidal colony phenotype with *Paenibacillus* sp. strains on sucrose-containing solid agar medium. The *Paenibacillus* sp. strain are: (1) *Paenibacillus* sp. strain NRRL B-67129; (2) *Paenibacillus* sp. strain NRRL B-67306; (3) *Paenibacillus* sp. strain NRRL B-67129 degS::kanR; (4) *Paenibacillus* sp. strain NRRL B-67129 degSdegU::kanR; and (5) *Paenibacillus terrae* strain F.

The gene encoding kanamycin resistance (kanR) was cloned into a conjugatable *E. coli-Paenibacillus* shuttle plasmid flanked by 1 kbp region upstream of the gene encoding DegS and 1 kbp downstream of the gene encoding DegS or DegU targeting the replacement of degS alone or degS and degU by kanR. This plasmid was first introduced into an *E. coli* strain by electroporation and subsequently moved into *Paenibacillus* sp. strain NRRL B-67129 by conjugation. Erythromycin resistance encoded by the plasmid backbone was utilized to select for successful plasmid transfer. Kanamycin resistance, erythromycin sensitivity, and PCR validation were used to confirm double cross-over integrants. Both kanamycin resistant marker-replacement strains, *Paenibacillus* sp. strain NRRL B-67129 degS::kanR and *Paenibacillus* sp. strain NRRL B-67129 degSdegU::kanR mimicked the non-mucoid phenotype of the isolates selected previously (see FIG. 7). These results confirmed that mutations in degS and degU leading to non-functional gene products produce the non-mucoid phenotype.

Other mutations in degS and degU have been characterized and lead to non-functional gene products. The residue serine76 in *Bacillus subtilis* strain 168, which corresponds with threonine73 in *Paenibacillus* sp. strain NRRL B-50972, is a phosphorylation site stimulating its kinase activity, and mutation of serine76 to alanine significantly reduced the enzymatic activity of DegS. See Jers, C. et al., "*Bacillus subtilis* Two-Component System Sensory Kinase DegS is Regulated by Serine Phosphorylation in Its Input Domain," PLoS ONE (2011) 6(2):e14653. Mutation of the residue alanine193 in *Bacillus subtilis* strain 168, which corresponds with alanine190 in *Paenibacillus* sp. strain NRRL B-50972, to valine essentially abolished the kinase activity of DegS. See Dahl, M. K. et al., "The Phosphorylation State of the DegU Response Regulator Acts as a Molecular Switch Allowing Either Degradative Enzyme Synthesis or Expression of Genetic Competence in *Bacillus subtilis*," J. Biol. Chem. (1992) 267(20):14509.

A degU mutation resulting in a substitution of aspartate56, which corresponds with aspartate63 in *Paenibacillus* sp. strain NRRL B-50972, to asparagine prevented the phosphorytion of DegU by DegS. See Dahl, M. K. et al., supra. Alanine scanning of the DNA Binding Domain of DegU revealed five common mutants that caused a severe reduction of DegU binding to the promoter regions of comK and aprE and a consequent reduction of expression of these genes along with three additional mutants inhibiting binding of DegU to the promoter region of aprE and a consequent reduction of expression in this gene. See the mutants in Table 4 reported in Shimane et al., "Mutational Analysis of the Helix-Turn-Helix Region of *Bacillus subtilis* Response Regulator DegU, and Identification of cis-Acting Sequences for DegU in the aprE and comK Promoters," J. Biochem. (2004) 136(3):387-397.

Based on the results with the replacement of the degS gene or of the degS and degU genes with an antibiotic resistance cassette, it is concluded that any mutation in degS or deg U leading to a non-functional gene product including those described above will result in *Paenibacillus* sp. strains with decreased viscosity in liquid culture and/or a non-mucoidal colony morphology compared to a *Paenibacillus* sp. strain comprising a wild-type DegU and a wild-type DegS.

TABLE 4

Amino acid substitutions affecting DNA binding function of DegU

| Substitution | Position in *Bacillus subtilis* strain 168 | Position in *Paenibacillus* sp. strain NRRL B-50972 | Gene Promoter Target Affected by Substitution |
|---|---|---|---|
| N → A | 183 | 195 | comK and aprE |
| I → A | 192 | 204 | comK and aprE |
| T → A | 196 | 208 | comK and aprE |
| H → A | 200 | 212 | comK and aprE |
| L → A | 205 | 217 | comK and aprE |
| K → A | 195 | 207 | aprE |
| N → A | 199 | 211 | aprE |
| S → A | 202 | 214 | aprE |

| Strain | Protein | SEQ ID NO: | Sequence |
|---|---|---|---|
| *Bacillus subtilis* strain 168 | DegU | 1 | MTKVNIVIIDDHQLFREGVKRILDFEPTFEVVAEGDDGDEAARIVEHYHPDVVIMDINMPNVN GVEATKQLVELYPESKVIILSIHDDENYVTHALKTGARGYLLKEMDADTLIEAVKVVAEGGSY LHPKVTHNLVNEFRRLATSGVSAHPQHEVYPEIRRPLHILTRRECEVLQMLADGKSNRGIGESL FISEKTVKNHVSNILQKMNVNDRTQAVVVAIKNGWVEMR |
| *Paenibacillus* sp. strain NRRL B-50972 | DegU | 2 | MENQEISNAPIKVLLADDHQLFREGLKRILNMEDDIEVIGECGDGIQVLEFCNVEKPDIVLMDI NMPIENGVEATEKLREMFPDVKVIILSIHDDESYVFETLRKGANGYLLKDMEAESLINAIRSVH EGYAFIHPKVTGKLIQQLRRMTYLNETGAMAEGHTKEAGVKFVAGENNPLTRREAEVLRLM AEGKSNKMIGEYLFISEKTVKNHVSSILQKMEVDDRTQAVINSIKYGWVTL |
| *Bacillus subtilis* strain 168 | DegS | 3 | MNKTKMDSKVLDSILMKMLKTVDGSKDEVFQIGEQSRQQYEQLVEELKQIKQQVYEVIELGD KLEVQTRHARNRLSEVSRNFHRFSEEEIRNAYEKAHKLQVELTMIQQREKQLRERRDDLERRL LGLQEIIERSESLVSQITVVLNYLNQDLREVGLLLADAQAKQDFGLRIIEAQEEERKRVSREIHD GPAQMLANVMMRSELIERIFRDRGAEDGFQEIKNLRQNVRNALYEVRRIIYDLRPMALDDLG LIPTLRKYLYTTEEYNGKVKIHFQCIGETEDQRLAPQFEVALFRLAQEAVSNALKHSESEEITV KVEITKDFVILMIKDNGKGFDLKEAKEKKNKSFGLLGMKERVDLLEGTMTIDSKIGLGTFIMIK VPLSL |
| *Paenibacillus* sp. strain NRRL B-50972 | DegS | 4 | VDFQADIIDRVIKNAIQVMENSKYQMFEILDTARTELITLNQELQSVLKETAETIEKVDQLEMN YRRSRIRLTEVSRDFVRYSEEDIKQAYEKATQLQLDVMIFREKEMYLKARRDDLQKRAKSVE ASVERAETIGSQMGVVLEYLSGELGQVTRIIESAKNRQFIGLKIILAQEEERKRISREIHDGPAQ LLAHLVLRTEIVERMIAKQEFKMVQDEIVDLKKQVRSSLEEMRKVIFNLRPMALDDLGLVPTLR KYVQDFEEKTKIRSLFETRGKEHRLSSAMEEAAIYRLIQEALTNAAKHAYPTYVLVEITYQAQL VKIVVQDNGLGFKPELFQQKSKDHGHFGLIGMRERVELLEGRMEIESAENQGTKIVIHIPTNVE KGKE |

| Strain | Gene | SEQ ID NO: | Sequence |
|---|---|---|---|
| *Bacillus subtilis* strain 168 | degU | 5 | GTGACTAAAGTAAACATTGTTATTATCGACGACCATCAGTTATTTCGTGAAGGTGTTAAAC GGATATTGGATTTTGAACCTACCTTTGAAGTGGTAGCCGAAGGTGATGACGGGGACGAAG CGGCTCGTATTGTTGAGCACTATCATCCTGATGTTGTGATCATGGATATCAATATGCCAAA CGTAAATGGTGTGGAAGCTACAAAACAGCTTGTAGAGCTGTATCCTGAATCTAAAGTAAT TATTCTATCAATTCACGATGACGAAAATTATGTAACACATGCCCTGAAAACAGGTGCAAG AGGTTATCTGCTGAAAGAGATGGATGCTGATACATTAATTGAAGCGGTTAAAGTAGTGGC TGAGGGCGGATCTTACCTCCATCCGAAGGTTACTCACAACCTCGTTAACGAATTCCGCCG CCTTGCAACAAGCGGAGTTTCTGCACACCCTCAACATGAGGTTTACCCTGAAATCCGCAG ACCATTACATATTTTAACTAGGCGGGAATGTGAAGTGCTGCAGATGCTTGCAGACGGAAA AAGCAACCGCGGTATTGGTGAATCATTGTTTATCAGTGAGAAAACCGTTAAAAACCATGT CAGCAATATTTTACAAAAAATGAATGTAAACGACCGGACGCAAGCCGTTGTGGTCGCCAT TAAAAATGGCTGGGTAGAAATGAGATAG |
| *Paenibacillus* sp. strain NRRL B-50972 | degU | 6 | ATGGAAAATCAGGAAATTAGTAACGCACCCATTAAAGTACTCTTGGCGGACGATCATCAG TTGTTCCGTGAAGGGCTTAAACGTATTTTGAATATGGAGGACGACATTGAGGTCATCGGC GAATGTGGCGATGGTATTCAGGTGTTGGAGTTCTGTAATGTAGAGAAGCCGGATATCGTT CTGATGGACATTAATATGCCTATTGAAAACGGTGTAGAGGCAACTGAAAAACTGCGTGAG ATGTTCCCGGATGTCAAAGTTATCATTCTGTCCATTCATGATGATGAAAGCTATGTATTCG AGACGTTGCGCAAGGGAGCTAACGGCTACCTGTTAAAAGATATGGAGGCCGAGTCCCTCA TTAACGCGATTCGCTCTGTACATGAAGGGTATGCGTTTATTCATCCGAAGGTAACGGGTA AACTCATTCAGCAGCTCCGTCGGATGACGTACCTGAATGAAACCGGGGCTATGGCTGAAG GTCATACCAAGGAAGCTGGCGTGAAGTTCGTCGCAGGCGAAAATAACCCACTGACCCGTC GTGAGGCTGAAGTGTTGCGCTTAATGGCAGAAGGCAAGAGCAACAAGATGATCGGTGAA TATTTATTCATTAGTGAAAAAACCGTTCAAAAACCATGTCAGCAGTATTTTGCAAAAAATG GAGGTTGATGACCGGACACAAGCGGTTATTAACTCAATCAAATACGGATGGGTTACGCTG TAA |
| *Bacillus subtilis* strain 168 | degS | 7 | ATGAATAAAACAAAGATGGATTCCAAAGTGCTGGATTCTATTTTGATGAAGATGCTGAAA ACCGTTGACGGGAGCAAGGACGAGGTTTTTCAAATCGGGGAGCAGTCACGCCAGCAGTA TGAACAGCTGGTCGAAGAACTGAAACAAATTAAACAGCAGGTGTATGAAGTGATTGAGC TTGGCGATAAACTTGAAGTGCAAACTCGCCATGCGCGAGAAACCGTTTATCCGAGGTCAGCC GTAATTTTCATAGATTCAGTGAAGAGGAAATCCGCAATGCTTATGAAAAGCCCATAAGC TGCAGGTAGAATTGACGATGATCCAGCAGCGTGAGAAGCAATTGCGCGAACGGCGGGAC GATTTGGAGCGCAGATTGCTAGGGCTTCAGGAAATCATTGAGCGGTCAGAATCATTAGTA AGCCAAATTACAGTTGTGCTCAACTACTTGAATCAGGATTTGCGCGAAGTTGGACTGCTTC TTGCTGATGCTCAGGCAAAACAGGATTTCGGCTTAAGAATTATTGAGGCGCAGGAAGAAG AGCGAAAAAGAGTCTCAAGAGAAATCCATGACGGACCCGCTCAAATGCTGGCGAATGTT ATGATGAGATCGGAATTAATCGAGCGGATTTTCCGTGACCGGGGCGCAGAGGACGGATTC CAAGAAATTAAAAATCTCCGCCAAATTGTTCGGAATGCCCTTTACGAAGTGGAGAAGGATT ATATATGATTTAAGACCGATGGCCCTTGATGACCTAGGCCTGATTCCAACTTTAAGAAAA TATCTATATACAACCGAGGAATATAACGGGAAGGTCAAATACATTTTCAGTGCATTGGA GAAACAGAGGATCAGAGGCTAGCGCCTCAGTTTGAGGTTGCGCTCTTCAGGCTCGCACAG GAAGCTGTGTCTAATGCGCTAAAGCATTCTGAATCTGAAGAATTACAGTCAAAGTTGAG ATCACAAAAGGATTTTGTGATTTTAATGATAAAAGATAACGGTAAAGGGGTTCGACCTGAAG |

-continued

| Strain | Gene | SEQ ID NO: | Sequence |
|---|---|---|---|
| | | | GAAGCGAAAGAGAAGAAAAACAAATCATTCGGCTTGCTGGGCATGAAAGAAAGAGTAGA<br>TTTATTGGAAGGAACGATGACAATAGATTCGAAAATAGGTCTTGGGACATTTATTATGAT<br>TAAGGTTCCGTTATCTCTTTGA |
| Paenibacillus sp. strain NRRL B-50972 | degS | 8 | GTGGACTTTCAAGCCGATATCATAGACCGAGTCATTAAGAATGCCATTCAGGTGATGGAG<br>AACAGTAAATATCAGATGTTCGAAATTTTGGACACGGCCCGGACCGAGCTGATCACATTA<br>AATCAGGAACTCCAGAGCGTCCTGAAGGAAACGGCAGAAACGATTGAAAAGGTGGACCA<br>GTTGGAAATGAACTATCGGCGGTCCCGTATTCGGCTGACTGAGGTCAGCCGTGACTTTGT<br>CCGCTATTCGGAAGAGGATATCAAGCAGGCTTACGAGAAAGCAACACAGCTTCAGCTCG<br>ATGTGATGATCTTTCGCGAGAAGGAAATGTACCTCAAGGCCAGAAGAGATGATCTTCAAA<br>AGCGGGCTAAAAGTGTCGAGGCCTCTGTCGAGCGGGCCGAAACCATCGGTTCGCAGATG<br>GGCGTCGTGCTGGAATACTTGTCGGGTGAGTTGGGACAAGTAACGCGGATCATCGAATCG<br>GCCAAAAACCGGCAGTTTATTGGTCTGAAAATTATTTTAGCCCAGGAAGAGGAGCGCAAG<br>CGGATATCCCGTGAAATTCACGATGGACCTGCACAGCTTCTTGCGCATCTAGTGCTTAGG<br>ACGGAAATTGTGGAAAGAATGATCGCCAAGCAGGAATTTAAGATGGTTCAGGACGAAAT<br>AGTAGACTTGAAGAAACAGGTTCGCTCCAGTCTTGAGGAAATGCGAAAGGTTATTTTCAA<br>TCTGCGTCCTATGGCCCTGGATGACTTGGGACTTGTTCCGACGCTCCGGAAATATGTGCAG<br>GATTTTGAAGAGAAAACGAAGATTAGATCGCTTTTTGAAACAAGGGGCAAGGAACACCG<br>TCTCTCTTCCGCGATGGAAGCAGCCATTTACCGTCTGATCCAAGAAGCTTTGACCAACGCT<br>GCCAAGCATGCTTATCCTACCTATGTGCTTGTTGAGATTACTTATCAGGCGCAGCTTGTAA<br>AAATCGTGGTGCAGGATAACGGTCTGGGCTTTAAGCCAGAGCTTTTTCAGCAGAAAAGCA<br>AAGATCATGGGCATTTTGGTCTGATTGGTATGCGGGAAAGGGTTGAACTGCTCGAGGGGA<br>GAATGGAGATCGAATCAGCTGAGAATCAAGGCACCAAGATAGTGATTCATATCCCAACC<br>AACGTGGAAAAGGGAAAGGAGTAA |

Example 4. Further Mutagenesis and Screening of Non-Mucoidal Strains

To further improve the titers of fusaricidin-like compounds, chemical treatment of *Paenibacillus* sp. strain NRRL B-67304 was performed as described in Example 1. Samples from the culture broths produced in 96-well blocks were analyzed for relative levels of fusaricidin A (see Table 7). Several isolates with increased fusaricidin production were then selected for further testing after fermentation in larger scale cultures. Samples from these larger scale cultures were again analyzed for fusaricidin A content (see Table 8), and their packed cell volumes were determined as described in Example 2 (see Table 9). Packed cell volumes were only evaluated with samples from the larger scale cultures as the cultures from the 96-well blocks did not provide sufficient volumes for these measurements.

Surprisingly, it was found that *Paenibacillus* sp. strain NRRL B-67615 not only had improved levels of fusaricidin-like compounds (see Tables 7 and 8) but also had lower levels of viscosity than *Paenibacillus* sp. strain NRRL B-67304B-67304 (see Table 9). These results further confirmed that the cellular processes related to fusaricidin biosynthesis, sporulation, and production of viscosity-producing agents are genetically separable. The lineage of *Paenibacillus* sp. strain NRRL B-67615 along with *Paenibacillus* sp. strain NRRL B-50972, *Paenibacillus* sp. strain NRRL B-67129, *Paenibacillus* sp. strain NRRL B-67304, and *Paenibacillus* sp. strain NRRL B-67306 is depicted in FIG. 1.

TABLE 7

Relative fusaricidin production of *Paenibacillus* sp. strain NRRL B-67304 and mutant strains derived from *Paenibacillus* sp. strain NRRL B-67304 cultured in 96-well blocks.

| Strain | FusA |
|---|---|
| NRRL B-67304 | 1.00 |
| Strain X | 1.62 |
| Strain Y | 1.11 |
| Strain Z | 1.22 |
| Strain AA | 1.27 |
| NRRL B-67615 | 1.15 |
| Strain AB | 1.11 |

TABLE 8

Relative fusaricidin production reported as average value ± standard deviation (n = 2) for *Paenibacillus* sp. strain NRRL B-67304 and mutant strains derived from *Paenibacillus* sp. strain NRRL B-67304 cultured at larger volumes.

| Strain | FusA |
|---|---|
| NRRL B-67304 | 1.09 ± 0.02 |
| Strain X | 1.20 ± 0.16 |
| Strain Y | 1.32 ± 0.04 |
| Strain Z | 1.35 ± 0.08 |
| Strain AA | 1.07 ± 0.02 |
| NRRL B-67615 | 1.59 ± 0.18 |
| Strain AB | 1.66 ± 0.22 |

TABLE 9

Packed cell volumes (PCV) reported as average value ± standard deviation (n = 3) for *Paenibacillus* sp. strain NRRL B-67304 and mutant strains derived from *Paenibacillus* sp. strain NRRL B-67304 cultured at larger volumes. *Paenibacillus* sp. strain Y was not evaluated in this experiment.

| Strain | PCV (%) |
|---|---|
| NRRL B-67304 | 75 ± 0 |
| Strain X | 20 ± 0 |
| Strain Z | 43 ± 6 |

TABLE 9-continued

Packed cell volumes (PCV) reported as average value ± standard deviation (n = 3) for *Paenibacillus* sp. strain NRRL B-67304 and mutant strains derived from *Paenibacillus* sp. strain NRRL B-67304 cultured at larger volumes. *Paenibacillus* sp. strain Y was not evaluated in this experiment.

| Strain | PCV (%) |
| --- | --- |
| Strain AA | 28 ± 3 |
| NRRL B-67615 | 20 ± 0 |
| Strain AB | 75 ± 0 |

The relative fusaricidin A levels, packed cell volumes, and viscosities of *Paenibacillus* sp. strain NRRL B-50972, *Paenibacillus* sp. strain NRRL B-67306 and *Paenibacillus* sp. strain NRRL B-67304, and *Paenibacillus* sp. strain NRRL B-67615 were evaluated together to confirm the improvements achieved with multiple rounds of mutagenesis and screening with the disclosed methods. The results presented in Table 10 demonstrate that the disclosed screening methods resulted in mutant derivative strains with significant improvements in fusaricidin production and lower packed cell volumes and viscosities allowing for greater concentration of the active compounds in the fermentation broths.

TABLE 10

Pack cell volumes (PCV), viscosities, and relative fusaricidin A levels reported as average value ± standard deviation (n = 3) for *Paenibacillus* sp. strain NRRL B-50972, *Paenibacillus* sp. strain NRRL B-67306, *Paenibacillus* sp. strain NRRL B-67304, and *Paenibacillus* sp. strain NRRL B-67615.

| Strain | PCV (%) | Viscosity (cP) | FusA |
| --- | --- | --- | --- |
| NRRL B-50972 | 28 ± 2 | 38.2 ± 5.4 | 1.02 ± 0.10 |
| NRRL B-67306 | 9 ± 1 | 8.0 ± 0.5 | 0.94 ± 0.07 |
| NRRL B-67304 | 15 ± 1 | 19.6 ± 3.9 | 1.97 ± 0.20 |
| NRRL B-67615 | 11 ± 1 | 9.8 ± 2.1 | 2.93 ± 0.12 |

Example 5. Comparison of Bioactivity of *Paenibacillus* sp. Strain NRRL B-50972, *Paenibacillus* Sp. Strain NRRL B-67306, *Paenibacillus* sp. Strain NRRL B-67304, and *Paenibacillus* sp. Strain NRRL B-67615

*Paenibacillus* sp. strain NRRL B-50972, *Paenibacillus* sp. strain NRRL B-67306, and *Paenibacillus* sp. strain NRRL B-67304 were cultured in a soy-based medium to produce whole broths. The whole broths were diluted in a mixture of water and organic solvent to concentrations of 2.5%, 1.25%, 0.625%, and 0.312%. The diluted whole broths were applied to young plants which were subsequently exposed to an inoculum of *Alternaria solani* (ALTESO). A chemical fungicide was included in each assay as a positive control. Several days after exposure to the inoculum of plant pathogen, each plant was scored for percent control of the pathogen relative to the untreated control plants. Each treatment was evaluated with three replicates and the average percent control was reported (see Table 11). 0% means an efficacy which corresponds to that of the untreated control, while an efficacy of 100% means that no disease is observed. *Paenibacillus* sp. strain NRRL B-67306 and *Paenibacillus* sp. strain NRRL B-67304 had superior antifungal activity compared to the *Paenibacillus* sp. strain NRRL B-50972.

TABLE 11

Control of *Alternaria solani* (ALTESO) achieved with *Paenibacillus* sp. strain NRRL B-50972, *Paenibacillus* sp. strain NRRL B-67306, and *Paenibacillus* sp. strain NRRL B-67304 at dilution rates of 2.5%, 1.25%, 0.625%, and 0.312%.

| Treatment | Application Rate | Average Percent Control |
| --- | --- | --- |
| *Paenibacillus* sp. strain NRRL B-50972 | 2.5% | 78 |
|  | 1.25% | 50 |
|  | 0.625% | 32 |
|  | 0.312% | N.E. |
| *Paenibacillus* sp. strain NRRL B-67306 | 2.5% | 92 |
|  | 1.25% | 55 |
|  | 0.625% | 12 |
|  | 0.312% | N.E. |
| *Paenibacillus* sp. strain NRRL B-67304 | 2.5% | N.E. |
|  | 1.25% | 87 |
|  | 0.625% | 70 |
|  | 0.312% | 7 |

N.E. = Not Evaluated.

The assay was repeated with *Paenibacillus* sp. strain NRRL B-67304 and *Paenibacillus* sp. strain NRRL B-67615 with the fungal pathogen *Alternaria solani* (ALTESO). This assay was performed as before except that six replicates were evaluated instead of three replicates and whole broths were applied at 1.25% or 0.625%. The average percent control resulting from the treatments is reported in Table 12. *Paenibacillus* sp. strain NRRL B-67304 and *Paenibacillus* sp. strain NRRL B-67615 produced similar levels of antifungal activity in the assay.

TABLE 12

Control of *Alternaria solani* (ALTESO) achieved with *Paenibacillus* sp. strain NRRL B-67304 and *Paenibacillus* sp. strain NRRL B-67615 at dilution rates of 1.25% and 0.625%.

| Treatment | Application Rate | Average Percent Control |
| --- | --- | --- |
| *Paenibacillus* sp. strain NRRL B-67304 | 1.25% | 90 |
|  | 0.625% | 66 |
| *Paenibacillus* sp. strain NRRL B-67615 | 1.25% | 91 |
|  | 0.625% | 74 |

Example 6. Antifungal Activity of *Paenibacillus* sp. Strain NRRL B-67306, and *Paenibacillus* Sp. Strain NRRL B-67304 and *Paenibacillus* sp. Strain NRRL B-67615 with Oomycetes Plant Pathogens

*Paenibacillus* sp. strain NRRL B-67306, *Paenibacillus* sp. strain NRRL B-67304, and *Paenibacillus* sp. strain NRRL B-67615 were cultured in a soy-based medium to produce whole broths. The whole broths were diluted in a mixture of water and organic solvent to concentrations of 10%, 5%, 2.5%, 1.25%, and 0.625%. The diluted whole broths were applied to young plants which were subsequently exposed to an inoculum of *Pseudoperonospora cubensis* (PSPECU) also known as Cucumber Downy Mildew or *Phytophthora infestans* (PHYTIN) also known as Tomato Late Blight. A chemical fungicide was included in each assay as a positive control. Several days after exposure to the inoculum of plant pathogen, each plant was scored for percent control of the pathogen relative to the untreated control plants. Each treatment was evaluated with three replicates and the average percent control was reported (see Table 13 for results with *Pseudoperonospora cubensis* and Table 14 for results with *Phytophthora infestans*). 0% means an efficacy which corresponds to that of the untreated control, while an efficacy of 100% means that no disease is observed. All three *Paenibacillus* sp. strains demonstrated consistent control of the two Oomycetes plant pathogens.

TABLE 13

Control of *Pseudoperonospora cubensis* (PSPECU) achieved with *Paenibacillus* sp. strain NRRL B-67306, *Paenibacillus* sp. strain NRRL B-67304, and *Paenibacillus* sp. strain NRRL B-67615 at dilution rates of 10%, 5%, 2.5%, 1.25%, and 0.625%.

| Treatment | Application Rate | Average Percent Control |
| --- | --- | --- |
| *Paenibacillus* sp. strain NRRL B-67306 | 10% | 92 |
| | 5% | 63 |
| | 2.5% | 50 |
| | 1.25% | 20 |
| | 0.625% | 7 |
| *Paenibacillus* sp. strain NRRL B-67304 | 10% | 100 |
| | 5% | 98 |
| | 2.5% | 92 |
| | 1.25% | 53 |
| | 0.625% | 20 |
| *Paenibacillus* sp. strain NRRL B-67615 | 10% | 100 |
| | 5% | 95 |
| | 2.5% | 70 |
| | 1.25% | 50 |
| | 0.625% | 43 |

TABLE 14

Control of *Phytophthora infestans* (PHYTIN) achieved with *Paenibacillus* sp. strain NRRL B-67306, *Paenibacillus* sp. strain NRRL B-67304, and *Paenibacillus* sp. strain NRRL B-67615 at dilution rates of 10%, 5%, 2.5%, 1.25%, and 0.625%.

| Treatment | Application Rate | Average Percent Control |
| --- | --- | --- |
| *Paenibacillus* sp. strain NRRL B-67306 | 10% | 82 |
| | 5% | 82 |
| | 2.5% | 75 |
| | 1.25% | 58 |
| | 0.625% | 50 |
| *Paenibacillus* sp. strain NRRL B-67304 | 10% | 100 |
| | 5% | 95 |
| | 2.5% | 80 |
| | 1.25% | 75 |
| | 0.625% | 60 |
| *Paenibacillus* sp. strain NRRL B-67615 | 10% | 98 |
| | 5% | 98 |
| | 2.5% | 85 |
| | 1.25% | 78 |
| | 0.625% | 75 |

Example 7. Comparison of *Paenibacillus* Strains in a Potato Field Trial Infected with Early Blight (*Alternaria solani*)

A field trial with potato plants exposed to naturally occurring Early Blight (*Alternaria solani*) was conducted. Liquid fermentation products of *Paenibacillus* sp. strain NRRL B-50972 and *Paenibacillus* sp. strain NRRL B-67306 were prepared by culturing the strains in a soy-based medium and concentrating the resulting whole broths via centrifugation and removal of the supernatants. The fermentation products were applied at 10 liters per hectare and 20 liters per hectare to plants between July 20 and August 4 at a growth stage of BBCH65 to BBCH70 as outlined in Table 16. The average incidence of disease was about 13% in untreated plants. The percent disease control shown in Table 15 is the result of the evaluation made 7 days after the final application, done by visual observation of disease symptoms. 0% means an efficacy which corresponds to that of the untreated control while an efficacy of 100% means that no disease was observed.

TABLE 15

| Product | Dosage L/ha | Application Code | Disease Control in % |
| --- | --- | --- | --- |
| Untreated Control | | | 0 |
| *Paenibacillus* sp. NRRL B-50972 | 10 | ABC | 21 |
| *Paenibacillus* sp. NRRL B-50972 | 20 | ABC | 47 |
| *Paenibacillus* sp. NRRL B-67306 | 10 | ABC | 66 |
| *Paenibacillus* sp. NRRL B-67306 | 20 | ABC | 71 |

TABLE 16

| Application Code | Application Date | Growth Stage |
| --- | --- | --- |
| A | July 20 | 65 |
| B | July 27 | 69 |
| C | August 4 | 70 |

The results in Table 15 clearly show that the observed activity of *Paenibacillus* sp. strain NRRL B-67306 was superior compared to *Paenibacillus* sp. NRRL B-50972 in this field trial.

Example 8. Comparison of *Paenibacillus* Strains in a Strawberry Field Trial Infected with Gray Mold (*Botrytis cinerea*)

A field trial with strawberry plants exposed to naturally occurring Gray Mold (*Botrytis cinerea*) was conducted. Liquid fermentation products of *Paenibacillus* sp. strain NRRL B-50972 and *Paenibacillus* sp. strain NRRL B-67304 were prepared by culturing the strains in a soy-based medium and concentrating the resulting whole broths via centrifugation and removal of the supernatants. The fermentation products were applied at 10 liters per hectare and 20 liters per hectare to plants between March 31 and April 18 at a growth stage of BBCH67 to BBCH87 as outlined in Table 18. The average incidence of disease was about 22% in untreated plants. The percent disease control shown in Table 17 is the result of the evaluation made 2 days after the final application, done by visual observation of disease symptoms. 0% means an efficacy which corresponds to that of the untreated control while an efficacy of 100% means that no disease was observed.

TABLE 17

| Product | Dosage L/ha | Application Code | Disease Control in % |
| --- | --- | --- | --- |
| Untreated Control | | | 0 |
| *Paenibacillus* sp. NRRL B-50972 | 10 | ABCD | 14 |
| *Paenibacillus* sp. NRRL B-50972 | 20 | ABCD | 0 |
| *Paenibacillus* sp. NRRL B-67304 | 10 | ABCD | 41 |

TABLE 17-continued

| Product | Dosage L/ha | Application Code | Disease Control in % |
|---|---|---|---|
| Paenibacillus sp. NRRL B-67304 | 20 | ABCD | 66 |

TABLE 18

| Application Code | Application Date | Growth Stage |
|---|---|---|
| A | March 31 | 67 |
| B | April 4 | 73 |
| C | April 11 | 85 |
| D | April 18 | 87 |

The results in Table 17 clearly show that the observed activity of *Paenibacillus* sp. strain NRRL B-67304 was superior compared to *Paenibacillus* sp. NRRL B-50972 in this field trial.

Example 9. Comparison of *Paenibacillus* Strains in a Pepper Field Trial Infected with Anthracnose (*Colletotrichum capsici*)

A field trial with pepper plants exposed to naturally occurring Anthracnose (*Colletotrichum capsici*) was conducted. Liquid fermentation products of *Paenibacillus* sp. strain NRRL B-50972 and *Paenibacillus* sp. strain NRRL B-67306 were prepared by culturing the strains in a soy-based medium and concentrating the resulting whole broths via centrifugation and removal of the supernatants. The fermentation products were applied at 10 liters per hectare and 20 liters per hectare to plants between December 28 and January 2 at a growth stage of BBCH75 as outlined in Table 20. The average incidence of disease was about 60% in untreated plants. The percent disease control shown in Table 19 is the result of the evaluation made 2 days after the final application, done by visual observation of disease symptoms. 0% means an efficacy which corresponds to that of the untreated control while an efficacy of 100% means that no disease was observed.

TABLE 19

| Product | Dosage L/ha | Application Code | Disease Control in % |
|---|---|---|---|
| Untreated Control | | | 0 |
| Paenibacillus sp. NRRL B-50972 | 10 | AB | 0 |
| Paenibacillus sp. NRRL B-50972 | 20 | AB | 6 |
| Paenibacillus sp. NRRL B-67306 | 10 | AB | 14 |
| Paenibacillus sp. NRRL B-67306 | 20 | AB | 24 |

TABLE 20

| Application Code | Application Date | Growth Stage |
|---|---|---|
| A | December 28 | 75 |
| B | January 2 | 75 |

The results in Table 19 clearly show that the observed activity of *Paenibacillus* sp. strain NRRL B-67306 was superior compared to *Paenibacillus* sp. NRRL B-50972 in this field trial.

Example 10. Identification of Growth Conditions where Viscosity Diverges for *Paenibacillus* sp. Strains NRRL B-67304 and NRRL B-67615

Figure 8A:
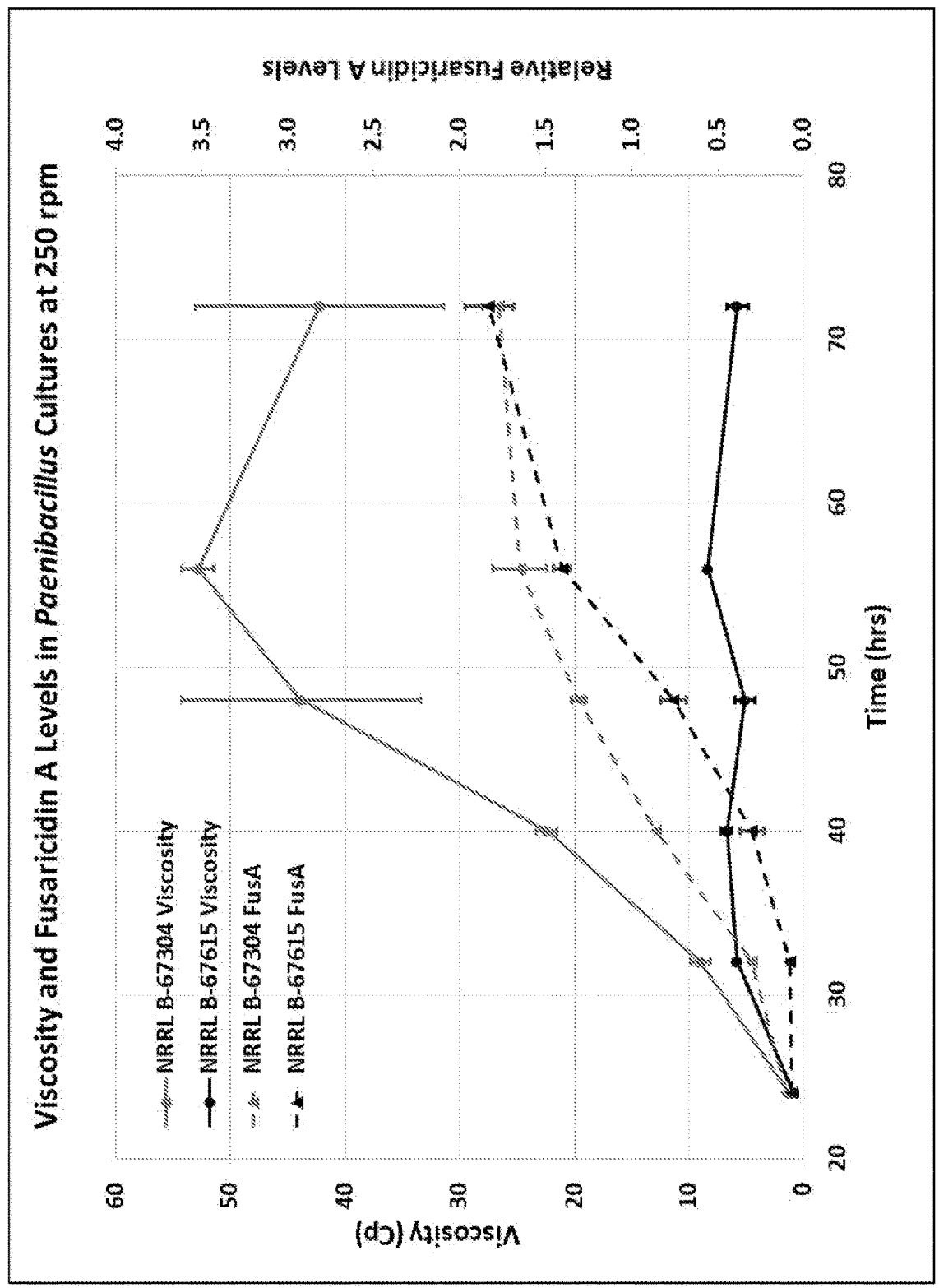
FIG. 8A depicts measurements of viscosity (solid lines) and fusaricidin A (dashed lines) in liquid cultures of *Paenibacillus* sp. strains NRRL B-67304 (Parent) and NRRL B-67615 (Progeny) grown with an agitation rate of 250 rpm over a 72 hour time period.
Figure 8B:
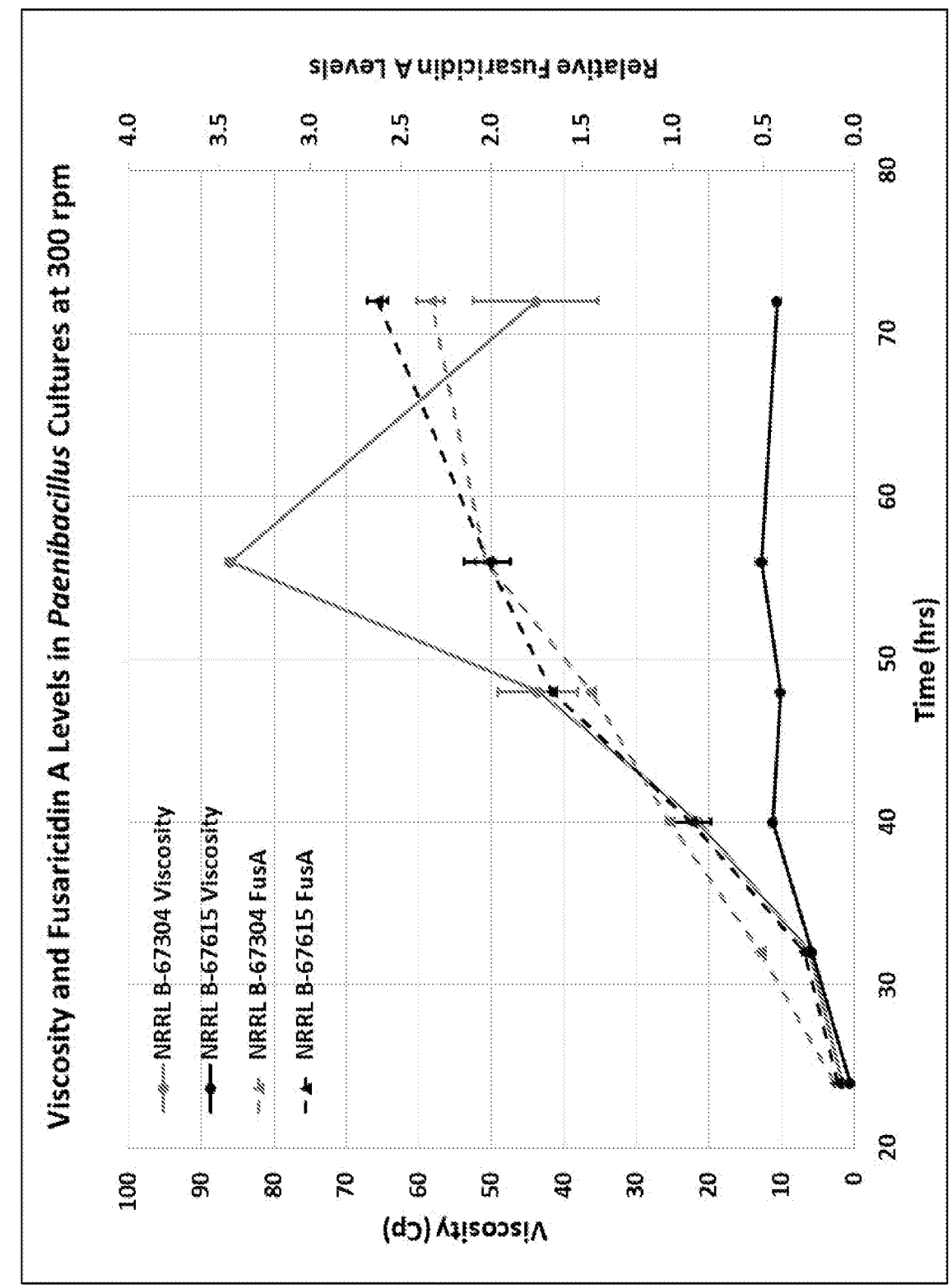
FIG. 8B depicts measurements of viscosity (solid lines) and fusaricidin A (dashed lines) in liquid cultures of *Paenibacillus* sp. strains NRRL B-67304 (Parent) and NRRL B-67615 (Progeny) grown with an agitation rate of 300 rpm over a 72 hour time period.

As shown in FIG. 1, *Paenibacillus* sp. strain NRRL B-67615 was generated by chemical mutagenesis of *Paenibacillus* sp. strain NRRL B-67304. This chemical mutagenesis resulted in *Paenibacillus* sp. strain NRRL B-67615 having significantly decreased viscosity while maintaining relatively high levels of fusaricidin A (see Table 10). To determine timepoints during liquid culture of the two strains where viscosity diverges, each strain was grown in a soy-based medium for a period of 72 hours. One group of cultures was agitated at 250 rpm and the other group at 300 rpm. Samples of each liquid culture were removed at 24 hours, 32 hours, 40 hours, 48 hours, 56 hours, and 72 hours. The viscosity and relative levels of fusaricidin A in each sample were determined as outlined in Example 4. Average values and standard deviations were determined (n=4) for the cultures grown at 250 rpm and at 300 rpm and are shown in FIGS. 8A and 8B, respectively.

Relative levels of fusaricidin A produced by each strain were comparable and increased at similar rates over the 72-hour time period. Spore production was assessed visually under the microscope in all samples, and no spores were present at any of the time points. The time points for future experiments of 40 hours and 48 hours were selected because there was a significant increase in viscosity for *Paenibacillus* sp. strain NRRL B-67304 whereas the viscosity of *Paenibacillus* sp. strain NRRL B-67615 remained relatively constant at a low level during this time (compare the solid lines showing viscosity in FIGS. 8A and 8B). Liquid cultures grown with agitation at 300 rpm were more consistent in their viscosity values, so this agitation rate was also selected for future experiments.

Example 11. Proteomic Analysis with Liquid Cultures of *Paenibacillus* sp. Strains NRRL B-67304 and NRRL B-67615

A discovery proteomics and pathway analysis approach was undertaken with *Paenibacillus* sp. strain NRRL B-67304 (parent) and *Paenibacillus* sp. strain NRRL B-67615 (progeny) to gain insight into the viscosity phenotype at the molecular level. The strains were grown in shake flasks in a soy-based medium for 40 and 48 hours to capture the diverging viscosity phenotypes of the two strains. Six replicates per condition were grown for *Paenibacillus* sp. strains NRRL B-67304 and NRRL B-67615 for a total of 24 samples. At harvest, samples were immediately frozen at −80° C. to stop growth, then sample preparation was done in batch. Protein extraction was done on total fermentations, capturing excreted and vegetative cell proteins. Total protein samples were reduced, alkylated, and trypsin-digested to produce a total peptide pool for proteomics analysis. Total peptide samples were separated by liquid chromatography and analyzed on a SCIEX 4600 TRIPLETOF® mass spectrometer, run sequentially in data-dependent (IDA) and data-independent (SWATH) acquisition modes, enabling creation of an ion library and relative quantitation across the entire peptide pool.

To create an ion library, IDA runs were first analyzed in SCIEX's Protein Pilot (5.0.1.0, 4895) software, run in thorough ID mode with false discovery rate (FDR) analysis. Then, an ion library was created in SCIEX's PeakView (2.2.0.11391) software, using the SWATH microApp (2.0.1.2133), at a 1% global protein FDR. Continuing data analysis with the SWATH microApp, relative quantitation of SWATH runs was done at 99% peptide confidence and 1% FDR thresholds. Protein Areas, as calculated from the sum intensities of 6 transitions per peptide and 6 peptides per protein, were then exported for downstream analysis. A Protein Area threshold was set at 50,000.

Of primary interest was the identification of proteins that are differentially expressed between *Paenibacillus* sp. strain NRRL B-67304 (parent) and *Paenibacillus* sp. strain NRRL B-67615 (progeny) at single time-points (40 hours or 48 hours). The goal was elucidation of protein-level differences between strains that were hypothesized to contribute to exopolysaccharide (EPS) production and the differing viscosity phenotypes. Statistical analyses were done first using SCIEX's MarkerView (1.2.1) software. Exploratory analyses, including plotting Mean 1 v. Mean 2 and Log(Fold Change) v. p-value, showed no major data abnormalities, and principal component analysis showed samples to group by strain and time. To determine differential protein expression between strains, t-tests were performed in Markerview, then p-values were adjusted for multiple comparisons in R (FDR/BH correction). Proteins were considered to be differentially expressed at P(FDR/BH-corrected)<0.05 and a minimum Fold Change=1.5. Of 442 proteins detected at 40 hours, 54 proteins met differential expression criteria (see Table 21). Of 422 proteins detected at 48 hours, 94 proteins were differentially expressed (see Table 22).

Bacterial exopolysaccharides are diverse in structure, composed of a variety of building blocks, and synthesized by various pathways. Expression also varies by strain and environment (e.g., fermentation process). For example, different strains of *Paenibacillus* have been characterized as making curdlan- and levan-type EPS, which are composed of glucose, or glucose and fructose, respectively. This initial proteomics analysis suggested that none of the proteins identified as differentially expressed in *Paenibacillus* sp. strain NRRL B-67304 (parent) and *Paenibacillus* sp. strain NRRL B-67615 (progeny) are directly involved in EPS synthesis, as identified by homology to proteins described in the literature.

Further analysis of the proteomics data was required to explain the difference in the viscosity phenotype between *Paenibacillus* sp. strains NRRL B-67304 and NRRL B-67615. To contextualize the protein-level differences seen by proteomics analysis, proteins were further annotated in KEGG (BLASTKOALA algorithm) and mapped to KEGG pathways. It was observed that several proteins involved in glycolysis and the tricarboxylic acid (TCA) cycle were significantly elevated in *Paenibacillus* sp. strain NRRL B-67615 (progeny) at the 48-hour time-point (see the underlined proteins in Table 22 under "Upregulated in Progeny"). This suggests that elevated carbohydrate metabolism occurs in *Paenibacillus* sp. strain NRRL B-67615 (progeny) as compared to *Paenibacillus* sp. strain NRRL B-67304 (parent). EPS production relies on the same hexose monomers (e.g., glucose and fructose) as primary metabolism. Thus, an increase in primary metabolism would lead to lower levels of starting substrate and a resulting decrease in EPS production and viscosity in *Paenibacillus* sp. strain NRRL B-67615 (progeny).

Conversely, where carbohydrate resources are in excess and starting substrate is abundant, EPS production and viscosity would be elevated. Consistent with this idea, two different alpha-amylase proteins were significantly elevated in *Paenibacillus* sp. strain NRRL B-67304 (parent) at 40 hours and 48 hours (see the underlined proteins in Table 21 and Table 22 under "Upregulated in Parent"). The amino acid sequences of the two amylases are shown in Table 23. These two amylases have a protein domain characteristic of the "alpha-amylase family," glycoside hydrolase family 13. See Cockburn et al., Biologia 69(6): 705-712, 2014.

Figure 9A:
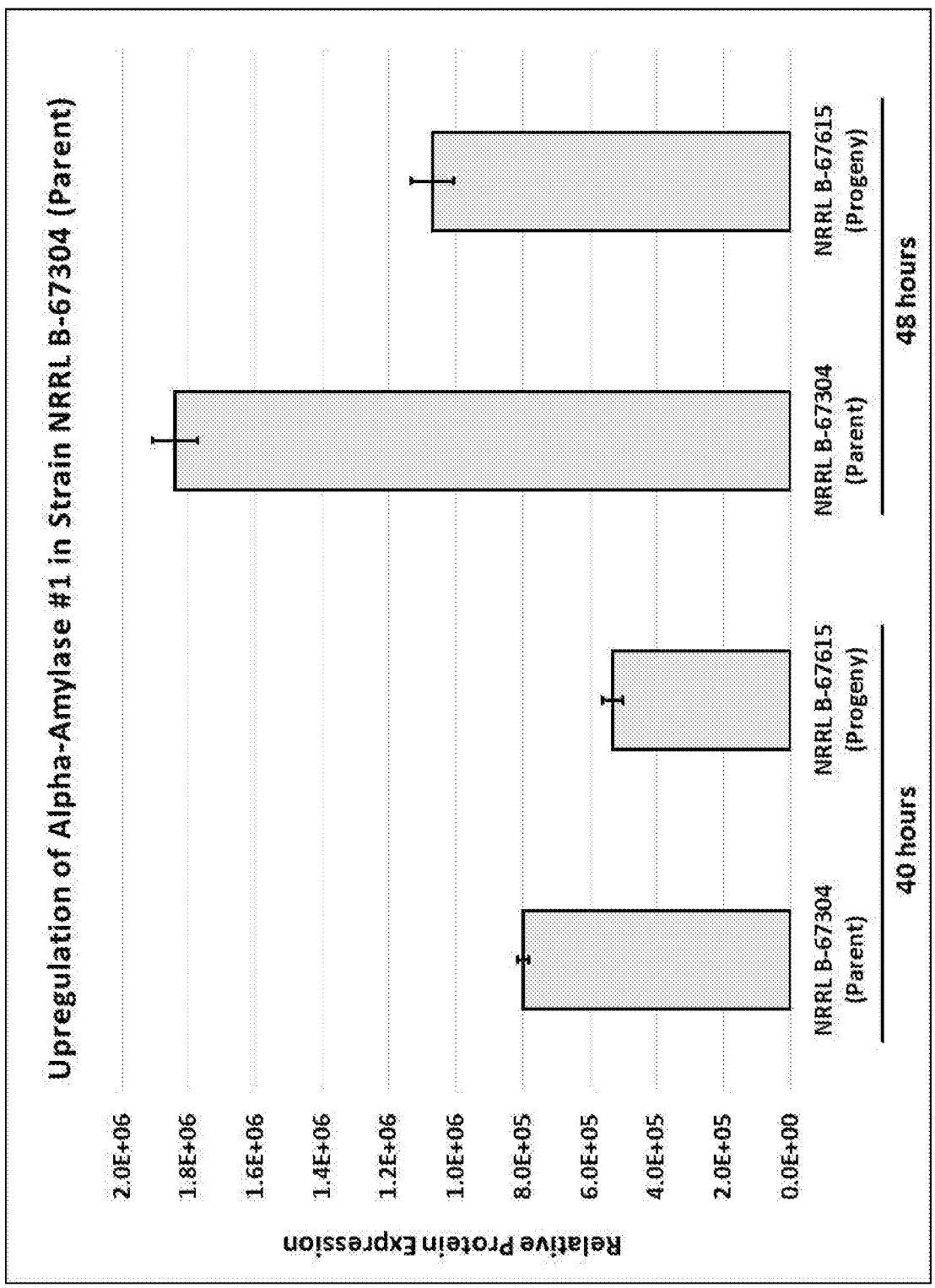
FIGS. 9A and 9B depict the relative protein expression of two alpha-amylases (i.e., "Alpha-Amylase #1" and "Alpha-Amylase #2") evaluated at the 40-hour and 48-hour timepoints in liquid cultures of *Paenibacillus* sp. strains NRRL B-67304 (Parent) and NRRL B-67615 (Progeny).
Figure 9B:
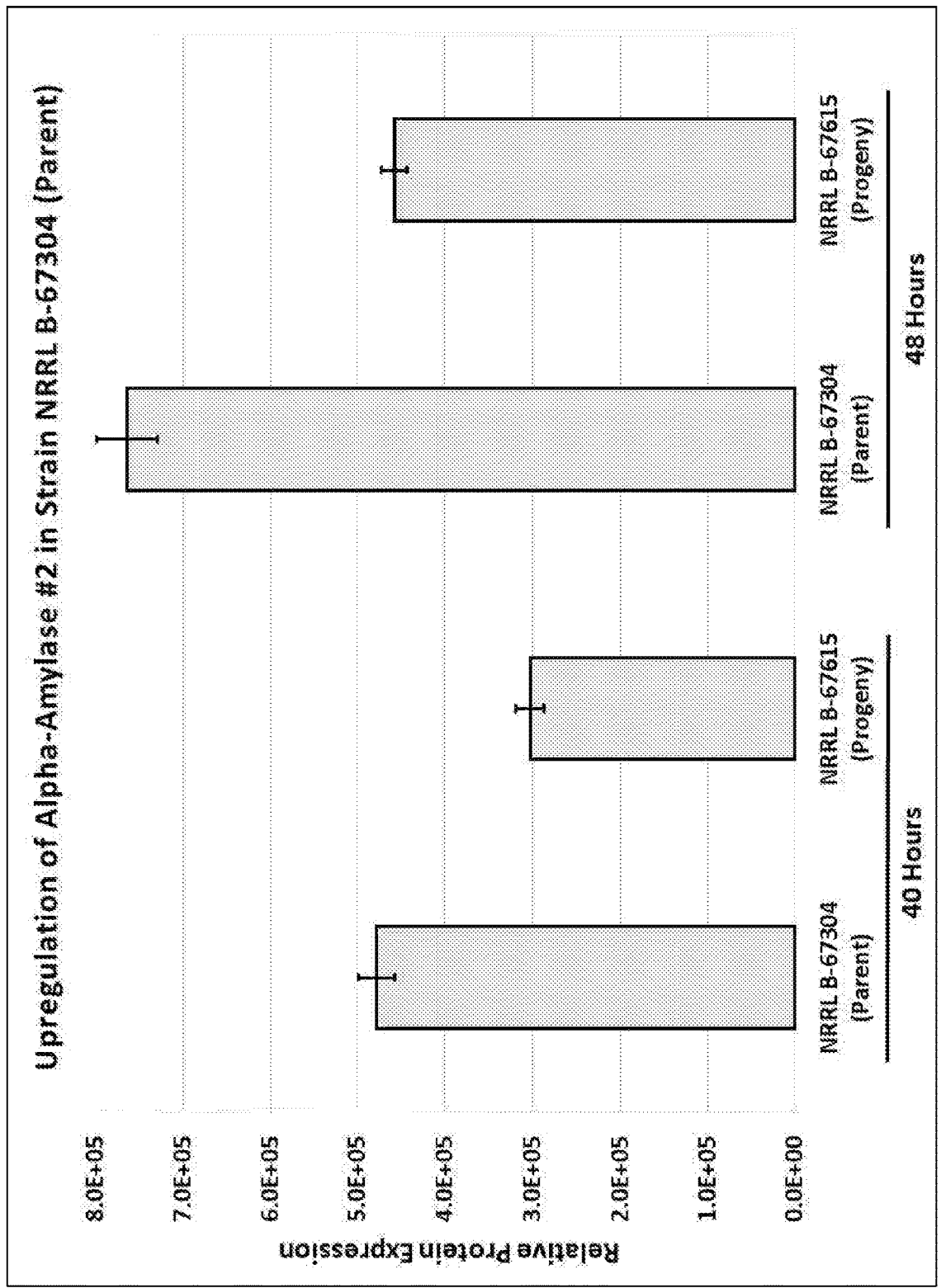
Figure 10:
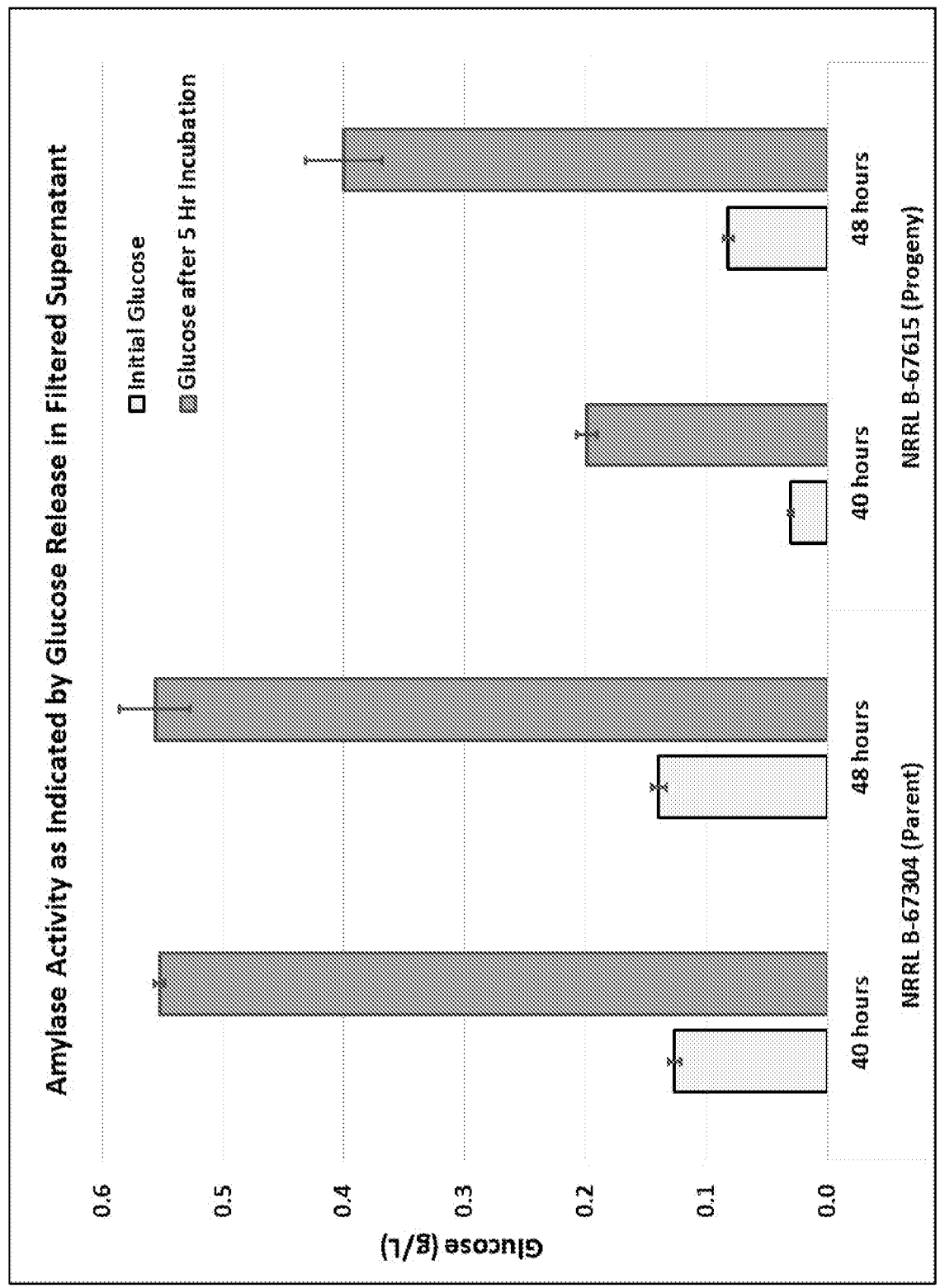
FIG. 10 depicts release of glucose from polysaccharides in the culture medium as an indicator of amylase activity in cell-free supernatants from liquid cultures of *Paenibacillus* sp. strains NRRL B-67304 (Parent) and NRRL B-67615 (Progeny).
Figure 11:
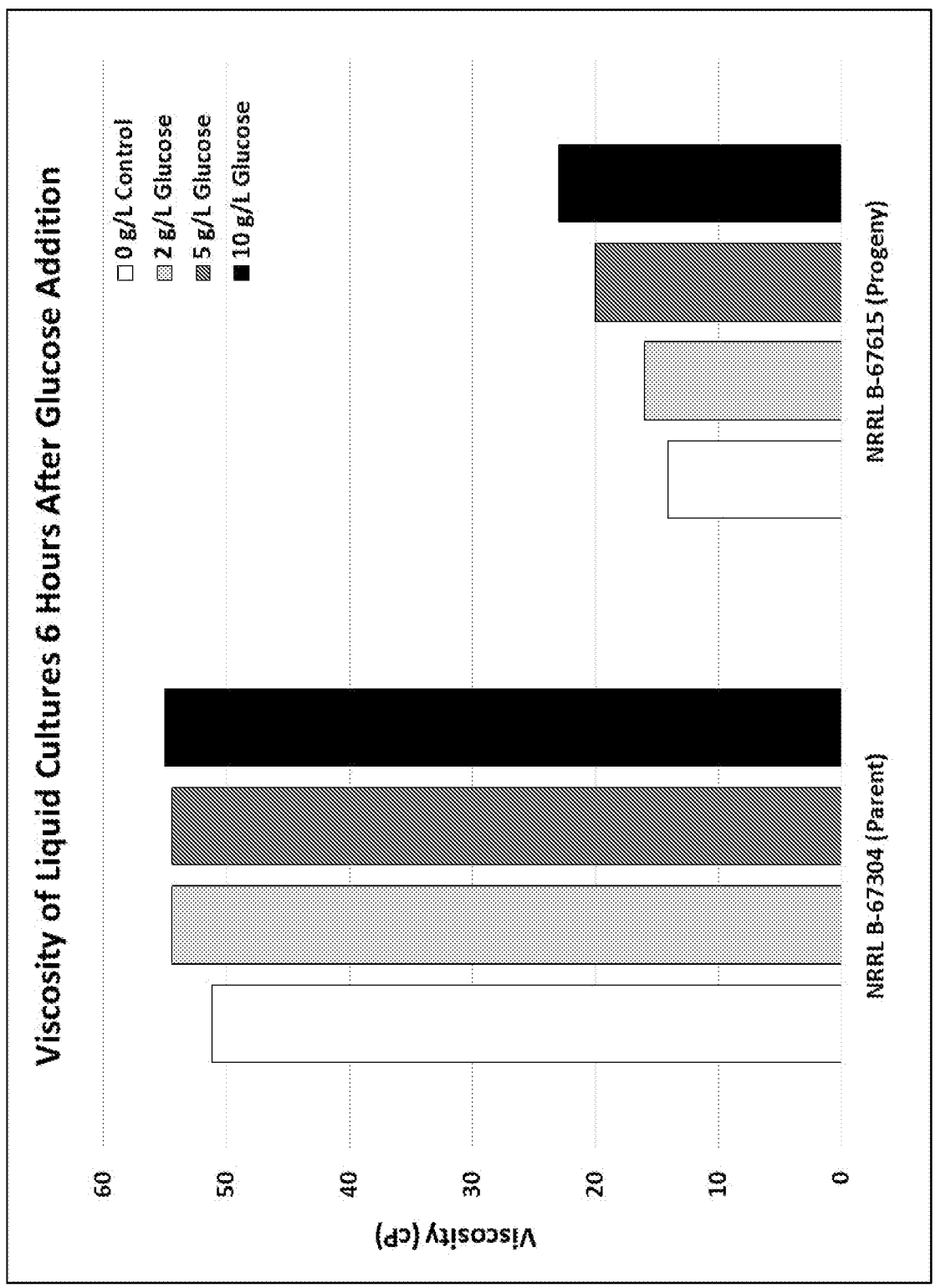
FIG. 11 depicts viscosity measurements of liquid cultures of *Paenibacillus* sp. strains NRRL B-67304 (Parent) and NRRL B-67615 (Progeny) supplemented with 0 g/L glucose (i.e., control), 2 g/L glucose, 5 g/L glucose, or 10 g/L glucose at the 40-hour timepoint and allowed to continue growth for 6 hours.

The relative expression of the two alpha-amylases (i.e., "Alpha-Amylase #1" and "Alpha-Amylase #2") was quantified with samples taken at the 40-hour and 48-hour time-points and is presented in FIGS. 9A and 9B. The relative protein quantification demonstrates that *Paenibacillus* sp. strain NRRL B-67304 (parent) consistently expresses significantly more alpha-amylase than *Paenibacillus* sp. strain NRRL B-67615 (progeny). Without wishing to be bound to any theory, the soy-based culture medium in which the strains are grown contains polysaccharides that these amylases convert to hexose monomers required for EPS production. Abundant substrate may then drive EPS production and the increased viscosity in liquid cultures of *Paenibacillus* sp. strain NRRL B-67304 (parent).

TABLE 21

Differentially expressed proteins in *Paenibacillus* sp. strain NRRL B-67304 (parent) and *Paenibacillus* sp. strain NRRL B-67615 (progeny) at 40 hrs [t-test, P(FDR/BH-corrected) < 0.05; minimum Fold Change = 1.5]. The protein levels of two alpha-amylases (underlined) are significantly increased in *Paenibacillus* sp. strain NRRL B-67304 (parent)

| Protein Annotation | KEGG Orthology |
| --- | --- |
| Upregulated in Parent | |
| bacillolysin | K01400 |
| glycine cleavage system protein H | K02437 |
| 3-ketoacyl-ACP reductase | K00059 |
| cellulose 1,4-beta-cellobiosidase | |
| alpha-amylase | |
| serine protease | K13276 |
| serine protease | K13276 |
| hypothetical protein | |
| hypothetical protein | |
| ABC transporter substrate-binding protein | K02035 |
| type I glutamate-ammonia ligase | K01915 |
| glycine dehydrogenase (aminomethyl-transferring) | K00282 |
| glycine dehydrogenase (aminomethyl-transferring) | K00283 |

TABLE 21-continued

Differentially expressed proteins in *Paenibacillus* sp. strain NRRL B-67304 (parent) and *Paenibacillus* sp. strain NRRL B-67615 (progeny) at 40 hrs [t-test, P(FDR/BH-corrected) < 0.05; minimum Fold Change = 1.5]. The protein levels of two alpha-amylases (underlined) are significantly increased in *Paenibacillus* sp. strain NRRL B-67304 (parent)

| Protein Annotation | KEGG Orthology |
|---|---|
| 1,4-beta-glucanase | K01179 |
| glutamate dehydrogenase | K00262 |
| alpha-amylase | |
| 5-methyltetrahydropteroyltriglutamate-homocysteine methyltransferase | |
| Upregulated in Progeny | |
| MULTISPECIES: aspartate 1-decarboxylase | K01579 |
| N-acetyltransferase | |
| MULTISPECIES: cold-shock protein | K03704 |
| MULTISPECIES: translation elongation factor Ts | K02357 |
| MULTISPECIES: DNA-directed RNA polymerase subunit alpha | K03040 |
| sugar ABC transporter substrate-binding protein | K17244 |
| glutamate synthase subunit alpha | K00284 |
| non-ribosomal peptide synthetase | |
| 3-methyl-2-oxobutanoate hydroxymethyltransferase | K00606 |
| aminotransferase | K05825 |
| nucleotide exchange factor GrpE | K03687 |
| phosphomethylpyrimidine synthase ThiC | K03147 |
| 50S ribosomal protein L25 | K02897 |
| class II fumarate hydratase | K01679 |
| MULTISPECIES: histidine triad nucleotide-binding protein | K02503 |
| spore coat protein | K00973 |
| 6-phospho-3-hexuloisomerase | K08094 |
| 3-hexulose-6-phosphate synthase | K08093 |
| phosphoglycerate kinase | K00927 |
| hypothetical protein | |
| UDP-glucose 6-dehydrogenase | K00012 |
| oxidoreductase | |
| UDP-glucosyltransferase | |
| diaminobutyrate-2-oxoglutarate transaminase | K00836 |
| aldehyde dehydrogenase | |
| threonine-tRNA ligase | K01868 |
| hypothetical protein | |
| copper amine oxidase | |
| histidinol-phosphate transaminase | K00817 |
| pyruvate synthase | K00169 |
| hypothetical protein | |
| response regulator | K02490 |
| sigma-54 modulation protein | K05808 |
| phage-shock protein | K03969 |
| hypothetical protein | |
| MULTISPECIES: 2',3'-cyclic-nucleotide 2'-phosphodiesterase | K01119 |
| transcriptional regulator | |

TABLE 22

Differentially expressed proteins in *Paenibacillus* sp. strain NRRL B-67304 (parent) and *Paenibacillus* sp. strain NRRL B-67615 (progeny) at 48 hrs [t-test, P(FDR/BH-corrected) < 0.05; minimum Fold Change = 1.5]. The protein levels of two alpha-amylases (underlined) are significantly increased in *Paenibacillus* sp. strain NRRL B-67304 (parent). Several enzymes involved in glycolysis or the tricarboxylic acid (TCA) cycle (underlined) are upregulated in *Paenibacillus* sp. strain NRRL B-67615 (progeny).

| Protein Annotation | KEGG Orthology |
|---|---|
| Upregulated in Parent | |
| bacillolysin | K01400 |
| glycine cleavage system protein H | K02437 |
| thioredoxin-disulfide reductase | K00384 |
| sulfate transporter subunit | K02048 |
| glutamine-fructose-6-phosphate transaminase (isomerizing) | K00820 |
| methionine ABC transporter substrate-binding protein | K02073 |
| cellulose 1,4-beta-cellobiosidase | |
| alpha-amylase | |
| ABC transporter substrate-binding protein | K15580 |
| IMP dehydrogenase | K00088 |
| L-asparaginase | K01424 |
| acetyltransferase | |
| serine protease | K13276 |
| serine protease | K13276 |
| hypothetical protein | |
| hypothetical protein | |
| DNA-binding protein | |
| ABC transporter substrate-binding protein | K02035 |
| glycine dehydrogenase (aminomethyl-transferring) | K00283 |
| hypothetical protein | |

TABLE 22-continued

Differentially expressed proteins in *Paenibacillus* sp. strain NRRL
B-67304 (parent) and *Paenibacillus* sp. strain NRRL B-67615
(progeny) at 48 hrs [t-test, P(FDR/BH-corrected) < 0.05;
minimum Fold Change = 1.5]. The protein levels of two alpha-
amylases (underlined) are significantly increased in *Paenibacillus*
sp. strain NRRL B-67304 (parent). Several enzymes involved in
glycolysis or the tricarboxylic acid (TCA) cycle (underlined) are
upregulated in *Paenibacillus* sp. strain NRRL B-67615 (progeny).

| Protein Annotation | KEGG Orthology |
|---|---|
| 1,4-beta-glucanase | K01179 |
| glutamate dehydrogenase | K00262 |
| alpha-amylase | |
| Upregulated in Progeny | |
| non-ribosomal peptide synthetase, partial | K15662 |
| MULTISPECIES: aspartate 1-decarboxylase | K01579 |
| N-acetyltransferase | |
| MULTISPECIES: cold-shock protein | K03704 |
| MULTISPECIES: translation elongation factor Ts | K02357 |
| oxidoreductase | |
| hypothetical protein | |
| MULTISPECIES: adenylosuccinate lyase | K01756 |
| aldo/keto reductase | |
| glutamate synthase subunit alpha | K00284 |
| glucose-6-phosphate isomerase | K01810 |
| ketol-acid reductoisomerase | K00053 |
| isocitrate dehydrogenase (NADP(+)) | K00031 |
| succinate-CoA ligase subunit alpha | K01902 |
| 3-methyl-2-oxobutanoate hydroxymethyltransferase | K00606 |
| bifunctional acetaldehyde-CoA/alcohol dehydrogenase | K04072 |
| aminotransferase | K05825 |
| nucleotide exchange factor GrpE | K03687 |
| HPr family phosphocarrier protein | K11189 |
| UDP-4-amino-4,6-dideoxy-N-acetyl-beta-L-altrosamine transaminase | |
| phosphomethylpyrimidine synthase ThiC | K03147 |
| phosphoenolpyruvate-protein phosphotransferase | K08483 |
| hypothetical protein | |
| major virion structural protein | |
| MULTISPECIES: hypothetical protein | |
| class II fumarate hydratase | K01679 |
| hypothetical protein | |
| terminase | |
| hypothetical protein | |
| phage portal protein | |
| phage portal protein | |
| MULTISPECIES: ATP-dependent Clp protease proteolytic subunit | K01358 |
| MULTISPECIES: histidine triad nucleotide-binding protein | K02503 |
| spore coat protein | K00973 |
| 6-phospho-3-hexuloisomerase | K08094 |
| 3-hexulose-6-phosphate synthase | K08093 |
| hypothetical protein | |
| hypothetical protein | |
| hypothetical protein | |
| peptidase M23 | |
| polyribonucleotide nucleotidyltransferase | K00962 |
| succinate-CoA ligase subunit beta | K01903 |
| phosphoglycerate kinase | K00927 |
| UDP-glucose 6-dehydrogenase | K00012 |
| hypothetical protein | |
| baseplate assembly protein J | |
| hypothetical protein | |
| hypothetical protein | |
| oxidoreductase | |
| UDP-glucosyltransferase | |
| diaminobutyrate-2-oxoglutarate transaminase | K00836 |
| aldehyde dehydrogenase | |
| serine hydroxymethyltransferase | K00600 |
| hypothetical protein | |
| threonine-tRNA ligase | K01868 |
| hypothetical protein | |
| copper amine oxidase | |
| histidinol-phosphate transaminase | K00817 |
| response regulator | K02490 |
| ATP-dependent Clp protease ATP-binding subunit ClpC | K03696 |
| formate acetyltransferase | K00656 |
| L-lactate dehydrogenase | K00016 |
| type I glutamate-ammonia ligase | K01915 |
| glycosyl hydrolase | |
| molecular chaperone GroEL | K04077 |
| hypothetical protein | |
| phage-shock protein | K03969 |
| amylopullulanase alpha-amylase/pullulanase | |
| malate dehydrogenase | K00024 |
| MULTISPECIES: dTDP-glucose 4,6-dehydratase | K01710 |
| transcriptional regulator | |

| Strains | Protein | SEQ ID NO: | Sequence |
|---|---|---|---|
| *Paenibacillus* sp. strains NRRL B-67304 and NRRL B-67615 | alpha-amylase | 9 | MTRNKCLRRLSTAMLTVPMLTMFASGAMAEQEMNGHKPPVSTGSGVFYEIYINSFYDSNGD GHGDLKGITQKLDYLNDGNPRSGKDLQISGLWLMPLNPSPSYHKYDVTDYYQVDPQYGNLN DFRTLMKEADRKGIKVIMDLVINHSSSEHPWFKEGSVNPQSKYHDYYVWADKNTDLDEKGS WGQQVWHKNPNGEGYFYGTFWSGMPDLNFDNLEVRKEMIKVGKYWLQQGADGFRLDAA MHIFKGQTKEGADKNIAWWNEFRSEMEKVNPNVYLAGEVWDKPETIAPYYGPLHSLFNFDL GGTILNSIKNGQDQGIATFAEKTLKLYKSYNKAALDAPFLSNHDQTRVMSELGGDVRKAKLA ASILLTLPGQPFLYYGEEIGMKGEKPDEYLREPMRWYKGDGPGQTTWEEPKYNTGEVSVEAQ LRDDDSLLESYRSLIRLREEHEALRSDSLEPIQAGSASVTAFKRTSGKETLYVYHNLSGEPVTL QIKDWDKGKWKVVFSTSKDMKVKKGTVVIPAYGSLITKEDRKS |
| *Paenibacillus* sp. strains NRRL B-67304 and NRRL B-67615 | alpha-amylase | 10 | MLGKKTGSFISWLIILSLCFNFFGLPGVASASSTDYTATYTNSTATTLPSTTASITSTVTATYAP TTIPKSTQTGLTVHFKKPSSWNSAIRIHYWNLNPTTVPISGAWPGILMKSDGNDWYSYTIAEATG SSLIFNDGSGKQTADLSRSVKEGWYYTDNTWYDTSPEMPKIPAISASPVPKTYDSSQSVTLSST NSDDKIYYTIDGSTPTTSSTLYTSPIQVASSLTIKAFGVNSIGQTGNASSFAYMIDLNSDLQAPT ITANLPTRHSDSSVTVSFNLNDNKAATTKAYYTDDGTEPTISSKVYILGNAMAGLTGPSILISKT TTLKFLVIDGAGNQTKQSFVYNIGNKGDFREDTIYFVITSRFYDGDPSNNMHAWDDAKARNP DSDPAWRGDFKGLIQKLDYIKALGFSAVWITPVVQNASGYDYHGYHAINFAKVDPRYESAGA SYQDLINAAHAKGLKVIQDIVVNHTGNFGEENLYPMFKKDPAKPDTANNLVKTTDKLPSNYD TMTPDQQYQARLALMKNAETNNNIYHTEKSLSWESYTVQTGQIAGDCVDLNTENPAVNEYLI DTYNHYIDMGVDAFRVDTVKHVSRYIFNKYYIPAWKTRGGSDFYIFGEVATRYRDVWNSGIP |

| Strains | Protein | SEQ ID NO: | Sequence |
|---|---|---|---|
| | | | AISTPFYTWKSSKSYPGDGKNDYASNKVSVEQEWADNSTTAGQPTSNNALLNGNTYHTPDYS MKSGMDVIDFPMHWAFKTAQEAFNMRSGDQYYNDATWNVTYIDSHDYAPDQAPENQRFAG TQDTWAENLDLMFTFRGIPAIFYGSEIEFQKGAVIDPGPNAPLSKTGRAYFGDHMEGNVTVQD YGKYTNATGTLAESLNHPLAKHIRQLNLIRRAVPALQKGQYSTENVTGNLAFKRRYTDSAKG IDSFALVTISGNATFTGIPNGTYVDAVTGNSKTVTDGKITLTCSGKGNARVYVLNGSGGIGETG TYLK |

Example 12. Confirmation of Increased Amylase Activity with *Paenibacillus* sp. Strain NRRL B-67304 (Parent)

To confirm that liquid cultures of *Paenibacillus* sp. strain NRRL B-67304 (parent) have greater levels of amylase activity than those of *Paenibacillus* sp. strain NRRL B-67615 (progeny) both strains were grown in a soy-based medium and samples were removed at 40 hours and 48 hours. The samples were centrifuged, and the supernatants retained and sterile filtered to remove all cells and leave cellular proteins including amylases and unspent polysaccharides from the medium. Any amylases in the supernatant will continue to break down the polysaccharides and generate glucose. The amount of glucose was measured in these cell-free supernatants initially and after a 5-hour incubation at 28° C.

The glucose measurements presented in FIG. 10 confirm that *Paenibacillus* sp. strain NRRL B-67304 (parent) has greater levels of amylase activity than does *Paenibacillus* sp. strain NRRL B-67615 (progeny) when the strains are grown under similar conditions.

Example 13. Addition of Glucose to Liquid Cultures of *Paenibacillus* sp. Strains NRRL B-67304 and NRRL B-67615

If the availability of hexose monomers (e.g., glucose, fructose) in liquid cultures of the *Paenibacillus* sp. strains were limiting for EPS production which contributes to the viscosity of these cultures, then addition of glucose to the cultures should result in increased EPS production and viscosity, and this effect would be most pronounced for *Paenibacillus* sp. strain NRRL B-67615 (progeny). To test this hypothesis liquid cultures of *Paenibacillus* sp. strain NRRL B-67615 (progeny) and *Paenibacillus* sp. strain NRRL B-67304 (parent) were augmented with 0 g/L glucose (i.e., control), 2 g/L glucose, 5 g/L glucose, or 10 g/L glucose at the 40-hour timepoint. The control and glucose-supplemented liquid cultures were allowed to continue growing for 6 hours, at which time the viscosity and residual glucose concentration in each culture were determined.

In all the cultures except those supplemented with 10 g/L glucose, the residual glucose concentrations were nearly 0 g/L showing that the added glucose was consumed by the cells. The viscosity measurements of the cultures are presented in FIG. 11. The addition of glucose to *Paenibacillus* sp. strain NRRL B-67304 (parent) cultures had little effect on viscosity presumably because of its high levels of amylase activity and the resulting abundant glucose available from the culture medium. In contrast, glucose-supplemented cultures of *Paenibacillus* sp. strain NRRL B-67615 (progeny) increased in viscosity with greater viscosity resulting from increasing amounts of added glucose (see the bars on the right side of FIG. 11).

Overall, the experimental results demonstrate that amylase expression and activity are lower in *Paenibacillus* sp. strain NRRL B-67615 (progeny) compared to *Paenibacillus* sp. strain NRRL B-67304 (parent) resulting in fewer simple sugars (e.g., glucose) for EPS production and the low viscosity phenotype.

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a biologically pure culture of a fusaricidin-producing *Paenibacillus* sp. strain comprising a mutant DegU lacking a functional receiver domain or a functional DNA binding domain and/or a mutant DegS lacking a functional single binding domain or a functional ATPase domain,
wherein the mutant DegU and/or the mutant DegS result in a liquid culture of the *Paenibacillus* sp. strain with decreased viscosity compared to a liquid culture of a *Paenibacillus* sp. strain comprising a wild-type DegU and a wild-type DegS.

2. The composition according to claim 1, wherein the mutant DegU and/or the mutant DegS inhibit the formation of colonies of the *Paenibacillus* sp. strain with a mucoid morphology.

3. The composition according to claim 1, wherein the mutant DegU and/or the mutant DegS is a knockout or is truncated as a result of a premature stop codon.

4. The composition according to claim 3, wherein the premature stop codon results in a mutant DegU truncated at position 218 numbered by correspondence with the amino acid sequence of SEQ ID NO: 2.

5. The composition according to claim 1 wherein the mutant DegU comprises an amino acid substitution of a small residue to an acidic residue at position 109 numbered by correspondence with the amino acid sequence of SEQ ID NO: 2; and/or a small residue to a polar residue at position 228 numbered by correspondence with the amino acid sequence of SEQ ID NO: 2; and/or an acidic residue to a polar residue at position 63 numbered by correspondence with the amino acid sequence of SEQ ID NO: 2; and/or a polar residue to a small residue at position 195 numbered by correspondence with the amino acid sequence of SEQ ID NO: 2; and/or a hydrophobic residue to a small residue at position 204 numbered by correspondence with the amino acid sequence of SEQ ID NO: 2; and/or a polar residue to a small residue at position 208 numbered by correspondence with the amino acid sequence of SEQ ID NO: 2; and/or a basic residue to a small residue at position 212 numbered by correspondence with the amino acid sequence of SEQ ID NO: 2; and/or a hydrophobic residue to a small residue at position 217 numbered by correspondence with the amino acid sequence of SEQ ID NO: 2; and/or a basic residue to a small residue at position 207 numbered by correspondence with the amino acid sequence of SEQ ID NO: 2; and/or a polar residue to a small residue at position 211 numbered by correspondence with the amino acid sequence of SEQ ID NO: 2; and/or a polar residue to a small residue at position 214 numbered by correspondence with the amino acid sequence of SEQ ID NO: 2.

6. The composition according to claim 1 wherein the mutant DegU comprises SEQ ID NO: 2 with an amino acid substitution of G109D and/or A228T and/or D63N and/or N195A and/or I204A and/or T208A and/or H212A and/or L217A and/or K207A and/or N211A and/or S214A; or a variant thereof having a conservative amino acid substitution.

7. The composition according to claim 1, wherein the mutant DegS comprises an amino acid substitution of a hydrophobic residue to an aromatic residue at position 99 numbered by correspondence with the amino acid sequence of SEQ ID NO: 4 and/or an acidic residue to a basic residue at position 294 numbered by correspondence with the amino acid sequence of SEQ ID NO: 4; and/or a polar residue to a small residue at position 73 numbered by correspondence with the amino acid sequence of SEQ ID NO: 4; and/or a small residue to a hydrophobic residue at position 190 numbered by correspondence with the amino acid sequence of SEQ ID NO: 4.

8. The composition according to claim 1, wherein the mutant DegS comprises SEQ ID NO: 4 with an amino acid substitution of L99F and/or E294K and/or T73A and/or A190V; or a variant thereof having a conservative amino acid substitution.

9. The composition according to claim 1, wherein the *Paenibacillus* sp. strain is a mutagenized derivative strain and demonstrates increased fusaricidin levels compared to a non-mutagenized parental strain.

10. The composition according to claim 1, wherein the *Paenibacillus* sp. strain is a mutagenized derivative strain and demonstrates decreased amylase expression and/or enzymatic activity compared to a non-mutagenized parental strain.

11. The composition according to claim 10, wherein the decreased amylase expression and/or enzymatic activity occurs with an alpha-amylase protein comprising a sequence with greater than about 90% sequence identity to SEQ ID NO: 9 or SEQ ID NO: 10.

12. The composition according to claim 9, wherein the non-mutagenized parental strain is *Paenibacillus* sp. strain NRRL B-50972, *Paenibacillus* sp. strain NRRL B-67129, *Paenibacillus* sp. strain NRRL B-67304, *Paenibacillus* sp. strain NRRL B-67306, or *Paenibacillus* sp. strain NRRL B-67615.

13. The composition according to claim 1, wherein the *Paenibacillus* sp. strain is *Paenibacillus* sp. strain NRRL B-67304, *Paenibacillus* sp. strain NRRL B-67306, *Paenibacillus* sp. strain NRRL B-67615, or a fungicidal mutant strain thereof.

14. The composition according to claim 13, wherein the fungicidal mutant strain has a genomic sequence with greater than about 90% sequence identity to *Paenibacillus* sp. strain NRRL B-67304, *Paenibacillus* sp. strain NRRL B-67306, or *Paenibacillus* sp. strain NRRL B-67615.

15. A method of treating a plant to control a disease, wherein the method comprises applying an effective amount of a composition of claim 1 to a part of the plant and/or to a locus of the plant, wherein the disease is a plant disease caused by a fungus selected from the group consisting of *Alternaria alternata, Alternaria solani, Botrytis cinerea, Colletotrichum lagenarium, Erysiphe necator, Fusarium culmorum, Phaeosphaeria nodorum, Zymoseptoria tritici, Phytophthora cryptogea, Phytophthora infestans, Plasmopara viticola, Podosphaera leucotricha, Pseudoperonospora cubensis, Pythium ultimum, Magnaporthe oryzae, Sphaerotheca fuliginea, Thanatephorus cucumeris, Ustilago segetum* var. *avenae, Uromyces appendiculatus,* and *Puccinia triticina* or a plant disease caused by a bacteria selected from the group consisting of *Xanthomonas campestris, Pseudomonas syringae,* and *Erwinia carotovora.*

16. The method according to claim 15, wherein the composition is applied at about $1\times10^4$ to about $1\times10^{14}$ colony forming units (CFU) per hectare.

17. A method of treating a plant to control a disease, wherein the method comprises applying an effective amount of a composition of claim 1 to a part of the plant and/or to a locus of the plant, wherein the disease is a plant disease selected from the group consisting of powdery mildew and downy mildew.

18. A composition comprising a biologically pure culture of a fusaricidin-producing *Paenibacillus* sp. strain comprising a mutant DegU lacking a functional receiver domain or a functional DNA binding domain and/or a mutant DegS lacking a functional single binding domain or a functional ATPase domain, wherein the mutant DegU comprises a mutation in the receiver domain or the DNA binding domain and/or the mutant DegS comprises a mutation in the single binding domain or the ATPase domain and results in a liquid culture of the *Paenibacillus* sp. strain with decreased viscosity compared to a liquid culture of a *Paenibacillus* sp. strain comprising a wild-type DegU having the amino acid sequence according to SEQ ID NO: 2 and a wild-type DegS having the amino acid sequence according to SEQ ID NO: 4, wherein the strain comprising a wild-type DegU and DegS is a parental strain of the fusaricidin-producing *Paenibacillus* sp. strain comprising the mutant DegU and/or DegS.

\* \* \* \* \*

SEQUENCE LISTING

```
<160> NUMBER OF SEQ ID NOS: 10

<210> SEQ ID NO 1
<211> LENGTH: 229
<212> TYPE: PRT
<213> ORGANISM: Bacillus subtilis

<400> SEQUENCE: 1

Met Thr Lys Val Asn Ile Val Ile Ile Asp Asp His Gln Leu Phe Arg
1               5                   10                  15
```

```
Glu Gly Val Lys Arg Ile Leu Asp Phe Glu Pro Thr Phe Glu Val Val
            20                  25                  30

Ala Glu Gly Asp Asp Gly Asp Glu Ala Ala Arg Ile Val Glu His Tyr
        35                  40                  45

His Pro Asp Val Val Ile Met Asp Ile Asn Met Pro Asn Val Asn Gly
 50                  55                  60

Val Glu Ala Thr Lys Gln Leu Val Glu Leu Tyr Pro Glu Ser Lys Val
 65                  70                  75                  80

Ile Ile Leu Ser Ile His Asp Asp Glu Asn Tyr Val Thr His Ala Leu
                85                  90                  95

Lys Thr Gly Ala Arg Gly Tyr Leu Leu Lys Glu Met Asp Ala Asp Thr
            100                 105                 110

Leu Ile Glu Ala Val Lys Val Val Ala Glu Gly Gly Ser Tyr Leu His
        115                 120                 125

Pro Lys Val Thr His Asn Leu Val Asn Glu Phe Arg Arg Leu Ala Thr
    130                 135                 140

Ser Gly Val Ser Ala His Pro Gln His Glu Val Tyr Pro Glu Ile Arg
145                 150                 155                 160

Arg Pro Leu His Ile Leu Thr Arg Arg Glu Cys Glu Val Leu Gln Met
                165                 170                 175

Leu Ala Asp Gly Lys Ser Asn Arg Gly Ile Gly Glu Ser Leu Phe Ile
            180                 185                 190

Ser Glu Lys Thr Val Lys Asn His Val Ser Asn Ile Leu Gln Lys Met
        195                 200                 205

Asn Val Asn Asp Arg Thr Gln Ala Val Val Ala Ile Lys Asn Gly
    210                 215                 220

Trp Val Glu Met Arg
225

<210> SEQ ID NO 2
<211> LENGTH: 240
<212> TYPE: PRT
<213> ORGANISM: Paenibacillus sp.

<400> SEQUENCE: 2

Met Glu Asn Gln Glu Ile Ser Asn Ala Pro Ile Lys Val Leu Leu Ala
 1               5                  10                  15

Asp Asp His Gln Leu Phe Arg Glu Gly Leu Lys Arg Ile Leu Asn Met
            20                  25                  30

Glu Asp Asp Ile Glu Val Ile Gly Glu Cys Gly Asp Gly Ile Gln Val
        35                  40                  45

Leu Glu Phe Cys Asn Val Glu Lys Pro Asp Ile Val Leu Met Asp Ile
 50                  55                  60

Asn Met Pro Ile Glu Asn Gly Val Glu Ala Thr Glu Lys Leu Arg Glu
 65                  70                  75                  80

Met Phe Pro Asp Val Lys Val Ile Ile Leu Ser Ile His Asp Asp Glu
                85                  90                  95

Ser Tyr Val Phe Glu Thr Leu Arg Lys Gly Ala Asn Gly Tyr Leu Leu
            100                 105                 110

Lys Asp Met Glu Ala Glu Ser Leu Ile Asn Ala Ile Arg Ser Val His
        115                 120                 125

Glu Gly Tyr Ala Phe Ile His Pro Lys Val Thr Gly Lys Leu Ile Gln
    130                 135                 140

Gln Leu Arg Arg Met Thr Tyr Leu Asn Glu Thr Gly Ala Met Ala Glu
145                 150                 155                 160
```

```
Gly His Thr Lys Glu Ala Gly Val Lys Phe Val Ala Gly Glu Asn Asn
            165                 170                 175

Pro Leu Thr Arg Arg Glu Ala Glu Val Leu Arg Leu Met Ala Glu Gly
            180                 185                 190

Lys Ser Asn Lys Met Ile Gly Glu Tyr Leu Phe Ile Ser Glu Lys Thr
            195                 200                 205

Val Lys Asn His Val Ser Ser Ile Leu Gln Lys Met Glu Val Asp Asp
            210                 215                 220

Arg Thr Gln Ala Val Ile Asn Ser Ile Lys Tyr Gly Trp Val Thr Leu
225                 230                 235                 240

<210> SEQ ID NO 3
<211> LENGTH: 385
<212> TYPE: PRT
<213> ORGANISM: Bacillus subtilis

<400> SEQUENCE: 3

Met Asn Lys Thr Lys Met Asp Ser Lys Val Leu Asp Ser Ile Leu Met
1               5                   10                  15

Lys Met Leu Lys Thr Val Asp Gly Ser Lys Asp Glu Val Phe Gln Ile
            20                  25                  30

Gly Glu Gln Ser Arg Gln Gln Tyr Glu Gln Leu Val Glu Glu Leu Lys
            35                  40                  45

Gln Ile Lys Gln Gln Val Tyr Glu Val Ile Glu Leu Gly Asp Lys Leu
        50                  55                  60

Glu Val Gln Thr Arg His Ala Arg Asn Arg Leu Ser Glu Val Ser Arg
65                  70                  75                  80

Asn Phe His Arg Phe Ser Glu Glu Glu Ile Arg Asn Ala Tyr Glu Lys
                85                  90                  95

Ala His Lys Leu Gln Val Glu Leu Thr Met Ile Gln Gln Arg Glu Lys
            100                 105                 110

Gln Leu Arg Glu Arg Arg Asp Asp Leu Glu Arg Arg Leu Leu Gly Leu
        115                 120                 125

Gln Glu Ile Ile Glu Arg Ser Glu Ser Leu Val Ser Gln Ile Thr Val
    130                 135                 140

Val Leu Asn Tyr Leu Asn Gln Asp Leu Arg Glu Val Gly Leu Leu Leu
145                 150                 155                 160

Ala Asp Ala Gln Ala Lys Gln Asp Phe Gly Leu Arg Ile Ile Glu Ala
                165                 170                 175

Gln Glu Glu Glu Arg Lys Arg Val Ser Arg Glu Ile His Asp Gly Pro
            180                 185                 190

Ala Gln Met Leu Ala Asn Val Met Met Arg Ser Glu Leu Ile Glu Arg
        195                 200                 205

Ile Phe Arg Asp Arg Gly Ala Glu Asp Gly Phe Gln Glu Ile Lys Asn
    210                 215                 220

Leu Arg Gln Asn Val Arg Asn Ala Leu Tyr Glu Val Arg Arg Ile Ile
225                 230                 235                 240

Tyr Asp Leu Arg Pro Met Ala Leu Asp Asp Leu Gly Leu Ile Pro Thr
                245                 250                 255

Leu Arg Lys Tyr Leu Tyr Thr Thr Glu Glu Tyr Asn Gly Lys Val Lys
            260                 265                 270

Ile His Phe Gln Cys Ile Gly Glu Thr Glu Asp Gln Arg Leu Ala Pro
        275                 280                 285
```

```
Gln Phe Glu Val Ala Leu Phe Arg Leu Ala Gln Glu Ala Val Ser Asn
    290                 295                 300

Ala Leu Lys His Ser Glu Ser Glu Glu Ile Thr Val Lys Val Glu Ile
305                 310                 315                 320

Thr Lys Asp Phe Val Ile Leu Met Ile Lys Asp Asn Gly Lys Gly Phe
                325                 330                 335

Asp Leu Lys Glu Ala Lys Glu Lys Asn Lys Ser Phe Gly Leu Leu
            340                 345                 350

Gly Met Lys Glu Arg Val Asp Leu Leu Glu Gly Thr Met Thr Ile Asp
        355                 360                 365

Ser Lys Ile Gly Leu Gly Thr Phe Ile Met Ile Lys Val Pro Leu Ser
    370                 375                 380

Leu
385

<210> SEQ ID NO 4
<211> LENGTH: 386
<212> TYPE: PRT
<213> ORGANISM: Paenibacillus sp.

<400> SEQUENCE: 4

Val Asp Phe Gln Ala Asp Ile Ile Asp Arg Val Ile Lys Asn Ala Ile
1               5                   10                  15

Gln Val Met Glu Asn Ser Lys Tyr Gln Met Phe Glu Ile Leu Asp Thr
            20                  25                  30

Ala Arg Thr Glu Leu Ile Thr Leu Asn Gln Glu Leu Gln Ser Val Leu
        35                  40                  45

Lys Glu Thr Ala Glu Thr Ile Glu Lys Val Asp Gln Leu Glu Met Asn
    50                  55                  60

Tyr Arg Arg Ser Arg Ile Arg Leu Thr Glu Val Ser Arg Asp Phe Val
65                  70                  75                  80

Arg Tyr Ser Glu Glu Asp Ile Lys Gln Ala Tyr Glu Lys Ala Thr Gln
                85                  90                  95

Leu Gln Leu Asp Val Met Ile Phe Arg Glu Lys Glu Met Tyr Leu Lys
            100                 105                 110

Ala Arg Arg Asp Asp Leu Gln Lys Arg Ala Lys Ser Val Glu Ala Ser
        115                 120                 125

Val Glu Arg Ala Glu Thr Ile Gly Ser Gln Met Gly Val Val Leu Glu
    130                 135                 140

Tyr Leu Ser Gly Glu Leu Gly Gln Val Thr Arg Ile Ile Glu Ser Ala
145                 150                 155                 160

Lys Asn Arg Gln Phe Ile Gly Leu Lys Ile Ile Leu Ala Gln Glu Glu
                165                 170                 175

Glu Arg Lys Arg Ile Ser Arg Glu Ile His Asp Gly Pro Ala Gln Leu
            180                 185                 190

Leu Ala His Leu Val Leu Arg Thr Glu Ile Val Glu Arg Met Ile Ala
        195                 200                 205

Lys Gln Glu Phe Lys Met Val Gln Asp Glu Ile Val Asp Leu Lys Lys
    210                 215                 220

Gln Val Arg Ser Ser Leu Glu Glu Met Arg Lys Val Ile Phe Asn Leu
225                 230                 235                 240

Arg Pro Met Ala Leu Asp Asp Leu Gly Leu Val Pro Thr Leu Arg Lys
                245                 250                 255
```

Tyr Val Gln Asp Phe Glu Glu Lys Thr Lys Ile Arg Ser Leu Phe Glu
            260                 265                 270

Thr Arg Gly Lys Glu His Arg Leu Ser Ser Ala Met Glu Ala Ala Ile
        275                 280                 285

Tyr Arg Leu Ile Gln Glu Ala Leu Thr Asn Ala Ala Lys His Ala Tyr
    290                 295                 300

Pro Thr Tyr Val Leu Val Glu Ile Thr Tyr Gln Ala Gln Leu Val Lys
305                 310                 315                 320

Ile Val Val Gln Asp Asn Gly Leu Gly Phe Lys Pro Glu Leu Phe Gln
                325                 330                 335

Gln Lys Ser Lys Asp His Gly His Phe Gly Leu Ile Gly Met Arg Glu
                340                 345                 350

Arg Val Glu Leu Leu Glu Gly Arg Met Glu Ile Glu Ser Ala Glu Asn
            355                 360                 365

Gln Gly Thr Lys Ile Val Ile His Ile Pro Thr Asn Val Glu Lys Gly
        370                 375                 380

Lys Glu
385

<210> SEQ ID NO 5
<211> LENGTH: 690
<212> TYPE: DNA
<213> ORGANISM: Bacillus subtilis

<400> SEQUENCE: 5
gtgactaaag taaacattgt tattatcgac gaccatcagt tatttcgtga aggtgttaaa      60
cggatattgg attttgaacc tacctttgaa gtggtagccg aaggtgatga cggggacgaa     120
gcggctcgta ttgttgagca ctatcatcct gatgttgtga tcatggatat caatatgcca     180
aacgtaaatg gtgtggaagc tacaaaacag cttgtagagc tgtatcctga atctaaagta     240
attattctat caattcacga tgacgaaaat tatgtaacac atgccctgaa acaggtgca      300 agaggttatc tgctgaaaga gatggatgct gatacattaa ttgaagcggt taaagtagtg     360
gctgagggcg atcttacct ccatccgaag gttactcaca acctcgttaa cgaattccgc      420
cgccttgcaa caagcggagt ttctgcacac cctcaacatg aggtttaccc tgaaatccgc     480
agaccattac atatttaac taggcgggaa tgtgaagtgc tgcagatgct gcagacgga      540 aaaagcaacc gcggtattgg tgaatcattg tttatcagtg agaaaaccgt taaaaaccat     600
gtcagcaata ttttacaaaa aatgaatgta aacgaccgga cgcaagccgt tgtggtcgcc     660
attaaaaatg gctgggtaga aatgagatag                                      690

<210> SEQ ID NO 6
<211> LENGTH: 723
<212> TYPE: DNA
<213> ORGANISM: Paenibacillus sp.

<400> SEQUENCE: 6
atggaaaatc aggaaattag taacgcaccc attaaagtac tcttggcgga cgatcatcag      60
ttgttccgtg aagggcttaa acgtattttg aatatggagg acgacattga ggtcatcggc     120
gaatgtggcg atggtattca ggtgttggag ttctgtaatg tagagaagcc ggatatcgtt     180
ctgatggaca ttaatatgcc tattgaaaac ggtgtagagg caactgaaaa actgcgtgag     240
atgttcccgg atgtcaaagt tatcattctg tccattcatg atgatgaaag ctatgtattc     300
gagacgttgc gcaagggagc taacggctac ctgttaaaag atatggaggc cgagtccctc     360

```
attaacgcga ttcgctctgt acatgaaggg tatgcgttta ttcatccgaa ggtaacgggt    420
aaactcattc agcagctccg tcggatgacg tacctgaatg aaaccggggc tatggctgaa    480
ggtcatacca aggaagctgg cgtgaagttc gtcgcaggcg aaaataaccc actgacccgt    540
cgtgaggctg aagtgttgcg cttaatggca gaaggcaaga gcaacaagat gatcggtgaa    600
tatttattca ttagtgaaaa aacggtcaaa aaccatgtca gcagtatttt gcaaaaaatg    660
gaggttgatg accggacaca agcggttatt aactcaatca aatacggatg ggttacgctg    720
taa                                                                  723

<210> SEQ ID NO 7
<211> LENGTH: 1158
<212> TYPE: DNA
<213> ORGANISM: Bacillus subtilis

<400> SEQUENCE: 7
atgaataaaa caaagatgga ttccaaagtg ctggattcta ttttgatgaa gatgctgaaa     60
accgttgacg ggagcaagga cgaggttttt caaatcgggg agcagtcacg ccagcagtat    120
gaacagctgg tcgaagaact gaaacaaatt aaacagcagg tgtatgaagt gattgagctt    180
ggcgataaac ttgaagtgca aactcgccat gcgagaaacc gtttatccga ggtcagccgt    240
aattttcata gattcagtga agaggaaatc cgcaatgctt atgaaaaagc cataagctg     300 caggtagaat tgacgatgat ccagcagcgt gagaagcaat gcgcgaacg gcgggacgat    360 ttggagcgca gattgctagg gcttcaggaa atcattgagc ggtcagaatc attagtaagc    420
caaattacag ttgtgctcaa ctacttgaat caggatttgc gcgaagttgg actgcttctt    480
gctgatgctc aggcaaaaca ggatttcggc ttaagaatta ttgaggcgca ggaagaagag    540
cgaaaaagag tctcaagaga atccatgac ggacccgctc aaatgctggc gaatgttatg    600
atgagatcgg aattaatcga gcggattttc cgtgaccggg gcgcagagga cggattccaa    660
gaaattaaaa atctccgcca aaatgttcgg aatgcccttt acgaagtgag aaggattata    720
tatgatttaa gaccgatggc ccttgatgac ctaggcctga ttccaacttt aagaaaatat    780
ctatatacaa ccgaggaata taacgggaag gtcaaaatac attttcagtg cattggagaa    840
acagaggatc agaggctagc gcctcagttt gaggttgcgc tcttcaggct cgcacaggaa    900
gctgtgtcta atgcgctaaa gcattctgaa tctgaagaaa ttacagtcaa agttgagatc    960
acaaaggatt ttgtgatttt aatgataaaa gataacggta aagggttcga cctgaaggaa   1020
gcgaaagaga agaaaaacaa atcattcggc ttgctgggca tgaaagaaag agtagattta   1080
ttggaaggaa cgatgacaat agattcgaaa ataggtcttg ggacatttat tatgattaag   1140
gttccgttat ctctttga                                                1158

<210> SEQ ID NO 8
<211> LENGTH: 1161
<212> TYPE: DNA
<213> ORGANISM: Paenibacillus sp.

<400> SEQUENCE: 8
gtggactttc aagccgatat catagaccga gtcattaaga atgccattca ggtgatggag     60
aacagtaaat atcagatgtt cgaaattttg acacggcccc ggaccgagct gatcacatta    120
aatcaggaac tccagagcgt cctgaaggaa acggcagaaa cgattgaaaa ggtggaccag    180
ttggaaatga actatcggcg gtcccgtatt cggctgactg aggtcagccg tgactttgtc    240
```

```
cgctattcgg aagaggatat caagcaggct tacgagaaag caacacagct tcagctcgat    300
gtgatgatct ttcgcgagaa ggaaatgtac ctcaaggcca gaagagatga tcttcaaaag    360
cgggctaaaa gtgtcgaggc ctctgtcgag cgggccgaaa ccatcggttc gcagatgggc    420
gtcgtgctgg aatacttgtc gggtgagttg gacaagtaa cgcggatcat cgaatcggcc     480
aaaaaccggc agtttattgg tctgaaaatt attttagccc aggaagagga gcgcaagcgg    540
atatcccgtg aaattcacga tggacctgca cagcttcttg cgcatctagt gcttaggacg    600
gaaattgtgg aaagaatgat cgccaagcag gaatttaaga tggttcagga cgaaatagta    660
gacttgaaga acaggttcg ctccagtctt gaggaaatgc gaaaggttat tttcaatctg     720
cgtcctatgg ccctggatga cttgggactt gttccgacgc tccggaaata tgtgcaggat    780
tttgaagaga aaacgaagat tagatcgctt tttgaaacaa ggggcaagga acaccgtctc    840
tcttccgcga tggaagcagc catttaccgt ctgatccaag aagctttgac caacgctgcc    900
aagcatgctt atcctaccta tgtgcttgtt gagattactt atcaggcgca gcttgtaaaa    960
atcgtggtgc aggataacgg tctgggcttt aagccagagc tttttcagca gaaaagcaaa   1020
gatcatgggc attttggtct gattggtatg cgggaaaggg ttgaactgct cgaggggaga   1080
atggagatcg aatcagctga gaatcaaggc accaagatag tgattcatat cccaaccaac   1140
gtggaaaagg gaaaggagta a                                             1161
```

<210> SEQ ID NO 9
<211> LENGTH: 533
<212> TYPE: PRT
<213> ORGANISM: Paenibacillus sp.

<400> SEQUENCE: 9

Met Thr Arg Asn Lys Cys Leu Arg Arg Leu Ser Thr Ala Met Leu Thr
1               5                   10                  15

Val Pro Met Leu Thr Met Phe Ala Ser Gly Ala Met Ala Glu Gln Glu
            20                  25                  30

Met Asn Gly His Lys Pro Pro Val Ser Thr Gly Ser Gly Val Phe Tyr
        35                  40                  45

Glu Ile Tyr Ile Asn Ser Phe Tyr Asp Ser Asn Gly Asp Gly His Gly
    50                  55                  60

Asp Leu Lys Gly Ile Thr Gln Lys Leu Asp Tyr Leu Asn Asp Gly Asn
65                  70                  75                  80

Pro Arg Ser Gly Lys Asp Leu Gln Ile Ser Gly Leu Trp Leu Met Pro
                85                  90                  95

Leu Asn Pro Ser Pro Ser Tyr His Lys Tyr Asp Val Thr Asp Tyr Tyr
            100                 105                 110

Gln Val Asp Pro Gln Tyr Gly Asn Leu Asn Asp Phe Arg Thr Leu Met
        115                 120                 125

Lys Glu Ala Asp Arg Lys Gly Ile Lys Val Ile Met Asp Leu Val Ile
    130                 135                 140

Asn His Ser Ser Ser Glu His Pro Trp Phe Lys Glu Gly Ser Val Asn
145                 150                 155                 160

Pro Gln Ser Lys Tyr His Asp Tyr Tyr Val Trp Ala Asp Lys Asn Thr
                165                 170                 175

Asp Leu Asp Glu Lys Gly Ser Trp Gly Gln Gln Val Trp His Lys Asn
            180                 185                 190

Pro Asn Gly Glu Gly Tyr Phe Tyr Gly Thr Phe Trp Ser Gly Met Pro
        195                 200                 205

```
Asp Leu Asn Phe Asp Asn Leu Glu Val Arg Lys Glu Met Ile Lys Val
    210                 215                 220

Gly Lys Tyr Trp Leu Gln Gln Gly Ala Asp Gly Phe Arg Leu Asp Ala
225                 230                 235                 240

Ala Met His Ile Phe Lys Gly Gln Thr Lys Glu Gly Ala Asp Lys Asn
                245                 250                 255

Ile Ala Trp Trp Asn Glu Phe Arg Ser Glu Met Glu Lys Val Asn Pro
            260                 265                 270

Asn Val Tyr Leu Ala Gly Glu Val Trp Asp Lys Pro Glu Thr Ile Ala
        275                 280                 285

Pro Tyr Tyr Gly Pro Leu His Ser Leu Phe Asn Phe Asp Leu Gly Gly
    290                 295                 300

Thr Ile Leu Asn Ser Ile Lys Asn Gly Gln Asp Gln Gly Ile Ala Thr
305                 310                 315                 320

Phe Ala Glu Lys Thr Leu Lys Leu Tyr Lys Ser Tyr Asn Lys Ala Ala
                325                 330                 335

Leu Asp Ala Pro Phe Leu Ser Asn His Asp Gln Thr Arg Val Met Ser
            340                 345                 350

Glu Leu Gly Gly Asp Val Arg Lys Ala Lys Leu Ala Ala Ser Ile Leu
        355                 360                 365

Leu Thr Leu Pro Gly Gln Pro Phe Leu Tyr Tyr Gly Glu Glu Ile Gly
370                 375                 380

Met Lys Gly Glu Lys Pro Asp Glu Tyr Leu Arg Glu Pro Met Arg Trp
385                 390                 395                 400

Tyr Lys Gly Asp Gly Pro Gly Gln Thr Thr Trp Glu Glu Pro Lys Tyr
                405                 410                 415

Asn Thr Gly Glu Val Ser Val Glu Ala Gln Leu Arg Asp Asp Asp Ser
            420                 425                 430

Leu Leu Glu Ser Tyr Arg Ser Leu Ile Arg Leu Arg Glu Glu His Glu
        435                 440                 445

Ala Leu Arg Ser Asp Ser Leu Glu Pro Ile Gln Ala Gly Ser Ala Ser
    450                 455                 460

Val Thr Ala Phe Lys Arg Thr Ser Gly Lys Glu Thr Leu Tyr Val Tyr
465                 470                 475                 480

His Asn Leu Ser Gly Glu Pro Val Thr Leu Gln Ile Lys Asp Trp Asp
                485                 490                 495

Lys Gly Lys Trp Lys Val Val Phe Ser Thr Ser Lys Asp Met Lys Val
            500                 505                 510

Lys Lys Gly Thr Val Val Ile Pro Ala Tyr Gly Ser Leu Ile Thr Lys
        515                 520                 525

Glu Asp Arg Lys Ser
    530

<210> SEQ ID NO 10
<211> LENGTH: 949
<212> TYPE: PRT
<213> ORGANISM: Paenibacillus sp.

<400> SEQUENCE: 10

Met Leu Gly Lys Lys Thr Gly Ser Phe Ile Ser Trp Leu Ile Ile Leu
1               5                   10                  15

Ser Leu Cys Phe Asn Phe Phe Gly Leu Pro Gly Val Ala Ser Ala Ser
                20                  25                  30

Ser Thr Asp Tyr Thr Ala Thr Tyr Thr Asn Ser Thr Ala Thr Thr Leu
            35                  40                  45
```

```
Pro Ser Thr Thr Ala Ser Ile Thr Ser Thr Val Thr Ala Thr Tyr Ala
    50                  55                  60

Pro Thr Thr Ile Pro Lys Ser Thr Gln Thr Gly Leu Thr Val His Phe
65                  70                  75                  80

Lys Lys Pro Ser Ser Trp Asn Ser Ala Ile Arg Ile His Tyr Trp Asn
                85                  90                  95

Leu Asn Pro Thr Thr Val Pro Ile Ser Gly Ala Trp Pro Gly Ile Leu
                100                 105                 110

Met Lys Ser Asp Gly Asn Asp Trp Tyr Ser Tyr Thr Ile Ala Glu Ala
            115                 120                 125

Thr Gly Ser Ser Leu Ile Phe Asn Asp Gly Ser Gly Lys Gln Thr Ala
        130                 135                 140

Asp Leu Ser Arg Ser Val Lys Glu Gly Trp Tyr Tyr Thr Asp Asn Thr
145                 150                 155                 160

Trp Tyr Asp Thr Ser Pro Glu Met Pro Lys Ile Pro Ala Ile Ser Ala
                165                 170                 175

Ser Pro Val Pro Lys Thr Tyr Asp Ser Ser Gln Ser Val Thr Leu Ser
                180                 185                 190

Ser Thr Asn Ser Asp Asp Lys Ile Tyr Tyr Thr Ile Asp Gly Ser Thr
        195                 200                 205

Pro Thr Thr Ser Ser Thr Leu Tyr Thr Ser Pro Ile Gln Val Ala Ser
210                 215                 220

Ser Leu Thr Ile Lys Ala Phe Gly Val Asn Ser Ile Gly Gln Thr Gly
225                 230                 235                 240

Asn Ala Ser Ser Phe Ala Tyr Met Ile Asp Leu Asn Ser Asp Leu Gln
                245                 250                 255

Ala Pro Thr Ile Thr Ala Asn Leu Pro Thr Arg His Ser Asp Ser Ser
                260                 265                 270

Val Thr Val Ser Phe Asn Leu Asn Asp Asn Lys Ala Ala Thr Thr Lys
            275                 280                 285

Ala Tyr Tyr Thr Asp Asp Gly Thr Glu Pro Thr Ile Ser Ser Lys Val
        290                 295                 300

Tyr Ile Leu Gly Asn Ala Met Ala Gly Leu Thr Gly Pro Ser Ile Leu
305                 310                 315                 320

Ile Ser Lys Thr Thr Leu Lys Phe Leu Val Ile Asp Gly Ala Gly
                325                 330                 335

Asn Gln Thr Lys Gln Ser Phe Val Tyr Asn Ile Gly Asn Lys Gly Asp
            340                 345                 350

Phe Arg Glu Asp Thr Ile Tyr Phe Val Ile Thr Ser Arg Phe Tyr Asp
        355                 360                 365

Gly Asp Pro Ser Asn Asn Met His Ala Trp Asp Ala Lys Ala Arg
370                 375                 380

Asn Pro Asp Ser Asp Pro Ala Trp Arg Gly Asp Phe Lys Gly Leu Ile
385                 390                 395                 400

Gln Lys Leu Asp Tyr Ile Lys Ala Leu Gly Phe Ser Ala Val Trp Ile
                405                 410                 415

Thr Pro Val Val Gln Asn Ala Ser Gly Tyr Asp Tyr His Gly Tyr His
                420                 425                 430

Ala Ile Asn Phe Ala Lys Val Asp Pro Arg Tyr Glu Ser Ala Gly Ala
            435                 440                 445

Ser Tyr Gln Asp Leu Ile Asn Ala Ala His Ala Lys Gly Leu Lys Val
        450                 455                 460
```

```
Ile Gln Asp Ile Val Val Asn His Thr Gly Asn Phe Gly Glu Glu Asn
465                 470                 475                 480

Leu Tyr Pro Met Phe Lys Lys Asp Pro Ala Lys Pro Asp Thr Ala Asn
                485                 490                 495

Asn Leu Val Lys Thr Thr Asp Lys Leu Pro Ser Asn Tyr Asp Thr Met
            500                 505                 510

Thr Pro Asp Gln Gln Tyr Gln Ala Arg Leu Ala Leu Met Lys Asn Ala
        515                 520                 525

Glu Thr Asn Asn Asn Ile Tyr His Thr Glu Lys Ser Leu Ser Trp Glu
    530                 535                 540

Ser Tyr Thr Val Gln Thr Gly Gln Ile Ala Gly Asp Cys Val Asp Leu
545                 550                 555                 560

Asn Thr Glu Asn Pro Ala Val Asn Glu Tyr Leu Ile Asp Thr Tyr Asn
                565                 570                 575

His Tyr Ile Asp Met Gly Val Asp Ala Phe Arg Val Asp Thr Val Lys
            580                 585                 590

His Val Ser Arg Tyr Ile Phe Asn Lys Tyr Tyr Ile Pro Ala Trp Lys
        595                 600                 605

Thr Arg Gly Gly Ser Asp Phe Tyr Ile Phe Gly Glu Val Ala Thr Arg
    610                 615                 620

Tyr Arg Asp Val Trp Asn Ser Gly Ile Pro Ala Ile Ser Thr Pro Phe
625                 630                 635                 640

Tyr Thr Trp Lys Ser Ser Lys Ser Tyr Pro Gly Asp Gly Lys Asn Asp
                645                 650                 655

Tyr Ala Ser Asn Lys Val Ser Val Glu Gln Glu Trp Ala Asp Asn Ser
            660                 665                 670

Thr Thr Ala Gly Gln Pro Thr Ser Asn Asn Ala Leu Leu Asn Gly Asn
        675                 680                 685

Thr Tyr His Thr Pro Asp Tyr Ser Met Lys Ser Gly Met Asp Val Ile
    690                 695                 700

Asp Phe Pro Met His Trp Ala Phe Lys Thr Ala Gln Glu Ala Phe Asn
705                 710                 715                 720

Met Arg Ser Gly Asp Gln Tyr Tyr Asn Asp Ala Thr Trp Asn Val Thr
                725                 730                 735

Tyr Ile Asp Ser His Asp Tyr Ala Pro Asp Gln Ala Pro Glu Asn Gln
            740                 745                 750

Arg Phe Ala Gly Thr Gln Asp Thr Trp Ala Glu Asn Leu Asp Leu Met
        755                 760                 765

Phe Thr Phe Arg Gly Ile Pro Ala Ile Phe Tyr Gly Ser Glu Ile Glu
    770                 775                 780

Phe Gln Lys Gly Ala Val Ile Asp Pro Gly Pro Asn Ala Pro Leu Ser
785                 790                 795                 800

Lys Thr Gly Arg Ala Tyr Phe Gly Asp His Met Glu Gly Asn Val Thr
                805                 810                 815

Val Gln Asp Tyr Gly Lys Tyr Thr Asn Ala Thr Gly Thr Leu Ala Glu
            820                 825                 830

Ser Leu Asn His Pro Leu Ala Lys His Ile Arg Gln Leu Asn Leu Ile
        835                 840                 845

Arg Arg Ala Val Pro Ala Leu Gln Lys Gly Gln Tyr Ser Thr Glu Asn
    850                 855                 860

Val Thr Gly Asn Leu Ala Phe Lys Arg Arg Tyr Thr Asp Ser Ala Lys
865                 870                 875                 880
```

```
Gly Ile Asp Ser Phe Ala Leu Val Thr Ile Ser Gly Asn Ala Thr Phe
            885                 890                 895

Thr Gly Ile Pro Asn Gly Thr Tyr Val Asp Ala Val Thr Gly Asn Ser
            900                 905                 910

Lys Thr Val Thr Asp Gly Lys Ile Thr Leu Thr Cys Ser Gly Lys Gly
            915                 920                 925

Asn Ala Arg Val Tyr Val Leu Asn Gly Ser Gly Gly Ile Gly Glu Thr
            930                 935                 940

Gly Thr Tyr Leu Lys
945
```